US008603975B2

(12) United States Patent
Yamanaka et al.

(10) Patent No.: US 8,603,975 B2
(45) Date of Patent: Dec. 10, 2013

(54) CYCLIC PEPTIDE COMPOUNDS

(75) Inventors: Toshio Yamanaka, Tokyo (JP); Hidenori Ohki, Tokyo (JP); Junya Ishida, Tokyo (JP); Ayako Toda, Tokyo (JP); Yu Harayama, Tokyo (JP); Takuya Makino, Tokyo (JP); Shigeki Kunikawa, Tokyo (JP); Hiroaki Mizuno, Osaka (JP); Hiroaki Ohtake, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 909 days.

(21) Appl. No.: 12/598,404

(22) PCT Filed: Apr. 25, 2008

(86) PCT No.: PCT/JP2008/058456
§ 371 (c)(1),
(2), (4) Date: Oct. 30, 2009

(87) PCT Pub. No.: WO2008/139986
PCT Pub. Date: Nov. 20, 2008

(65) Prior Publication Data
US 2010/0120672 A1 May 13, 2010

(30) Foreign Application Priority Data

May 2, 2007 (AU) ................................. 2007902312

(51) Int. Cl.
*A61K 38/12* (2006.01)
*A61P 31/12* (2006.01)

(52) U.S. Cl.
USPC ............................................ 514/11; 530/321

(58) Field of Classification Search
None
See application file for complete search history.

(56) References Cited

U.S. PATENT DOCUMENTS

| 6,927,208 B1 | 8/2005 | Wenger et al. |
| 2009/0170755 A1* | 7/2009 | Neya et al. ....................... 514/11 |

FOREIGN PATENT DOCUMENTS

| WO | WO-00/01715 | 1/2000 |
| WO | WO-02/32447 A2 | 4/2002 |
| WO | WO-2005/021028 A1 | 3/2005 |
| WO | WO-2005/032576 A1 | 4/2005 |
| WO | WO-2006-038088 A1 | 4/2006 |
| WO | WO-2006/039668 A2 | 4/2006 |
| WO | WO-2006/054801 A1 | 5/2006 |
| WO | WO-2007/049803 A1 | 5/2007 |

OTHER PUBLICATIONS

Office Action in corresponding Russian Application No. 2009144538/04(063434) dated Mar. 9, 2011.
European Office Action dated Dec. 8, 2010.
Choo et al., "Isolation of a cDNA Clone Derived From a Blood-Borne Non-A, Non-B Viral Hepatitis Genome," Science, vol. 244, pp. 359-362, ((1989).
Watashi et al., "Cyclosporin A Suppresses Replication of Hepatitis C Virus Genome in Cultured Hepatocyts", Hepatology, vol. 38, No. 5, pp. 1282-1288, (2003).
Nakagawa et al., "Specific Inhibition of Hepatitis C Virus Replication by Cyclosporin A", Biochemical and Biophysical Research Communication, vol. 313, pp. 42-47, (2004).
Ma et al., "NIM811, A Cyclophilin Inhibitor, Exhibits Potent In Vitro Activity Against Hepatitis C Virus Alone or in Combination With Alpha Interferon", Antimicrobial Agents and Chemotherapy, vol. 50, No. 9, pp. 2976-2982, (2006).
Major et al., "Hepatitis C Viruses", Virology, 4$^{th}$ Edition, Chapter 34, pp. 1127-1161, (2001).
Lohmann et al., "Replication of Subgenomic Hepatitis C Virus RNAs in a Hepatoma Cell Line", Science, vol. 285, pp. 110-113, (1999).
Thall et al, "Functional Association of Cyclophilin A With HIV-1 Virions", Nature, vol. 372, pp. 363-365, (1994).
Inoue et al., "Antiviral Effect of Cyclosporin A on HCV Propagation", 6$^{th}$ International Symposium on Hepatitis C and Related Virus, p. 268, (1999), NIH, Jun. 6-9, Bethesda, MD.
Berenguer et al., "HCV-Related Fibrosis Progression Following Liver Transplantation: Increase in Recent Years", Journal of Hepatology, vol. 32, pp. 673-684, (2000).
Eberle et al., "Cyclosporin A: Regioselective Ring Opening and Fragmentation Reactions Via Thioamides. A Route to Semisynthetic Cyclosporins", J. Org. Chem., vol. 59, pp. 7249-7258, (1994).
Ko et al., "Solid-Phase Total Synthesis of Cyclosporine Analogues", Helvetica Chimica Acta, vol. 80, pp. 695-705, (1997).
Sakamoto et al., "Taxonomy of the Producing Organism, Fermentation, Isolation, Physico-Chemical Properties and Biological Activities", The Journal of Antibiotics, vol. 46, No. 12, pp. 1788-1798, (1993).
Pileri et al., "Binding of Hepatitis C Virus to CD81." Science, vol. 282, pp. 938-941 (1998).
International Search Report from the European Patent Office for International Application No. PCT/JP2008/058456 (Aug. 21, 2008).

* cited by examiner

*Primary Examiner* — Scott Long
*Assistant Examiner* — Sarah Alawadi
(74) *Attorney, Agent, or Firm* — Finnegan, Henderson, Farabow, Garrett & Dunner, L.L.P.

(57) ABSTRACT

The present invention relates to a new cyclic peptide compound or a salt thereof, which has anti-hepatitis C virus activities based on inhibitory activity against the RNA replication of hepatitis C virus replicon, a process for preparation thereof, a pharmaceutical composition comprising the same, and a method for prophylactic and/or therapeutic treatment of hepatitis C in a human being or an animal.

5 Claims, No Drawings

CYCLIC PEPTIDE COMPOUNDS

TECHNICAL FIELD

The present invention relates to a new cyclic peptide compound or a salt thereof having inhibitory activity against the RNA replication of hepatitis C virus (hereafter referred to as HCV) replicon. In particular, the present invention relates to a new peptide compound or a salt thereof, to a process for preparation thereof, to a pharmaceutical composition comprising the new cyclic peptide compound or a salt thereof, and to a method for the prophylactic and/or therapeutic treatment of hepatitis C in a human being or animal.

BACKGROUND ART

The estimated number of HCV carriers is about 170 million worldwide (about 3%) and about 1.5 million in Japan. Even in the combination therapy of using interferon (hereafter referred to as IFN) and ribavirin (Virazole), available as a first option for treatment, its effectiveness is 40% for all types of HCV. Furthermore, its effectiveness is only 15 to 20% for IFN-resistant virus (genotype 1b), particularly abundantly found in Japan. On the other hand, the combination therapy has side effects frequently. It is thus difficult to get rid of the virus completely by using currently available treatment methods. In the case when chronic hepatitis cannot be cured completely, the hepatitis will securely develop into cirrhosis hepatitis (30%) or hepatocellular carcinoma (25%). In Europe and the United States, hepatitis C has been a major indication for liver transplant. However, the redevelopment of HCV occurs frequently even in transplanted livers. For these reasons, the needs for new agents being improved in both effectiveness and safety, having higher antiviral effects and capable of inhibiting hepatitis C are very strong in society.

A new cyclic peptide compound or a salt thereof having inhibitory activity against the RNA replication of HCV having is disclosed in WO2007/049803, which was published after priority date of present application.

HCV is a virus having plus-strand RNA as a gene and is classified into Flaviviridae in accordance with the analysis of the base sequence of the gene. According to Fields Virology fourth edition, D. Knipe et al ed., Philadelphia, Lippincott Williams & Wilkins 2001, 1127-1161, although the existence of HCV was anticipated in 1970s, the discovery of HCV was very difficult. HCV was called non-A non-B hepatitis virus for many years. In 1989, according to Choo Q-L et al., *Science* 244, 359-362 (1989), part of the gene of this virus was cloned from the serum of an infected laboratory animal, and its cDNA sequence was identified and confirmed, whereby the virus was named "HCV".

DISCLOSURE OF THE INVENTION

Cyclosporin A is used as an immunosuppressant for organ transplant. M. Thali et al., *Nature* 372, 363-365 (1994) reported that Cyclosporin A had anti-HIV activity by inhibiting the interaction between Cyclosporin A and the virus particle forming protein of Human Immunodeficiency Virus Type 1 (HIV-1). Furthermore, K. Inoue et al., 6th International Symposium on Hepatitis C and Related Virus, 3-6 Jun. (2000) Bethesda, Md., USA reported that Cyclosporin A had an anti-HCV activity. However, reports for supporting this finding are not presented by other groups up until now.

M. Berenguer et al., *J. Hepatol* 32, 673-684 (2000) reported that the clinical use of Cyclosporin A serving as an immunosuppressant caused HCV to multiply in transplant patients.

Hence, an anti-hepatitis C agent improved in the activity, transition in blood, selectivity and the side effects, for example, in comparison with Cyclosporin A, has been demanded because of the above-mentioned reasons.

The object cyclic peptide compound in the present invention is a new compound, and can be represented by the following general formula (I):

(I)

wherein
$R^1$ and $R^2$ are independently hydrogen, lower alkyl, —O-(lower alkyl), —NH-(lower alkyl), —S-(lower alkyl), aryl or heteroaryl;
$R^3$ is (1) —OH or —SO$_2$Ph;
  (2) heterocyclic group which may have one or more suitable substituent(s);
  (3) —NR$^8$R$^9$, wherein $R^8$ and $R^9$ are independently hydrogen, lower alkyl, heterocyclic group or acyl, each of which may have one or more suitable substituent(s); or alternatively $R^8$ and $R^9$, together with the nitrogen atom to which they are attached, represent N-containing heterocyclic group which may have one or more suitable substituent(s);
  (4) —OC(O)—NR$^{10}$R$^{11}$, wherein $R^{10}$ and $R^{11}$ are independently hydrogen, lower alkyl, cyclo(lower)alkyl, aryl or heterocyclic group, each of which may have one or more suitable substituent(s); or alternatively $R^{10}$ and $R^{11}$, together with the nitrogen atom to which they are attached, represent N-containing heterocyclic group, which may have one or more suitable substituent(s);
  (5) —O—R$^{12}$, wherein $R^{12}$ is lower alkyl or aryl, each of which may have one or more suitable substituent(s); or
  (6) —S—R$^{13}$, wherein $R^{13}$ is lower alkyl, acyl or heterocyclic group, each of which may have one or more suitable substituent(s);
$R^4$ is hydrogen or lower alkyl;
$R^5$ is lower alkyl;
$R^6$ is hydrogen, lower alkyl or lower alkenyl, each of which may have one or more suitable substituent(s);
$R^7$ is hydrogen or lower alkyl; and
⁃⁃⁃⁃⁃ represents single bond or double bond;
or a salt thereof.

Preferred embodiments of the object compound (I) are as follows.
1) The compound of the general formula (I),
  wherein
  $R^4$ is hydrogen or methyl;
  $R^5$ is methyl or ethyl; and $R^7$ is hydrogen, methyl or ethyl;
or a salt thereof.
2) The compound of 1),
   wherein
   $R^4$ is hydrogen; and
   $R^7$ is hydrogen;
   or a salt thereof.
3) The compound of 1)-2),
   wherein
   $R^1$ is methyl; and
   $R^2$ is hydrogen;
   or a salt thereof.
4) The compound of 1)-3),
   wherein
   ----- moiety is double bond;
   or a salt thereof.
5) The compound of 1)-4),
   wherein
   $R^6$ is hydrogen or lower alkyl which may have one or more suitable substituent(s);
   or a salt thereof.

More preferred embodiments of the object compound (I) are as follows.
a) The compound of the general formula (I),
   wherein
   $R^1$ is methyl;
   $R^2$ is hydrogen;
   $R^4$ is hydrogen;
   $R^5$ is methyl or ethyl;
   $R^7$ is hydrogen; and
   ----- moiety is double bond;
   or a salt thereof.
b) The compound of a),
   wherein
   $R^6$ is —CH$_2$OH, —CH$_2$OMe, —CH$_2$OEt, —CH$_2$OC(O)Me or —CH$_2$Ph;
   or a salt thereof.
c) The compound of b),
   wherein
   $R^3$ is (1) heterocyclic group which may have one or more suitable substituent(s);
   (2) —NR$^8$R$^9$, wherein $R^8$ and $R^9$ are independently hydrogen; or lower alkyl or acyl, each of which may have one or more suitable substituent(s); or alternatively $R^8$ and $R^9$, together with the nitrogen atom to which they are attached, represent N-containing heterocyclic group which may have one or more suitable substituent(s);
   (3) —OC(O)—NR$^{10}$R$^{11}$, wherein $R^{10}$ and $R^{11}$ are independently hydrogen; or lower alkyl, cyclo(lower)alkyl, aryl or heterocyclic group, each of which may have one or more suitable substituent(s); or alternatively $R^{10}$ and $R^{11}$, together with the nitrogen atom to which they are attached, represent N-containing heterocyclic group, which may have one or more suitable substituent(s);
   or a salt thereof.

The compound (I) or a salt thereof in the present invention can be prepared by the processes as illustrated in the following reaction schemes Process 1-6.

And the starting compounds or a salt thereof in the present invention can be prepared, for example, by the processes as illustrated in the following reaction schemes Process A-H.

Process 1

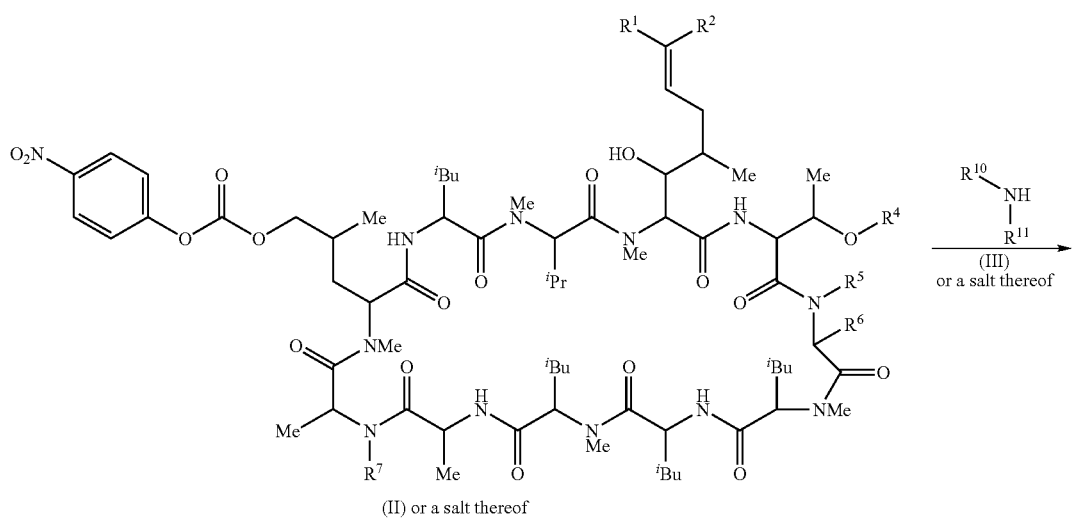

(II) or a salt thereof

-continued
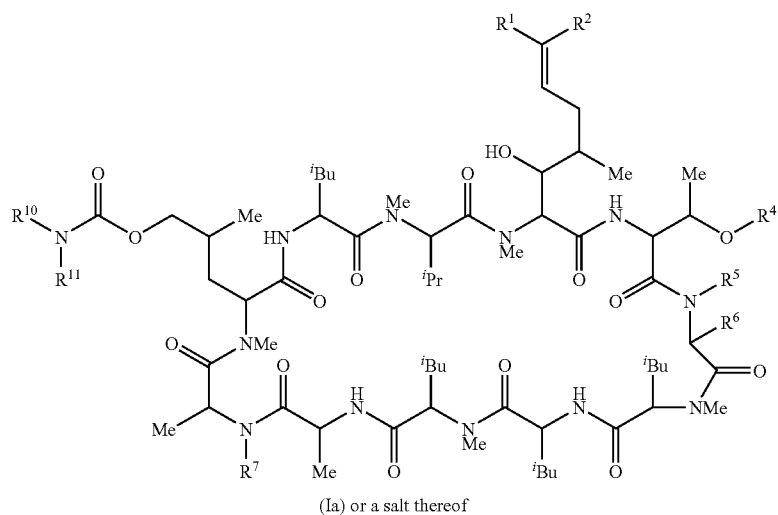
(Ia) or a salt thereof
Process 2
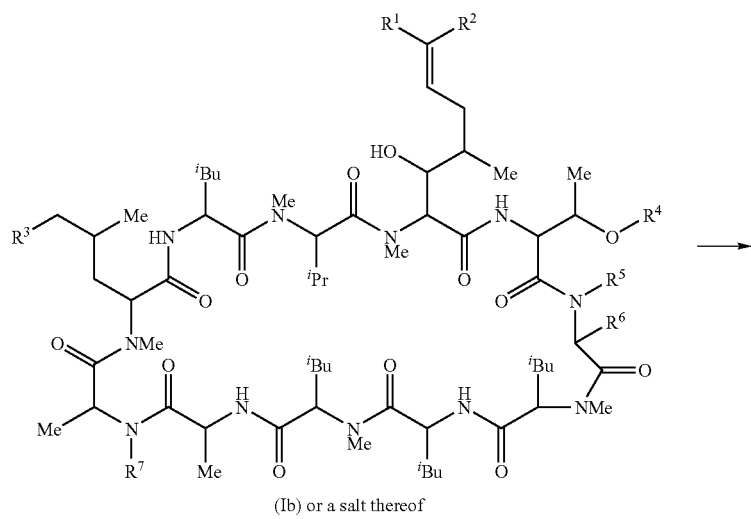
(Ib) or a salt thereof
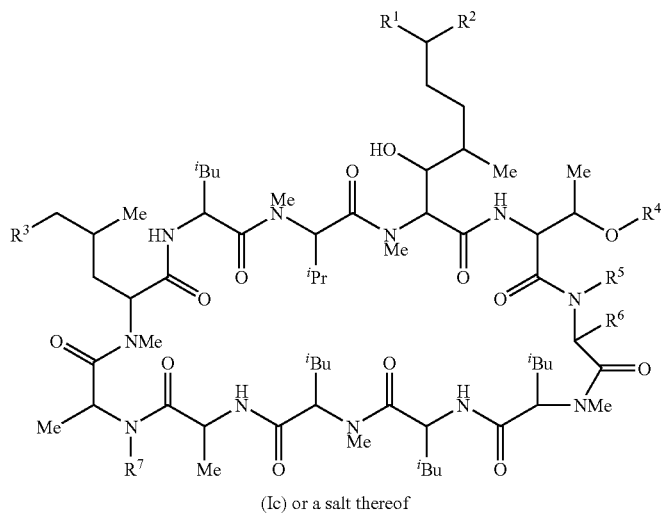
(Ic) or a salt thereof -continued
Process 3
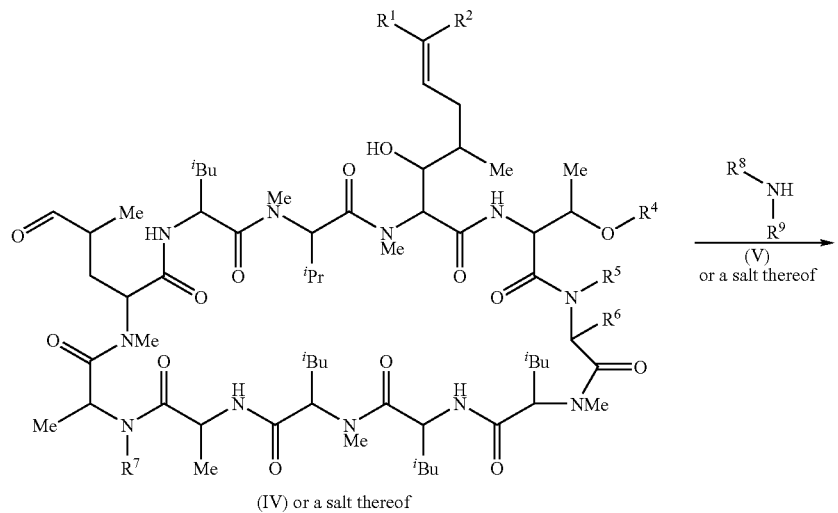
(IV) or a salt thereof
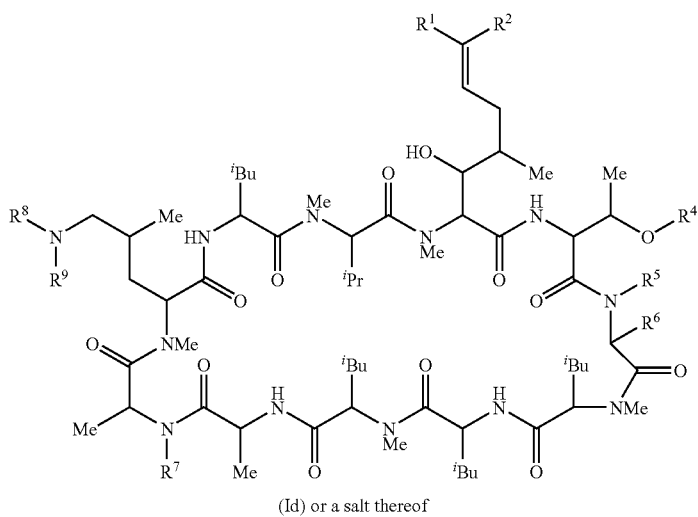
(Id) or a salt thereof
Process 4
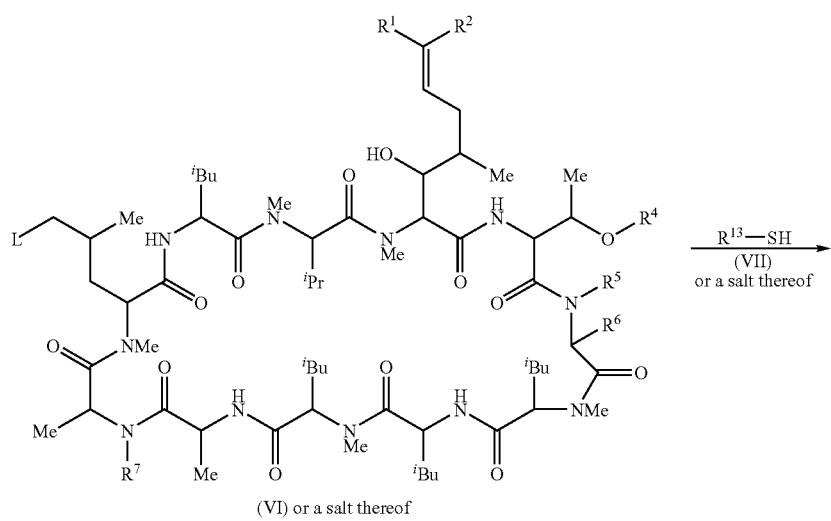
(VI) or a salt thereof -continued
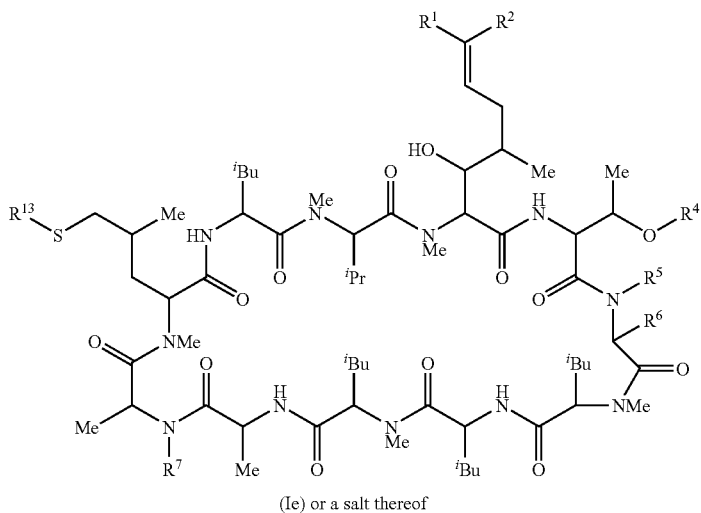
(Ie) or a salt thereof
Process 5
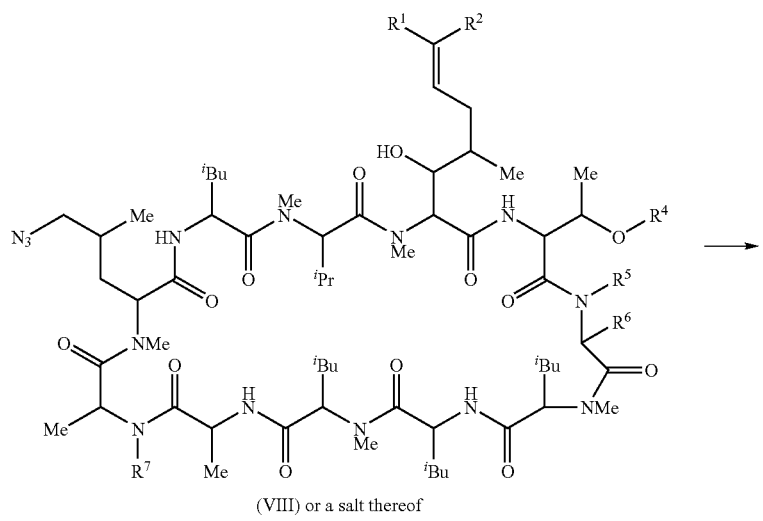
(VIII) or a salt thereof
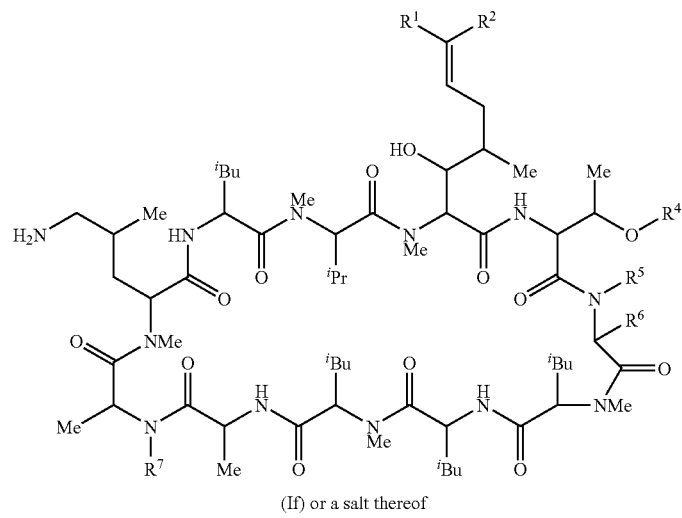
(If) or a salt thereof -continued
Process 6
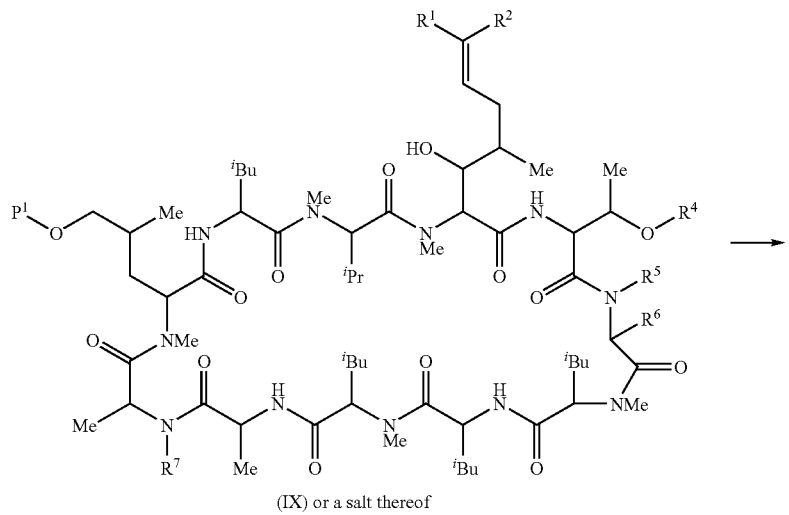
(IX) or a salt thereof
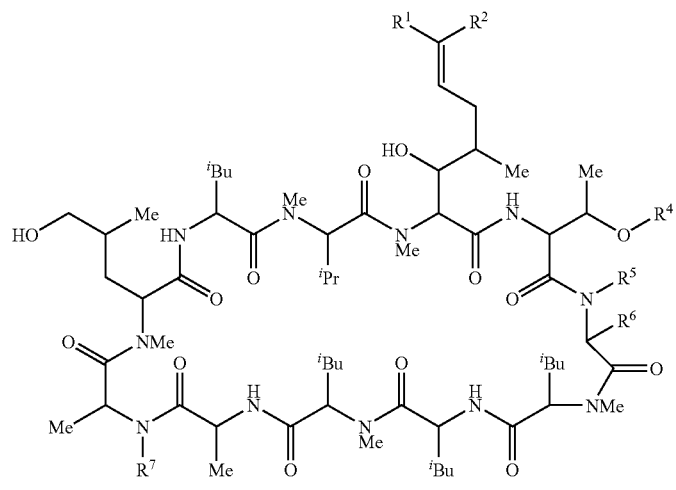
(Ig) or a salt thereof
Process 7
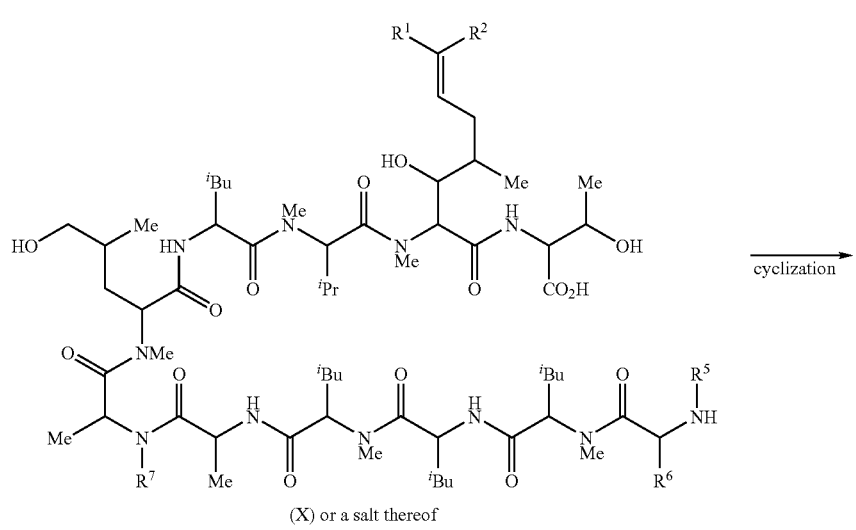
(X) or a salt thereof
cyclization →

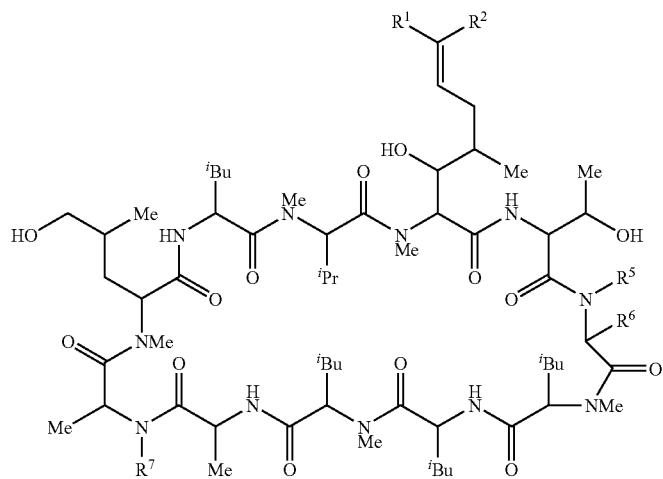
(Ig) or a salt thereof
Process A
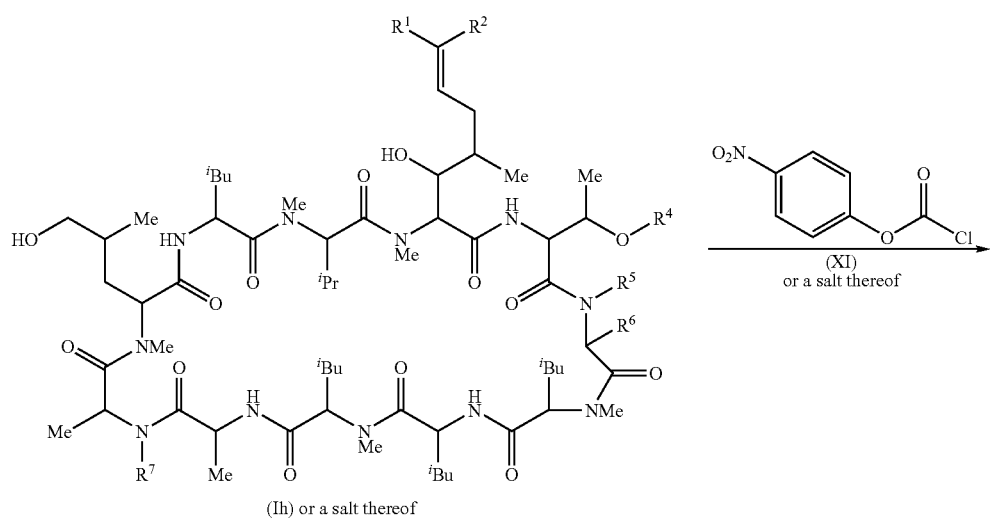
(Ih) or a salt thereof
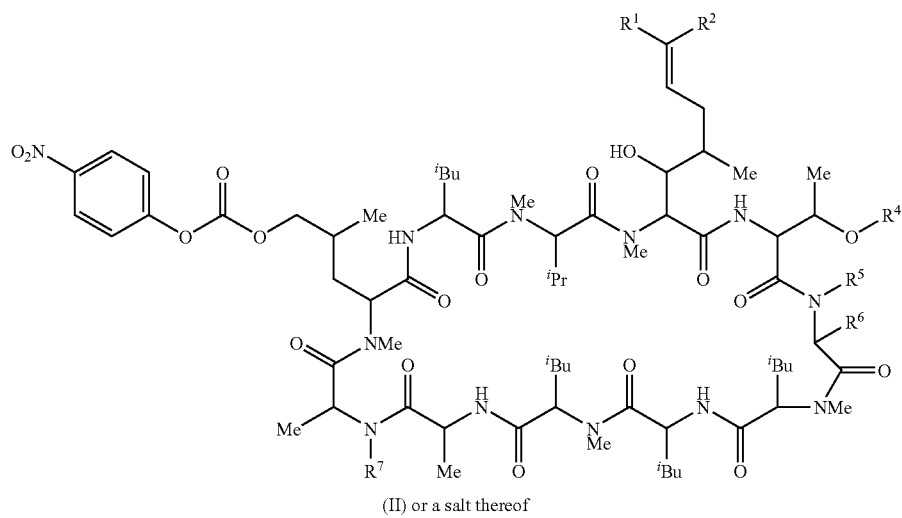
(II) or a salt thereof -continued
Process B
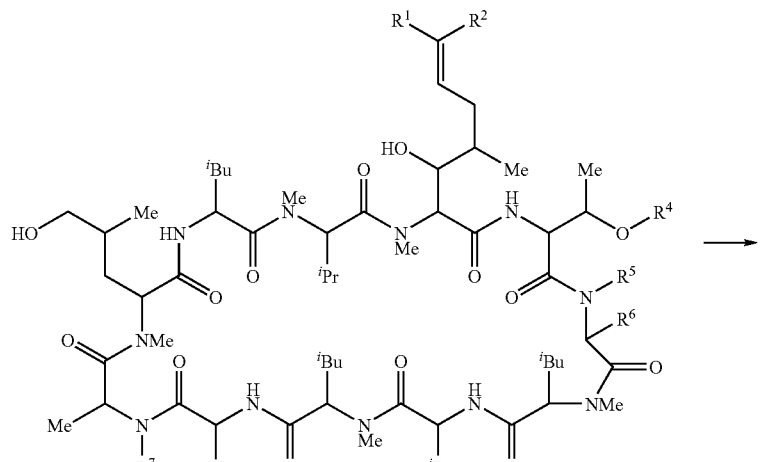
(Ii) or a salt thereof
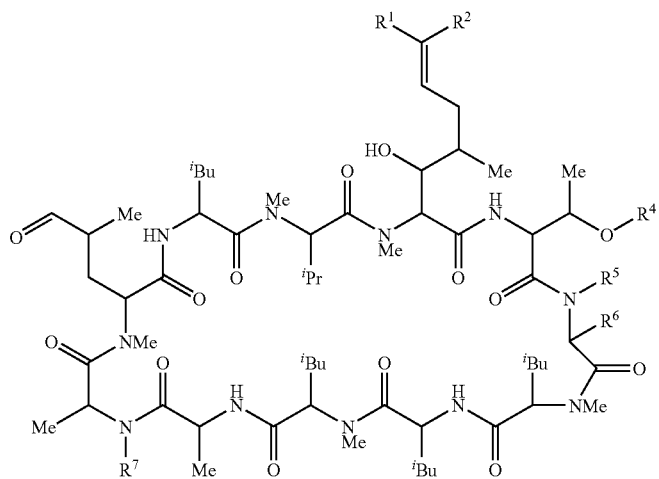
(IV) or a salt thereof
Process C
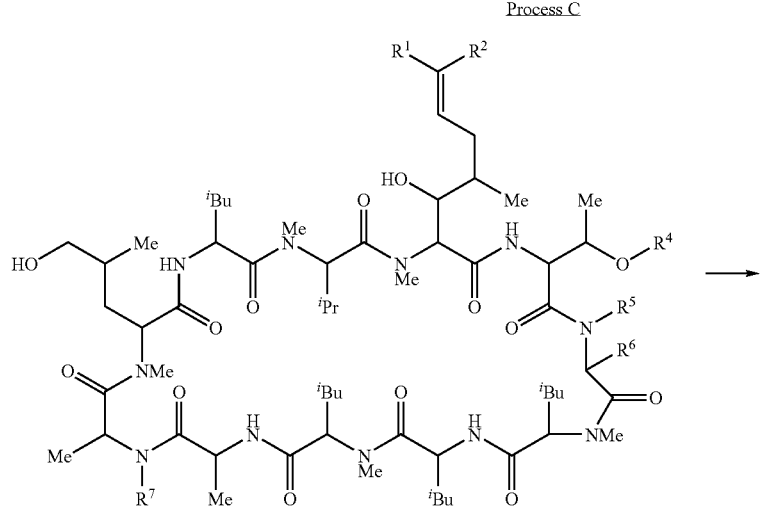
(Ii) or a salt thereof -continued
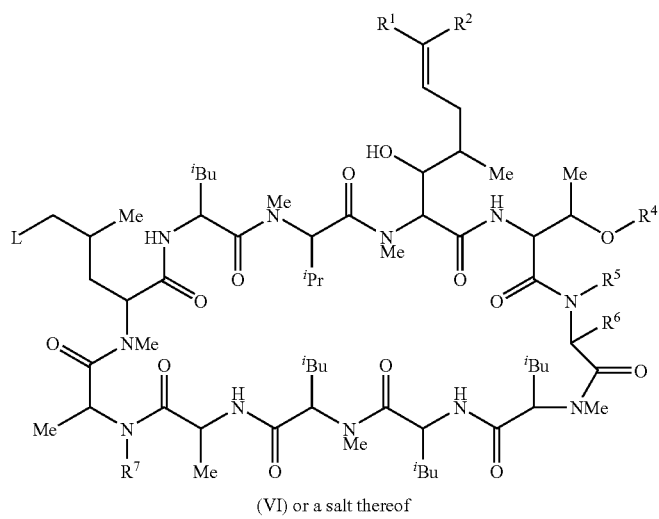
(VI) or a salt thereof
Process D
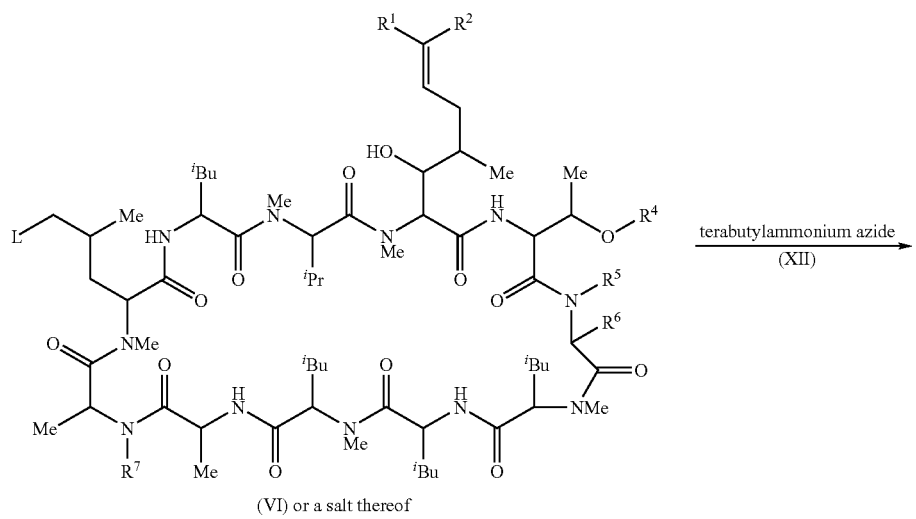
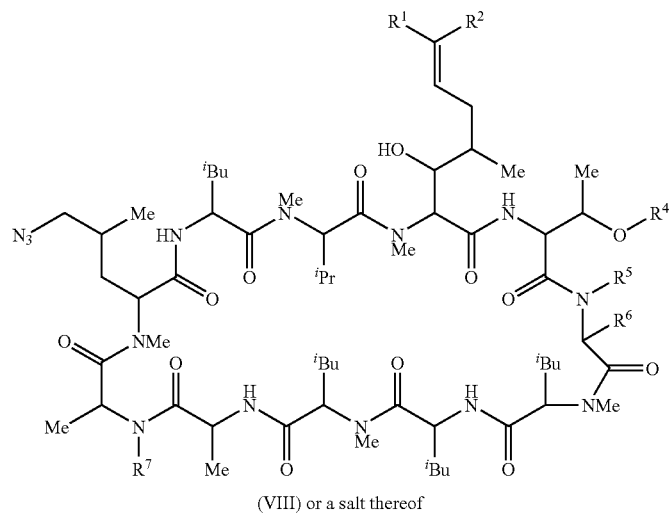
(VIII) or a salt thereof -continued
Process E
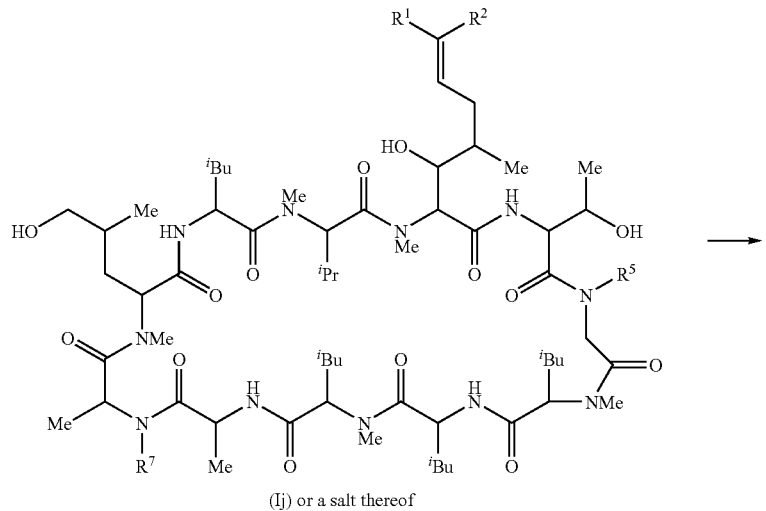
(Ij) or a salt thereof
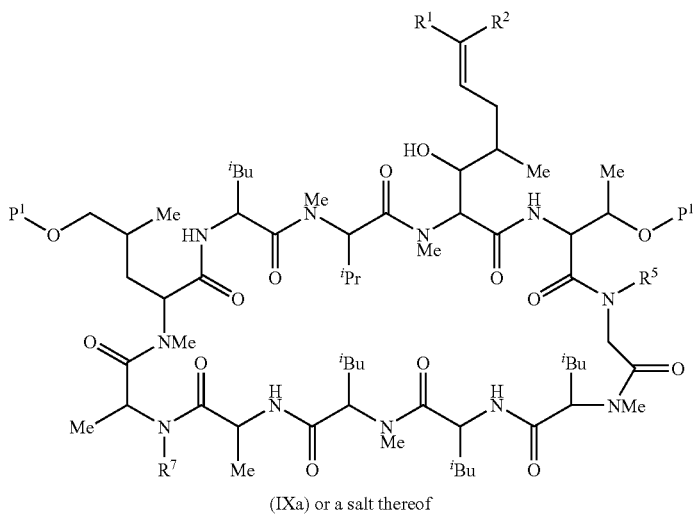
(IXa) or a salt thereof
Process F
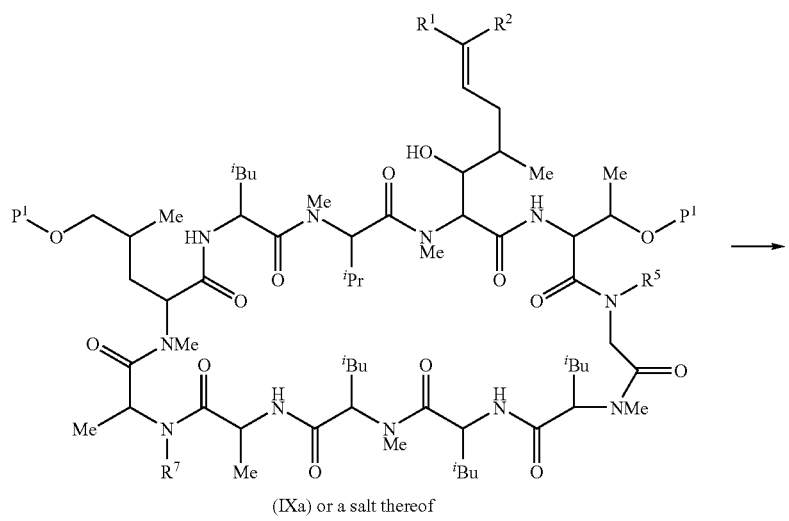
(IXa) or a salt thereof -continued
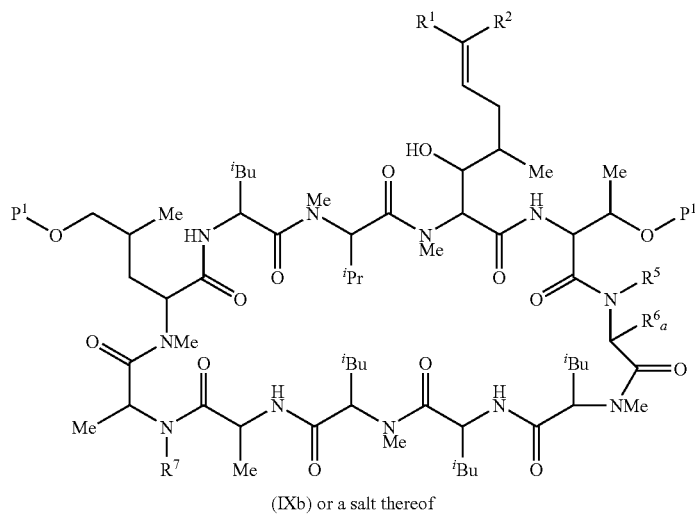
(IXb) or a salt thereof
Process G
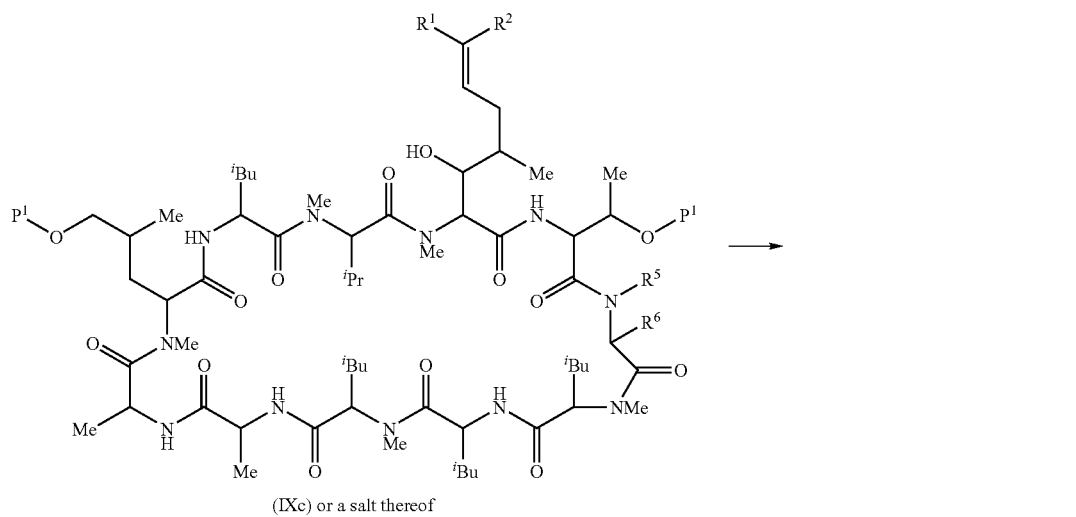
(IXc) or a salt thereof
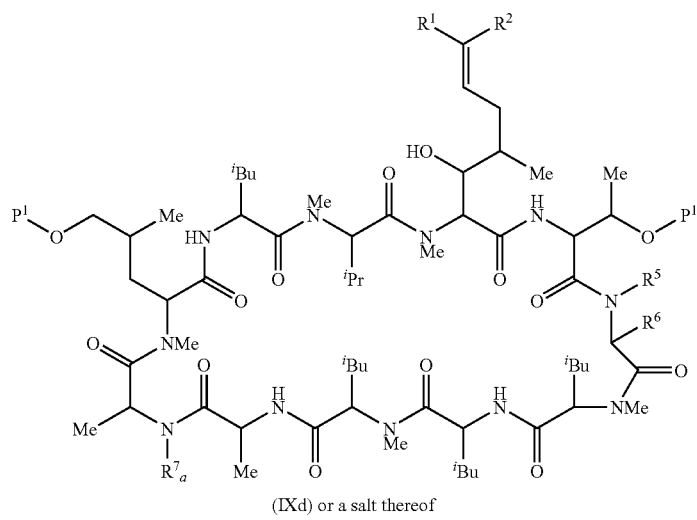
(IXd) or a salt thereof -continued
Process H
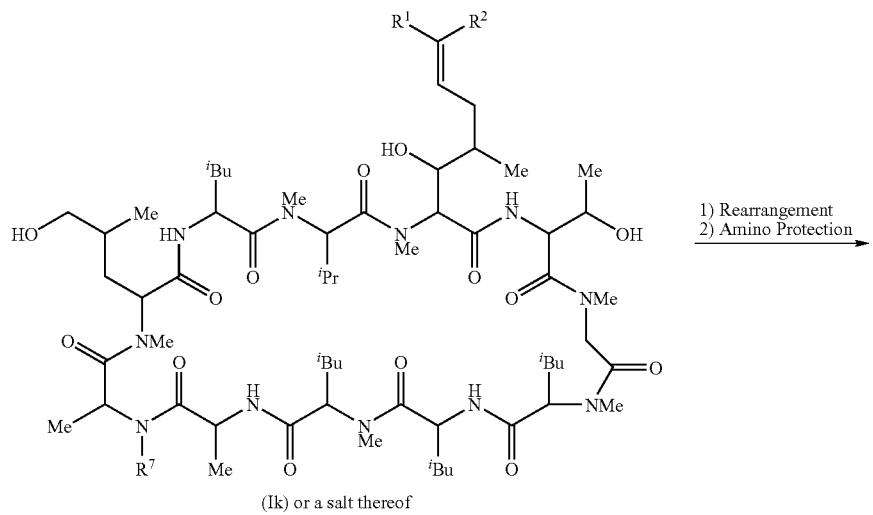
(Ik) or a salt thereof
1) Rearrangement
2) Amino Protection →
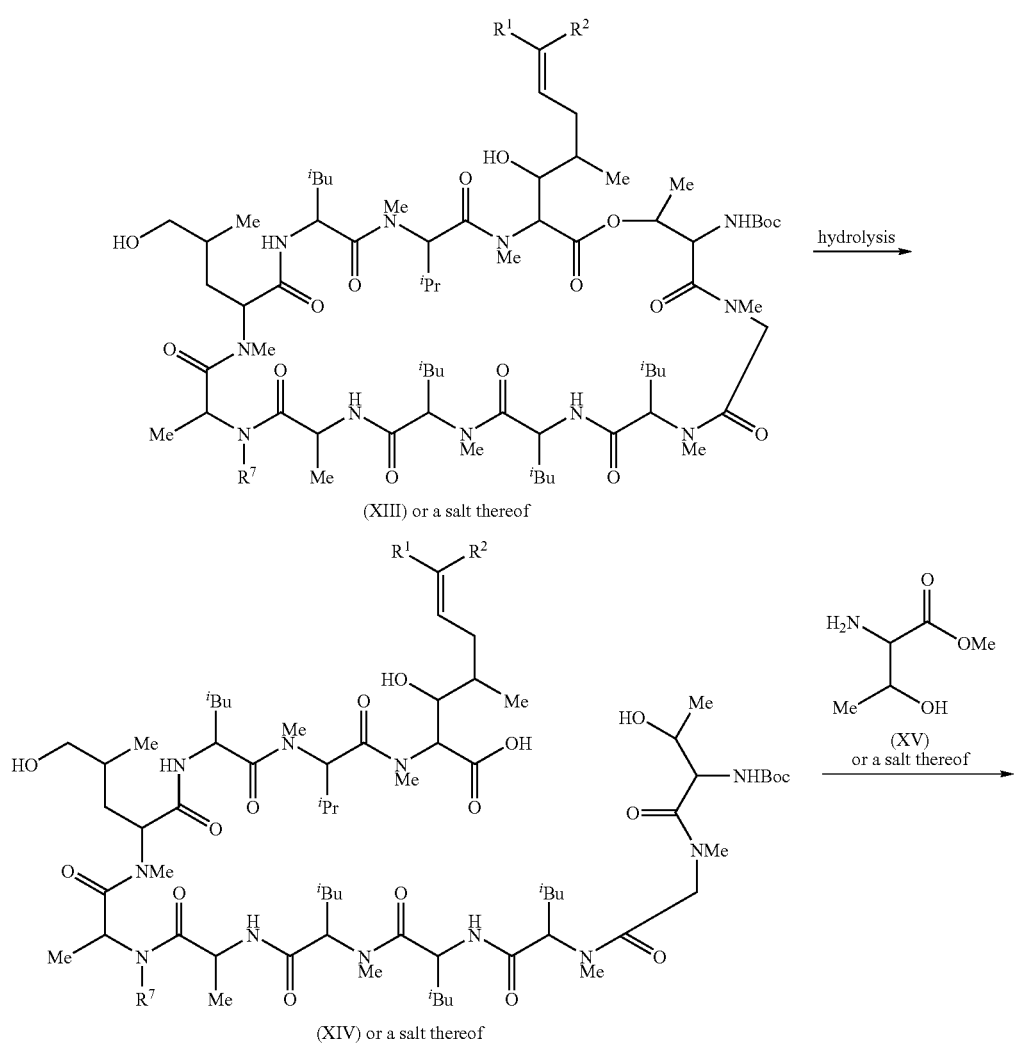
(XIII) or a salt thereof
hydrolysis →
(XIV) or a salt thereof
(XV) or a salt thereof →

-continued
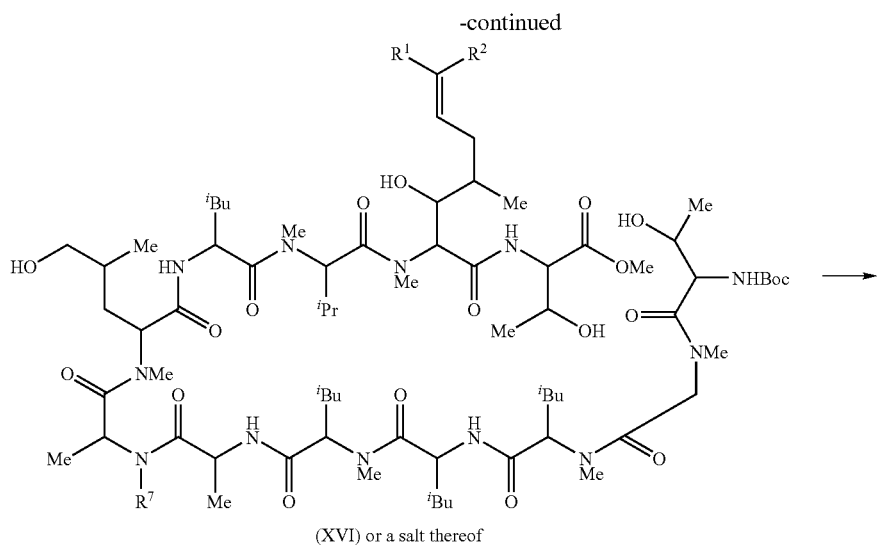
(XVI) or a salt thereof
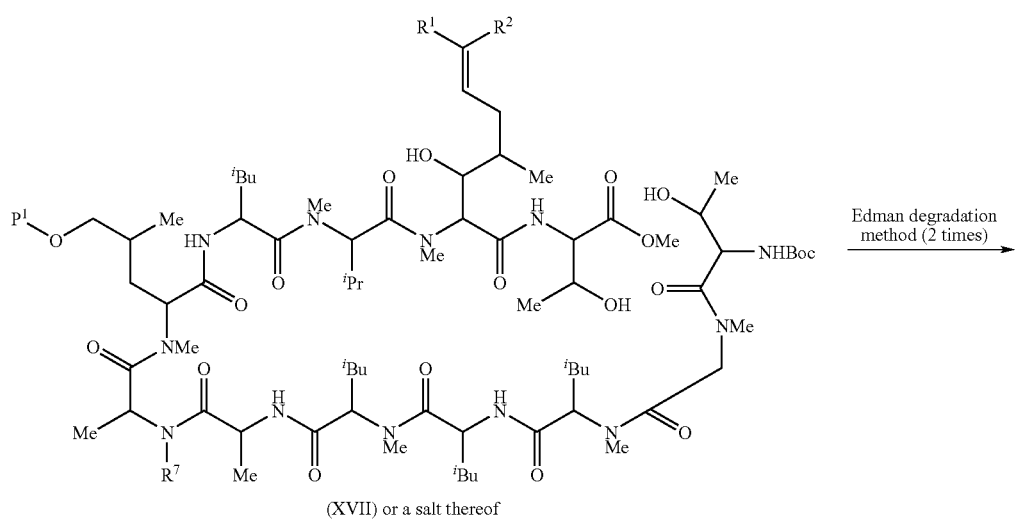
(XVII) or a salt thereof
Edman degradation method (2 times)
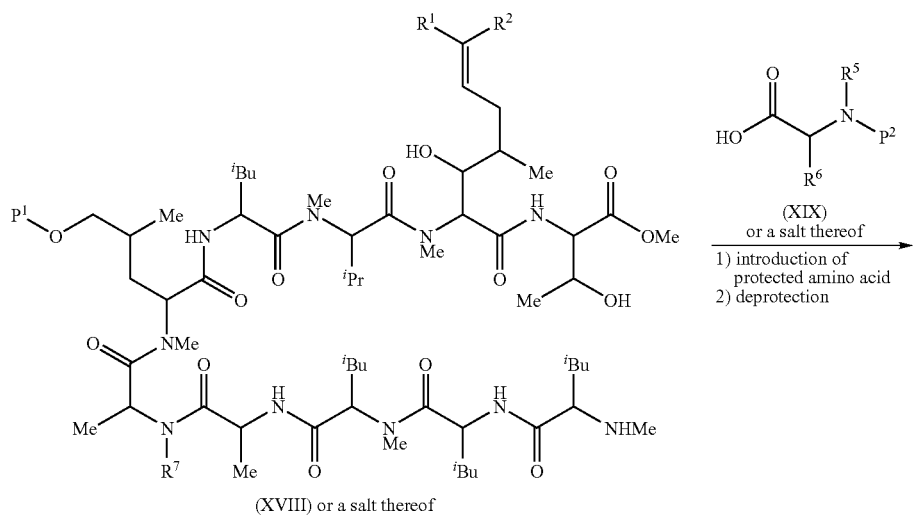
(XVIII) or a salt thereof
(XIX) or a salt thereof
1) introduction of protected amino acid
2) deprotection -continued

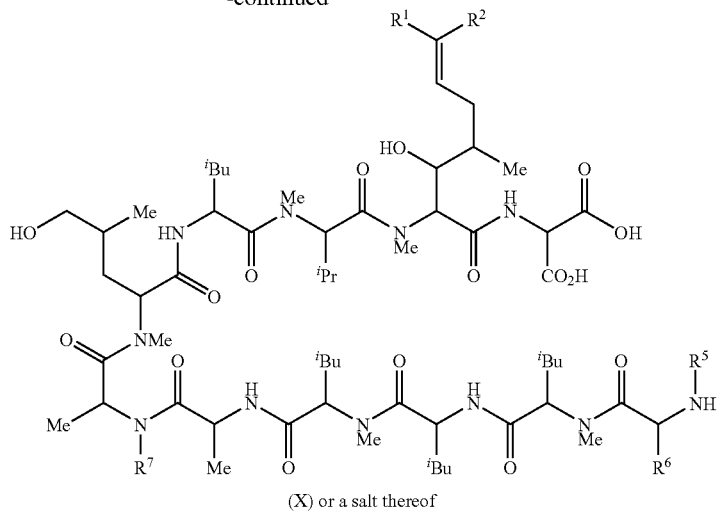

(X) or a salt thereof wherein
$R^1, R^2, R^3, R^4, R^5, R^6, R^7, R^8, R^9, R^{10}, R^{11}$, and $R^{13}$ are as defined above, and
L is a leaving group;
$R^6_a$ is the same as $R^6$ defined above except hydrogen;
$R^7_a$ is the same as $R^7$ defined above except hydrogen;
$P^1$ is a hydroxy protective group; and
$P^2$ is a amino protective group.

The processes for the preparation of the object compounds and starting compounds are described below.

Process 1

The compound (Ia) or a salt thereof can be prepared by reacting the compound (II) or a salt thereof with the compound (III) or a salt thereof.

The reaction is usually carried out in a conventional solvent such as tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

This reaction (especially when the compound (II) and/or (III) is a salt form) is usually carried out in the presence of an inorganic or an organic base. Suitable inorganic base may be an alkali metal [e.g., sodium or potassium], an alkali metal hydroxide [e.g., sodium hydroxide or potassium hydroxide], alkali metal hydrogen carbonate [e.g., sodium hydrogen carbonate or potassium hydrogen carbonate], alkali metal carbonate [e.g., sodium carbonate or potassium carbonate], alkaline earth metal carbonate [e.g., calcium carbonate or magnesium carbonate], alkali metal hydride [e.g., sodium hydride or potassium hydride], or the like. Suitable organic base may be tri(lower)alkylamine [e.g., triethylamine or N,N-diisopropylethylamine], alkyl magnesium bromide [e.g., methyl magnesium bromide or ethyl magnesium bromide], alkyl lithium [e.g., methyl lithium or butyl lithium], lithium diisopropylamide, lithium hexamethyldisilazido, or the like.

The reaction temperature is not critical, and the reaction is usually carried out under cooling to warming.

Process 2

The compound (Ic) or a salt thereof can be prepared by subjecting the compound (Ib) or a salt thereof to reduction.

Suitable method of the reduction is catalytic hydrogenation.

Suitable catalysts to be used in the catalytic hydrogenation are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, palladium hydroxide on carbon, colloidal palladium, palladium on barium sulfate, palladium on barium carbonate, etc.), and the like.

The hydrogenation is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process 3

The compound (Id) or a salt thereof can be prepared by subjecting the compound (IV) or a salt thereof to reductive amination reaction with the compound (V) or a salt thereof.

This reaction is usually carried out in the presence of a reducing agent such as sodium triacetoxyborohidride, or the like.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process 4

The compound (Ie) or a salt thereof can be prepared by reacting the compound (VI) or a salt thereof with the compound (VII) or a salt thereof.

L is leaving group. Examples of a leaving group include halogen, alkanesulfonyl optionally substituted by one or more halogen, arylsulfonyl and the like.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process 5

The compound (If) or a salt thereof can be prepared by subjecting the compound (VIII) or a salt thereof to reduction.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process 6

The compound (Ig) can be prepared by subjecting the compound (IX) to deprotection.

This reaction is carried out in accordance with a conventional method such as hydrolysis, reduction or the like.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process 7

This cyclization is carried out by the amidation of the compound (X) or a salt thereof.

This reaction is preferably carried out in the presence of condensing agent (including carbodiimide (e.g., N,N-diisopropylcarbodiimide, N,N'-dicyclohexylcarbodiimide, 1-[3-(dimethylamino)propyl]-3-ethylcarbodiimide, and the like), diphenylphosphinic azido, diphenylphosphonic chloride, or the like).

This reaction in the present reaction is usually carried out in the presence of an additive such as N-hydroxybenzotriazole (HOBt), 1-hydroxy-7-azabenzotriazole (HOAt), bis(2-oxo-3-oxazolydinyl)phosphinic chloride, and the like.

The reaction may be also be carried out in the presence of an organic or inorganic base such as an alkali metal bicarbonate, tri(lower)alkylamine, pyridine, N-(lower)alkylmorphorine, N,N-di(lower)alkylbenzylamine, or the like.

The reaction is usually carried out in a conventional solvent such as water, acetone, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof. The reaction temperature is not limited and the reaction is usually carried out under cooling to heating Process A The object compound (II) or a salt thereof can be prepared by reacting the compound (Ih) or a salt thereof with the compound (XI) or a salt thereof.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction may also be carried out in the presence of an inorganic or organic base such as alkali metal carbonate (e.g. potassium carbonate, etc.), alkali metal bicarbonate, tri(lower)alkylamine, pyridine, N-(lower)alkyl-morpholine, N,N-di(lower)alkylethylamine (e.g. N,N-diisopropylethylamine, etc.), N,N-di(lower)alkylbenzylamine, or the like.

The reaction temperature is not critical, and the reaction is usually carried out under cooling to heating.

Process B

The compound (IV) or a salt thereof can be prepared by subjecting the compound (Ii) to oxidation.

This reaction is usually carried out in a conventional solvent such as tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process C

The compound (VI) or a salt thereof can be prepared by subjecting the compound (Ii) or a salt thereof to introduction reaction of a leaving group.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process D

The compound (VIII) or a salt thereof can be prepared by the reaction of the compound (VI) or a salt thereof with the compound (XII) or a salt thereof.

This reaction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process E

The compound (IXa) or a salt thereof can be prepared by subjecting the compound (Ij) or a salt thereof to protection of hydroxyl reaction.

This reaction is usually carried out in a conventional solvent such as tetrahydrofuran, dioxane, toluene, methylene chloride, ethylene dichloride, chloroform, N,N-dimethylformamide, N,N-dimethylacetamide or any other organic solvent which does not adversely affect the reaction, or a mixture thereof.

The reaction temperature is not critical, and the reaction is usually carried out under cooling to warming.

Process F

The compound (IXb) or a salt thereof can be prepared by subjecting the compound (IXa) or a salt thereof to alkylation.

This reaction is usually carried out in a conventional solvent such as tetrahydrofuran, dioxane, toluene, diethyl ether, diisopropyl ether, cyclopentyl methyl ether or any other organic solvent which does not adversely affect the reaction, or a mixture thereof. The bases used in this process are such as Lithium diisopropylamide, Lithium hexamethyldisilazide, Sodium hexamethyldisilazide, Potassium hexamethyldisilazide, Sodium amide, Lithium amide, 2,2,4,4,-Tetramethyl piperidine lithium salt, n-butyl lithium, Lithium N-methylanilide.

The reaction temperature is not critical, and the reaction is usually carried out under cooling to warming.

Process G

The compound (IXc) or a salt thereof can be prepared by subjecting the compound (IXd) or a salt thereof to alkylation.

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, sec-butanol, amyl alcohol, diethyl ether, dioxane, tetrahydrofuran, dimethyl sulfoxide, or any other organic solvent which does not adversely affect the reaction, preferably in ones having strong polarities. Among the solvents, hydrophilic solvents may be used in a mixture with water.

The reaction is preferably conducted in the presence of a base, for example, inorganic base such as alkali metal hydroxide, alkali metal carbonate, alkali metal bicarbonate, alkali metal hydride (e.g. sodium hydride, etc.), organic base such as trialkylamine, and the like.

The reaction temperature is not critical, and the reaction is usually carried out at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.), di(lower)alkyl azodicarboxylate (e.g. diethyl azodicarboxylate, diisopropyl azodicarboxylate, etc.) or the like.

Process H

The compound (X) or a salt thereof can be prepared from the compound (Ik) or a salt thereof by the following processes.

a) Rearrangement

This reaction is the rearrangement of the compound (Ik).

The reaction is usually carried out in the presence of acid (such as trifluoroacetic acid, sulfuric acid, methanesulfonic acid, or the like).

The reaction is usually carried out in a conventional solvent such as water, acetone, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof.

The reaction temperature is not limited and the reaction is usually carried out under cooling to heating.

This reaction of the present invention, because of and owing to the substrate, can be carried out under the mild condition such as mild acid (p-toluenesulfonic acid) and mild temperature (ambient temperature to warming) to give a compound selectively subjected the rearrangement reaction.

b) Amino Protection

This reaction is protection of amino moiety, which goes out by the rearrangement reaction.

The reaction is usually carried out in a conventional solvent such as water, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof.

The reaction temperature is not limited and the reaction is usually carried out under cooling to heating.

c) Hydrolysis

The hydrolysis is preferably carried out in the presence of a base (including an inorganic base and organic base such as alkali metal (e.g., sodium, potassium, etc.), alkaline earth metal (e.g., magnesium, calcium, etc.), the hydroxide or carbonate or bicarbonate of alkali metal or alkaline earth metal, trialkylamine (e.g., trimethylamine, etc.), hydrazine, picoline, 1,5-diazabicyclo[4.3.0]non-5-ene, 1,8-diazabicyclo[5.4.0]undec-7-ene, or the like) or an acid (including an organic acid (e.g., formic acid, acetic acid, propanoic acid, trifluoroacetic acid, etc.), an inorganic acid (e.g., hydrobromic acid, sulfuric acid, hydrochloric acid, etc.) and Lewis acid (e.g., boron tribromide, aluminum chloride, titanium trichloride, etc.)).

The reaction is usually carried out in a conventional solvent such as water, alcohol (e.g., methanol, ethanol, isopropyl alcohol, etc.), tetrahydrofuran, dioxane, toluene, methylene chloride, chloroform, N,N-dimethylformamide, or any other organic solvent which does not adversely affect the reaction or the mixture thereof.

A liquid base or acid can be also used as the solvent.

The reaction temperature is not limited and the reaction is usually carried out under cooling to heating.

d) Reaction with (XV)

This reaction is the amidation of the compound (XIV) or a salt thereof with the compound (XV) or a salt thereof, so this reaction can be carried out in the manner as in the aforementioned Process 7, and therefore the reagents to be used and the reaction condition (e.g., solvent, reaction temperature, etc.) can be referred to those of Process 7.

e) Protection of Hydroxyl

The reaction is usually carried out in a conventional solvent such as water, acetonitrile, acetone, alcohol (e.g., methanol, ethanol, isopropyl alcohol, or the like), tetrahydrofuran, dioxane, toluene, methylene chloride, chloroform, ethyl acetate, N,N-dimethylformamide, or any other organic solvent which does not adversely affect the reaction or the mixture thereof.

The reaction temperature is not limited and the reaction is usually carried out under cooling to heating.

f) Edman Degradation Method

The reaction is usually carried out in a conventional solvent such as water, acetonitrile, acetone, alcohol (e.g., methanol, ethanol, isopropyl alcohol, or the like), tetrahydrofuran, dioxane, toluene, methylene chloride, chloroform, ethyl acetate, N,N-dimethylformamide, or any other organic solvent which does not adversely affect the reaction or the mixture thereof.

The reaction temperature is not limited and the reaction is usually carried out under cooling to heating.

And the reaction is carried out twice.

This reaction can be carried out by the similar manners described in the literature, e.g., M. K. Eberle et al., *J. Org. Chem.* 59, 7249-7258 (1994).

g) Reaction with (XIX)

This reaction is the amidation of the compound (XIX) or a salt thereof with the compound (XVII) or a salt thereof, so this reaction can be carried out in the same manner as in the aforementioned d), and therefore the reagents to be used and the reaction conditions (e.g., solvent, reaction temperature, etc.) can be referred to those of d).

h) Deprotection

This reaction is carried out in accordance with a conventional method such as hydrolysis, reduction or the like.

More specifically, the object compound can be prepared by the processes described in Examples in the present application or similar processes.

The compounds obtained by the above-mentioned processes 1-6 and A-H can be isolated and purified by a conventional method, such as pulverization, recrystallization, column chromatography, high performance liquid chromatography, reprecipitation and demineralized resin column chromatography.

Suitable salts of the object compound (I) are conventional pharmaceutically acceptable and non-toxic salts, and may be a salt with a base or an acid addition salt, for example, a salt with an inorganic base (such as an alkali metal salt, e.g. sodium salt, potassium salt, etc., an alkaline earth metal salt, e.g. calcium salt, magnesium salt, etc., an ammonium salt), a salt with an organic base (such as an organic amine salt, e.g. triethylamine salt, diisopropyl ethylamine salt, pyridine salt, picoline salt, ethanolamine salt, triethanolamine salt, dicyclohexylamine salt, N'N'-dibenzylethylenediamine salt, etc.), an inorganic acid addition salt (such as hydrochloride, hydrobromide, sulfate, phosphate, etc.), an organic carboxylic acid or sulfonic acid addition salt (such as formate, acetate, trifluoroacetate, maleate, tartrate, gluconate, fumarate, methanesulfonate, benzenesulfonate, toluenesulfonate, etc.), a salt with a basic or acidic amino acid (such as arginine, aspartic acid, glutamic acid, etc.) and the like.

In the above and subsequent descriptions of the present specification, suitable examples and illustrations of the various definitions to be included within the scope of the invention are explained in detail as follows.

The term "lower" is intended a group having 1 to 6, preferably 1 to 4 atom(s), unless otherwise indicated.

Suitable examples of "lower alkyl" and "lower alkyl" moiety may include a straight or branched one having 1 to 6 carbon atom(s), such as methyl, ethyl, propyl, isopropyl, butyl, isobutyl, sec-butyl, tert-butyl, pentyl, tert-pentyl, neopentyl, hexyl, isohexyl, and the like.

Suitable examples of "cyclo(lower)alkyl" may include cyclic alkyl having 3 to 6 carbon atom, such as cyclopropyl, cyclobutyl, cyclopentyl and cyclohexyl, and the like.

Suitable examples of "lower alkenyl" may include a straight or branched one having 2 to 6 carbon atoms, such as vinyl, 1- or 2-propenyl, isopropenyl, 1- or 2- or 3-butenyl, isobutenyl, sec-butenyl, tert-butenyl, pentenyl, tert-pentenyl, neopentenyl, hexenyl, isohexenyl, and the like.

Suitable examples of "cyclo(lower)alkenyl" may include cycloalkenyl having 3 to 6 carbon atoms, such as cyclopropenyl, cyclobutenyl, cyclopentenyl and cyclohexenyl, and the like.

Suitable examples of "aryl" and "aryl" moiety may include phenyl which may be substituted with lower alkyl (e.g., phenyl, mesityl, tolyl, etc.), naphthyl, anthryl, tetrahydronaphthyl, indenyl, tetrahydroindenyl, and the like.

Suitable examples of "halogen" means fluorine, chlorine, bromine and iodine.

A "heterocyclic group", as used herein, refers to both heteroaryl and heterocycloalkyl groups, and in other words, suitable examples of "heterocyclic group" may be saturated or unsaturated, monocyclic or polycyclic one containing at least one hetero atom such as nitrogen atom, oxygen atom or sulfur atom, for example, which may include:

unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), azepinyl, etc.;

saturated 3 to 8-membered (more preferably 5 or 6-membered) heteromonocyclic group containing 1 to 4 nitrogen atom(s), for example, aziridinyl, azetidinyl, pyrrolidinyl, imidazolidinyl, piperidyl, piperazinyl, 2,5-methanopiperazinyl, hexahydroazepinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, tetrahydroquinolyl, tetrahydroisoquinolyl, tetrahydroindolyl, dihydroindazolyl, dihydroimidazopyrazinyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated condensed heterocyclic group containing 1 or 2 oxygen atom(s) and 1 to 3 nitrogen atom(s), for example, benzoxazolyl, benzoxadiazolyl, dihydropyridooxazinyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example thiazolidinyl, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, dihydrothiazolopyridinyl, etc.;

unsaturated 3 to 8-membered (more preferably 5 or 6-membered) heteromonocyclic group containing an oxygen atom, for example, furyl etc.;

saturated 3 to 8-membered (more preferably 5 or 6-membered) heteromonocyclic group containing 1 or 2 oxygen atom(s), for example, oxiranyl, 1,3-dioxolanyl, tetrahydrofuranyl, tetrahydropyranyl, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example benzothienyl, benzodithiinyl, etc.;

unsaturated condensed heterocyclic group containing an oxygen atom and 1 or 2 sulfur atom(s), for example, benzoxathiinyl, etc.;

saturated condensed heteromonocyclic group containing 1 to 3 nitrogen atom(s), for example, tetrahydropyridopyrrolidinyl, etc.;

and the like.

Suitable "heteroaryl" can be referred to the ones as mentioned above, wherein the heterocyclic group has aromatic ring systems.

Suitable "N-containing heterocyclic group" can be referred to the ones as mentioned above, wherein the heterocyclic group is containing at least one nitrogen atom in its ring members, such as pyrrolidinyl, piperidyl, piperazinyl, morpholinyl, thiazolyl, oxazolyl, and the like.

Suitable examples of "suitable substituent(s)" may include hydroxy, lower alkyl, -(lower alkyl)-O-(lower alkyl), —S(═O)$_2$-(lower alkyl), —C(═O)NH$_2$, cyclo(lower)alkyl, —O-(lower alkyl), halogen, amino, aryl, heterocyclic group, aryl(lower)alkyl, acyl, and the like, and each of which may have one or more suitable substituent(s) again.

Suitable examples of "acyl" may include lower alkanoyl, lower alkenoyl, cyclo(lower)alkenylcarbonyl, aroyl, heterocycliccarbonyl, heterocyclic(lower)alkanoyl, heterocyclic (lower)alkenoyl, lower alkylsulfinyl, lower alkenylsulfinyl, arylsulfinyl, heterocyclic sulfinyl, lower alkylsulfonyl, lower alkenylsulfonyl, arylsulfonyl, heterocyclic sulfonyl, carboxy, protected carboxy, and the like.

Suitable examples of aforesaid "lower alkanoyl" may be formyl, acetyl, propionyl, butyryl, isobutyryl, pivaloyl, hexanoyl, and the like.

Suitable aforesaid "lower alkenoyl" may be acryloyl, methacryloyl, crotonoyl, cynnamoyl, and the like.

Suitable aforesaid "aroyl" may be benzoyl, toluoyl, naphthoyl, and the like.

Suitable examples of aforesaid "protected carboxy" may be;
i) esterified carboxy, in which suitable esterified carboxy may include —O-(lower alkyl)-carbonyl (e.g. methoxycarbonyl, ethoxycarbonyl, propoxycarbonyl, butoxycarbonyl, t-butoxycarbonyl, pentyloxycarbonyl, hexyloxycarbonyl, etc.), aryl-O-(lower alkyl)-carbonyl (e.g. benzyloxycarbonyl, phenethyloxycarbonyl, 2-phenylpropoxycarbonyl, 4-phenylbutoxycarbonyl, 4-phenylpentyloxycarbonyl, 1,3-diphenylhexyloxycarbonyl, etc.), and the like;
ii) amidated carboxy, in which suitable amidated carboxy may include carbamoyl, N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.), N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc.), N-lower alkyl-N-ar(lower)alkylcarbamoyl (e.g. N-methyl-N-benzylcarbamoyl, etc), and the like.

The "heterocyclic" moiety in the aforesaid heterocycliccarbonyl, heterocyclic(lower)alkanoyl, heterocyclic(lower) alkenoyl, heterocyclic sulfinyl, and heterocyclic sulfonyl, may include carbonyl group substituted by heterocyclic group as mentioned above such as morpholinylcarbonyl, piperidylcarbonyl, piperazinylcarbonyl, imidazolylcarbonyl, pyrazolylcarbonyl, pyrrolidinylcarbonyl, pyrazinylcarbonyl, nicotinoyl, isonicotinoyl, furoyl, thenoyl, and the like.

V. Lohmann et al., *Science* 285, 110-113 (1999) reported that they prepared human hepatoma cell lines (Huh-7) in which subgenomic HCV RNA molecules were introduced, and found that subgenomic HCV RNA was replicated in the cells at a high rate. It is thought that the replication mechanism of the subgenomic HCV RNA in these cell lines is extremely similar to the replication of full length HCV RNA genome in hepatic cells infected with HCV. Hence, the method for evaluating the activity of the compound (I) for inhibiting RNA replication in accordance with the present invention is based on the cellular assay method that uses Huh-7 cells in which subgenomic HCV RNA is introduced.

In order to show the usefulness of the compound (I) or a salt thereof in the present invention, a pharmacological test example of a representative compound in the present application is shown as follows.

Test Example

HCV Replicon Reporter Assay

The inhibitory activity of the test compounds against the replication of HCV replicon was evaluated by quantifying the activity of luciferase, a reporter gene product encoded in the replicon system reported by Yokota et al., *EMBO J* 4: 602-608 (2003). The enzyme assay was carried out according to the technical manual of the Steady-Glo(trade mark) luciferase assay system (Promega). The replicon assay was carried out with the modified method reported by Lohmann et al., *Science* 285: 110 (1999). The details are described in the following.

1) Addition of Agent to Cells $6 \times 10^3$ HCV replicon cells in D-MEM medium containing 5% fetal bovine serum were seeded in each well of a 96-well microtiter plate (Corning Inc.). After the cells were incubated at 37° C. for 16 hours in 5% $CO_2$, the test compound was added.

2) Luciferase Assay Procedure

After cultivation for two more days, the culture medium was removed and 25 µl of Glo Lysis buffer was added to each well and incubated for 5 minutes. Allowing lysis to occur, 25 µl of Steady-Glo(trade mark) assay reagent was added to each well. After incubation for 5 minutes, the luminescence was measured with a luminometer, Mithras LB940 (BERTHOLD TECHNOLOGIES GmbH & Co.KG) following the manufacturer's instructions.

Test Result

The luciferase activities in replicon cells treated at each concentrations of the compound were employed for the calculation of $EC_{50}$ value of the each compound, which gave the compound concentration indicating 50% enzyme activity level to the control (no drug group, containing only DMSO).

| Test compound:<br>Object compound of Example No. | HCV replicon replication<br>inhibitory activity:<br>$EC_{50}$ (µg/ml) |
|---|---|
| 1 | 0.15 |
| 8 | 0.16 |
| 10 | 0.18 |
| 36 | 0.09 |
| 39 | 0.12 |
| 84 | 0.053 |
| 102 | 0.053 |
| 124 | 0.056 |
| 125 | 0.06 |
| 130 | 0.031 |
| 145 | 0.022 |
| 151 | 0.035 |
| 176 | 0.032 |
| 183 | 0.08 |
| 186 | 0.03 |
| 191 | 0.023 |
| 203 | 0.026 |
| 221 | 0.039 |
| 228 | 0.046 |
| 232 | 0.074 |
| 235 | 0.039 |

-continued

| Test compound: Object compound of Example No. | HCV replicon replication inhibitory activity: $EC_{50}$ (μg/ml) |
|---|---|
| 249 | 0.07 |
| 264 | 0.11 |

From the result of the above-mentioned test example, it is realized that the compound (I) or a salt thereof of the present invention possesses an anti-hepatitis C virus activity.

Some of the present invention compounds showed HCV replicon replication inhibitory activity in human serum (instead of fetal bovine serum), too.

In addition, Some of the present invention compounds showed preferable pharmacokinetic profile.

The anti-HCV agent in the present invention, containing the compound (I) or a salt thereof as an active ingredient, can be used in the form of a pharmaceutical preparation, for example, in a solid, semisolid or liquid form, in admixture with an organic or inorganic carrier or excipient suitable for oral; sublingual; buccal; nasal; respiratory; parenteral (intracutaneous, intraorgan, subcutaneous, intradermal, intramuscular, intra-articular, central-venous, hepatic-venous, peripheral-venous, lymphatic, cardiovascular, arterial, ocular including injection around eye or intravenous drip around eye); intravenous drip into eyeball, augen structure or augen layer; aural including auditory canal, papillary chamber, external and internal auditory canals, drum membrane, tympanum, internal-auditory including spiralis cochleae ganglion, labyrinth, etc.; intestinal; rectal; vaginal; ureteral; and vesical administration. With respect to intrauterine and perinatal adaptation diseases, parenteral administration is preferable since administration is carried out in maternal blood vessels, or in vacancies, such as maternal organs including uterus, uterine cervix and vagina; fetal embryo, fetus, neonate, and combination tissue; and amnion, umbilical cord, umbilical artery and vein; placenta, and the like. Use of these passages is changed depending on the condition of each patient.

The compound (I) or a salt thereof can be administered independently as a therapeutic agent or may be desired to be used as part of prescribed drugs. The "anti-HCV agent" in accordance with the present invention can be used in the form of a pharmaceutical preparation, for example, in a solid, semisolid or liquid form, in admixture with at least one or some suitable organic or inorganic carriers or excipients, or other pharmacological therapeutic agents. The active ingredient can be compounded with, for example, usual pharmacologically acceptable and non-toxic carriers in a solid form, such as granules, tablets, pellets, troches, capsules or suppositories; creams; ointments: aerosols; powders for insufflation; in a liquid form, such as solutions, emulsions or suspensions for injection; oral ingestion; eye drops; and any other forms suitable for use. And, if necessary, there may be included in the above preparations auxiliary substances, such as stabilizing, thickening, wetting, hardening and coloring agents; perfumes or buffers; or any other additives used commonly.

The compound (I) or a pharmaceutically acceptable salt thereof is/are included in the pharmaceutical composition in an amount sufficient to produce the desired anti-hepatitis C effect upon the process or condition of diseases.

The combination use of IFN and/or ribavirin with the compound (I) or a salt thereof is effective against hepatitis C.

For applying the composition to humans, it is preferable to apply it by intravenous, intramuscular, pulmonary, oral administration, eye drop administration or insufflation. While the dosage of therapeutically effective amount of the compound (I) varies from and also depends upon the age and condition of each individual patient to be treated, in the case of intravenous administration, a daily dose of 0.001-400 mg of the compound (I) per kg weight of human being in the case of intramuscular administration, a daily dose of 0.1-20 mg of the compound (I) per kg weight of human being, in case of oral administration, a daily dose of 0.5-50 mg of the compound (I) per kg weight of human being is generally given for treating or preventing hepatitis C. However, these doses may be required to exceed the limit thereof to obtain therapeutic results.

The amount of the lipopeptide compound (I) or its pharmaceutically acceptable salt contained in the composition for a single unit dosage of the present invention is 0.1 to 400 mg, more preferably 1 to 200 mg, still more preferably 5 to 100 mg, specifically 5, 10, 15, 20, 25, 30, 35, 40, 45, 50, 55, 60, 65, 70, 75, 80, 85, 90, 95 and 100 mg.

The present invention may include an article of manufacture, comprising packaging material and the compound (I) identified in the above contained within said packaging material, wherein said the compound (I) is therapeutically effective for preventing or treating hepatitis C, and wherein said packaging material comprises a label or a written material which indicates that said compound (I) can or should be used for preventing or treating hepatitis C.

And the present invention may include a commercial package comprising the pharmaceutical composition containing the compound (I) identified in the above and a written matter associated therewith, wherein the written matter states that the compound (I) can or should be used for preventing or treating hepatitis C.

It is to be noted that the compound (I) or a salt thereof may include one or more stereoisomer(s), such as optical isomer(s) and geometrical isomer(s), due to asymmetric carbon atom(s) and double bond(s), and that all such isomers and the mixture thereof are included within the scope of the present invention.

The compound (I) or a salt thereof may include solvated compound (e.g. hydrate, ethanolate, etc.).

The compound (I) or a salt thereof may include both the crystal form and non-crystal form.

The compound (I) or a salt thereof may include the prodrug form.

The patent specifications and publications cited herein are incorporated in this specification by reference.

The following Preparations and Examples are given for the purpose of illustrating the present invention. However, the present invention is not limited to these Preparations and Examples.

The Starting Compounds used and the Object Compounds obtained in the following Examples 1 to 265 are given as mentioned below.

The abbreviations, symbols and terms used in the Preparations, Examples, and Formulae in the above and subsequent descriptions of the present specification (including the tables) have the following meanings.

$CH_2Cl_2$ Methylene chloride
$CHCl_3$ Chloroform
$Boc_2O$ di-tert-Butyl dicarbonate
DIPEA N,N-Diisopropylethylamine
DMAP N,N-Dimethylaminopyridine
DMF N,N-Dimethylformamide
DMSO Dimethyl sulfoxide
$Et_2O$ Diethyl ether
EtI Ethyl iodide EtOAc Ethyl acetate
EtOH Ethanol
Ex Example number
H₂O Water
HCl Hydrochloric acid
HOAt 1-Hydroxy-7-azabenzotriazole
KH₂PO₄ Potassium hydrogenphosphate
MeCN Acetonitrile
MeI Methyl iodide
MeOH Methanol
MgSO₄ Anhydrous Magnesium sulfate
NaH Sodium hydride
NaHCO₃ Sodium bicarbonate
NaOH Sodium hydroxide
PPh₃ Triphenylphosphine
Pd/C Palladium on Carbon
Prep Preparation number
TEA Triethylamine
THF Tetrahydrofuran
WSC 1-(3-Dimethylaminopropyl)-3-ethylcarbodiimide
Ac Acetyl
Bn Benzyl
Boc tert-Butoxycarbonyl
$^n$Bu n-Butyl
$^i$Bu Isobutyl
$^t$Bu tert-Butyl
Cy. Cyclo
Et Ethyl
Fmoc 9H-Fluoren-9-ylmethoxycarbonyl
Hex Hexyl
Hexe Hexenyl
Imi Imidazolyl
Me Methyl
Mor Morpholinyl
Pente Pentenyl
Ph Phenyl
Pip Piperidyl
Pipa Piperazinyl
$^i$Pr Isopropyl
$^n$Pr propyl
Py Pyridyl
Pyr Pyrazolyl
aq. aqueous
sat. saturated
Prep. Preparation number
MS Mass spectrometry data Prep 1

The compound (A) or a salt thereof can be produced from the compound (B) or a salt thereof according to the method described in International Publication WO 2006/054801 (compound (A) or a salt thereof with an enzyme, which can be obtained by fermentation of an enzyme-producing strain of microorganism belonging to the genus *Lentzea* sp. deposit number FERM BP-10079), and the compound (B) or a salt thereof can be produced by fermentation of fungus (Stachybotrys chartarum No. 19392: deposit number FERM BP-3364) according to the method described in Japanese Laid-open Patent Application Hei 5-271267, for example. Both microorganisms have been deposited at the International Patent Organism Depositary (IPOD) National Institute of Advanced Industrial Science and Technology, AIST Tsukuba Central 6, 1-1, Higashi 1-chome, Tsukuba-shi, IBARAKI, 305-8566, JAPAN.

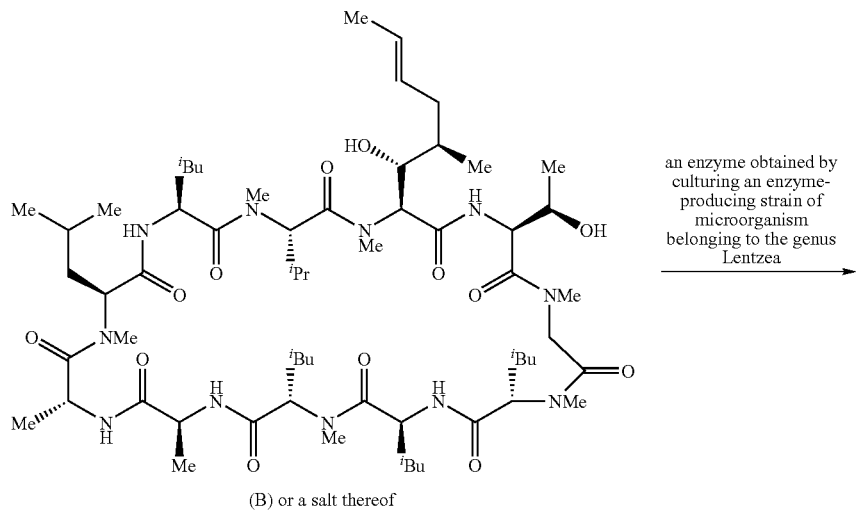

(B) or a salt thereof an enzyme obtained by culturing an enzyme-producing strain of microorganism belonging to the genus Lentzea
⟶

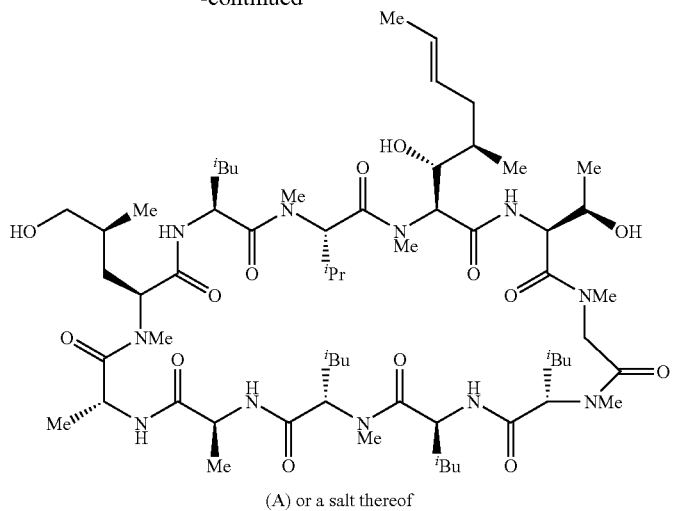

(A) or a salt thereof

Prep 2

To a solution of the compound (A) (500 mg) in CH$_2$Cl$_2$ (25 ml) were added 4-nitrophenyl chloroformate (98 mg) and N-methylmorpholine (89 μl). After the mixture was stirred for overnight, three further portions of 4-nitrophenyl chloroformate (98 mg) and N-methylmorpholine (89 μl) were added at intervals of 1 hour. After the starting compound was consumed, the mixture was diluted with EtOAc, washed with 1 N aq. HCl and aq. NaHCO$_3$ solution, dried over MgSO$_4$ and concentrated. The residue was chromatographed on silica gel (n-hexane:EtOAc=1:4 and then CH$_2$Cl$_2$:MeOH=9:1) to give 30 mg of the object minor compound (Prep 2-B) and 438 mg of the object major compound (Prep 2-A).

Minor Compound
  MS: 1564.51
Major Compound
  MS: 1399.25

Prep 3

To a solution of (3R,5R)-1-benzyl-3,5-dimethylpiperazine (810 mg) in CH$_2$Cl$_2$ (20 ml) and 1 N NaOH (8 ml) was added Boc$_2$O (865 mg), and the mixture was stirred at room temperature for 3 hours. The organic phase was separated, dried over MgSO$_4$ and concentrated. The residue was chromatographed on silica gel (n-hexane:EtOAc=9:1) to give tert-butyl (2R,6R)-4-benzyl-2,6-dimethyl-1-piperazinecarboxylate (930 mg).

NMR: 1.29 (6H, d, J=6.4 Hz), 1.46 (9H, s), 2.10-2.60 (4H, m), 3.30-4.10 (4H, m), 7.10-7.40 (5H, m).
MS: 305.4

Prep 4

A solution of the object compound of Prep 3 (930 mg) in MeOH was hydrogenated over 10% Pd/C (50% wet; 180 mg) for 2 hours. The mixture was filtered and the filtrate was concentrated. To a solution of the residue in CH$_2$Cl$_2$ (10 ml) and MeOH (2 ml) were added 37% formaldehyde aqueous solution (0.2 ml) and sodium triacetoxyborohydride (1.94 g) in sequence and the mixture was stirred at room temperature for 1 hour. The reaction was quenched with aq. NaHCO$_3$ solution and extracted with CH$_2$Cl$_2$ twice. The combined extracts were dried over MgSO$_4$ and concentrated. The residue was chromatographed on silica gel (n-hexane:EtOAc=8:1 to 0:100) to give tert-butyl (2R,6R)-2,4,6-trimethyl-1-piperazinecarboxylate (460 mg).

NMR: 1.32 (6H, d, J=6.5 Hz), 1.49 (9H, s), 2.10-2.60 (7H, m), 3.89 (2H, m).
MS: 229.3

Prep 5

To a solution of the object compound of Prep 4 (440 mg) in EtOAc (5 ml) was added dropwise 4 N hydrogen chloride in EtOAc (5 ml) and the mixture was stirred at room temperature for overnight. The resulting powder was collected, washed with CH$_2$Cl$_2$ and dried in vacuo to give (3R,5R)-1,3,5-trimethylpiperazine dihydrochloride (375 mg).

NMR (DMSO-d$_6$): 1.00-1.70 (6H, m), 2.77 (3H, s), 2.80-4.20 (6H, m), 9.83 (1H, brs), 10.20 (1H, brs).
MS (free): 129.4

Prep 6

To a solution of 2,6-cis-dimethylpiperazine (3 g) in CH$_2$Cl$_2$ (15 ml) were added TEA (3.7 ml) and Boc$_2$O (5.73 g) under ice-cooling, and the mixture was stirred at this temperature for 2 hours. It was then treated with H$_2$O and extracted with CH$_2$Cl$_2$ three times. The combined extracts were dried over MgSO$_4$ and concentrated. The residue was chromatographed on silica gel (CH$_2$Cl$_2$:acetone=1:1 to 2:3) to give tert-butyl cis-3,5-dimethyl-1-piperazinecarboxylate (5.47 g).

NMR: 1.06 (6H, d, J=6.2 Hz), 1.46 (9H, s), 2.20-4.30 (6H, m).

Prep 7

To a solution of the object compound of Prep 6 (5.43 g) in CH$_2$Cl$_2$ (55 ml) were added benzaldehyde (3.09 ml) and sodium triacetoxyborohydride (16.11 g) in sequence, and the mixture was stirred at room temperature for overnight. It was then treated with sat. aq. NaHCO$_3$ solution and extracted with CH$_2$Cl$_2$ twice. The combined extracts were dried over MgSO$_4$ and concentrated. The residue was chromatographed on silica gel (n-hexane:EtOAc=19:1 to 4:1) to give tert-butyl cis-4-benzyl-3,5-dimethyl-1-piperazinecarboxylate (7.30 g).

NMR: 1.08 (6H, d, J=4.5 Hz), 1.44 (9H, s), 2.30-3.00 (4H, m), 3.70-4.10 (4H, m), 7.10-7.60 (5H, m).
MS: 305.4

Prep 8

To a solution of the object compound of Prep 7 (7.25 g) in EtOAc (25 ml) was added dropwise 4 N hydrogen chloride in EtOAc (25 ml), and the mixture was stirred at room temperature for overnight. It was concentrated, coevaporated with MeOH and triturated with acetone. The resulting powder was collected, washed with acetone and dried in vacuo to give cis-1-benzyl-2,6-dimethylpiperazine dihydrochloride (4.48 g).

NMR (DMSO-$d_6$): 1.20-4.80 (14H, m), 7.30-7.80 (5H, m).
MS (free): 205.3

Prep 9

To a solution of the object compound of Prep 8 (1.89 g) in a mixed solvent of $CH_2Cl_2$ (20 ml) and MeOH (5 ml) were added DIPEA (4.75 ml), 35% formaldehyde aqueous solution (0.6 ml) and sodium triacetoxyborohydride (4.34 g) in sequence, and the mixture was stirred at room temperature for 2 hours. The mixture was basified with sat. aq. $NaHCO_3$ solution and extracted with $CH_2Cl_2$ four times. The combined extracts were dried over $MgSO_4$ and concentrated. The residue was chromatographed on silica gel ($CH_2Cl_2$:MeOH=97.5:2.5) to give cis-1-benzyl-2,4,6-trimethyl-piperazine (0.98 g).

NMR: 1.04 (6H, d, J=6.0 Hz), 1.80-2.90 (9H, m), 3.83 (2H, s), 7.10-7.50 (5H, m).
MS: 219.4

Prep 10

A solution of the object compound of Prep 9 (940 mg) in MeOH was hydrogenated over 10% Pd/C (50% wet) for 2 hours. The mixture was filtered and concentrated. The residue was dissolved in $CH_2Cl_2$, treated with 4 N hydrogen chloride in EtOAc (4 ml) and concentrated to give cis-1,3,5-trimethylpiperazine dihydrochloride (870 mg).

$^1$H NMR (DMSO-$d_6$, δ): 1.32 (6H, d, J=6.5 Hz), 2.79 (3H, s), 2.80-4.40 (6H, m).
MS (free): 129.4

Prep 11

To a solution of 4-nitropyrrazole (2.0 g) in DMF was added NaH (60% dispersion in oil) under ice cooling. After stirring at the same temperature for 10 minutes, 2-bromoethyl methyl ether (2.00 ml) and NaI (2.92 g) was added. The mixture was then stirred at room temperature for 3 hours, quenched by phosphate buffer solution (pH=7) and extracted with EtOAc. The extract was washed with $H_2O$ and brine, dried over $MgSO_4$, and evaporated in vacuo. The residue was purified by column chromatography on silica gel to give 1-(2-methoxyethyl)-4-nitro-1H-pyrazole (2.15 g).

NMR: 3.36 (3H, s), 3.75 (3H, t, J=2.5 Hz), 4.32 (3H, t, J=2.5 Hz), 8.07 (1H, s), 8.23 (1H, s).

Prep 12

4-[2-(4-Nitro-1H-pyrazol-1-yl)ethyl]morpholine was prepared according to a similar manner to that of Prep 11.

NMR: 2.40-2.55 (4H, m), 2.82 (2H, t, J=6.0 Hz), 3.60-3.80 (4H, m), 4.26 (2H, t, J=6.0 Hz), 8.06 (1H, s), 8.27 (1H, s).

Prep 13

A solution of the object compound of Prep 11 (2.14 g) in MeOH and THF was hydrogenated over 20% Pd/C (50% wet; 1.1 g) under 3 atm of hydrogen atmosphere at 50 degrees for 1.5 hours. The mixture was filtered. To the filtrate was added $Boc_2O$ (2.87 g) and it was stirred at room temperature for 2 hours. Solvent was evaporated and the residue was chromatographed on silica gel to give tert-butyl [1-(2-methoxyethyl)-1H-pyrazol-4-yl]carbamate (2.97 g).

NMR: 1.50 (9H, s), 3.33 (3H, s), 3.72 (2H, t, J=5.3 Hz), 4.22 (2H, t, J=5.3 Hz), 6.10-6.40 (1H, br), 7.35 (1H, s), 7.69 (1H, br-s).

Prep 14 tert-Butyl {1-[2-(4-morpholinyl)ethyl]-1H-pyrazol-4-yl}-carbamate was prepared according to a similar manner to that of Prep 13.

NMR: 1.50 (9H, s), 2.40-2.55 (4H, m), 2.81 (2H, t, J=6.8 Hz), 3.65-3.75 (4H, m), 4.19 (2H, t, J=6.8 Hz), 6.25 (1H, br-s), 7.32 (1H, s), 7.69 (1H, br-s).

Prep 15

To a solution of the object compound of Prep 13 (1.33 g) in DMF was added NaH (60% dispersion in oil; 223 mg) under ice cooling. After stirring at the same temperature for 10 minutes, MeI (0.45 ml) was added dropwise. The mixture was then stirred at room temperature for 3 hours, quenched by phosphate buffer solution (pH=7) and extracted with EtOAc. The extract was washed with $H_2O$ and brine, dried over $MgSO_4$, and evaporated in vacuo. The residue was purified by column chromatography on silica gel to give tert-butyl [1-(2-methoxyethyl)-1H-pyrazol-4-yl]methylcarbamate (2.98 g).

NMR: 1.52 (9H, s), 3.21 (3H, s), 3.34 (3H, s), 3.73 (2H, t, J=5.4 Hz), 4.23 (2H, t, J=5.4 Hz), 7.44 (1H, br-s). 7.50-8.00 (1H, br).

Prep 16 tert-Butyl methyl{1-[2-(4-morpholinyl)ethyl]-1H-pyrazol-4-yl}carbamate was prepared according to a similar manner to that of Prep 15.

NMR: 1.52 (9H, s), 2.45-2.55 (4H, m), 2.82 (2H, t, J=6.8 Hz), 3.21 (3H, s), 3.65-3.75 (4H, m), 4.20 (2H, t, J=6.8 Hz), 7.41 (1H, s), 7.45-7.95 (1H, br).

Prep 17

To a solution of the object compound of Prep 15 (1.18 g) in MeOH was added dropwise 4 N hydrogen chloride in dioxane, and the mixture was stirred at room temperature for 2 hours. Solvent was evaporated and the residue was triturated with $Et_2O$. The solid was collected and washed with $Et_2O$ and dried in vacuo to give 1-(2-methoxyethyl)-N-methyl-1H-pyrazol-4-amine dihydrochloride.

NMR (DMSO-$d_6$): 2.83 (3H, s), 3.22 (3H, s), 3.67 (2H, t, J=5.2 Hz), 4.28 (2H, t, J=5.2 Hz), 5.80-6.30 (3H, br), 7.69 (1H, s), 8.08 (1H, s).

Prep 18

N-Methyl-1-[2-(4-morpholinyl)ethyl]-1H-pyrazol-4-amine trihydrochloride was prepared according to a similar manner to that of Prep 17.

NMR: 2.84 (3H, s), 2.95-3.50 (8H, m), 3.57 (2H, t, J=6.8 Hz), 4.68 (2H, t, J=6.8 Hz), 7.80 (1H, s), 8.24 (1H, s), 11.0-12.0 (4H, br).

Prep 19 tert-Butyl ethyl(1-methyl-1H-pyrazol-4-yl)carbamate was prepared according to a similar manner to that of Prep 15.

NMR: 1.18 (3H, t, J=7.1 Hz), 1.50 (9H, s), 3.62 (2H, q, J=7.1 Hz), 3.86 (3H, s), 7.37 (1H, s). 7.37-7.90 (1H, br).

Prep 20

N-Ethyl-1-methyl-1H-pyrazol-4-amine dihydrochloride was prepared according to a similar manner to that of Prep 17.

NMR (DMSO-$d_6$): 1.23 (3H, t, J=7.2 Hz), 3.20 (2H, q, J=7.2 Hz), 3.86 (3H, s), 7.65 (1H, s), 8.06 (1H, s), 8.30-9.00 (2H, br).

Prep 21

To a solution of the compound (A) (3.0 g) and DIPEA (3 ml) in $CH_2Cl_2$ was added t-butyldimethylsilylchloride (1.6 g), and the mixture was stirred at room temperature for 2 days. The mixture was diluted with EtOAc, washed with water three times and brine, dried over $MgSO_4$ and concentrated. The residue was chromatographed on silica gel ($CH_2Cl_2$: acetone=1:1) to give 3.28 g of the object compound.

MS: 1348.88

Prep 22

To a solution of the object compound of Prep 21 (3.27 g) in pyridine (31 ml) were added acetic anhydride (22.9 ml) and DMAP (148 mg), and the mixture was stirred at room temperature for overnight. The mixture was diluted with water and extracted with EtOAc. The organic phase was washed with water twice and concentrated. The residue was dissolved in NeOH (40 ml) and treated with 1 N HCl (15 ml). After stirring for 4 hours, the mixture was diluted with water and extracted with CH$_2$Cl$_2$ twice. The combined extracts were dried over MgSO$_4$ and concentrated. The residue was chromatographed on silica gel (CH$_2$Cl$_2$:acetone=1:1) to give 2.91 g of the object compound.

MS: 1318.62

Prep 23

To a solution of the object compound of Prep 22 (720 mg) and rhodium acetate dimer (241 mg) in CH$_2$Cl$_2$ (14 ml) was added dropwise ethyl diazoacetate (287 μl). Two further portions of rhodium acetate dimer (120 mg) and ethyl diazoacetate (145 μl) were added at intervals of 2 hours. After the starting compound was consumed, the mixture was filtered and the filtrate was concentrated. The residue was chromatographed on silica gel (CH$_2$Cl$_2$:acetone=1:1) to give 601 mg of the object compound. μ

MS: 1404.54

Prep 24

To a solution of the object compound of Prep 23 (76 mg) in MeOH (8 ml) was added 1 N NaOH aq. solution (4 ml), and the mixture was stirred at 50° C. for 2 hours. The mixture was acidified with 1 N HCl and extracted with CH$_2$Cl$_2$ three times. The combined extracts were dried over MgSO$_4$ and concentrated. The residue was chromatographed on silica gel (CH$_2$Cl$_2$:MeOH=9:1) to give 39 mg of the object compound.

MS: 1292.73

Prep 25

To a solution of the object compound of Prep 24 (230 mg) and TEA (50 μl) in THF (10 ml) was added isobutyl chloroformate (35 μl), and the mixture was stirred at room temperature for 0.5 hour. After the mixture was filtered, sodium borohydride (20 mg) was added in portions to the filtrate. After stirring for 1 hour, the mixture was acidified with 1 N HCl and extracted with CH$_2$Cl$_2$ three times. The combined extracts were dried over MgSO$_4$ and concentrated. The residue was submitted by ODS purification to give 85 mg of the object compound.

MS: 1278.53

Prep 26

The object compound was prepared according to a similar manner to that of Prep 2.

MS: 1443.15

Prep 27

To a solution of the object compound of Prep 25 (82 mg) in pyridine (3 ml) was added 4-methylbenzenesulfonyl chloride (60 mg), and the mixture was stirred at room temperature for overnight. The reaction was quenched with water and extracted with EtOAc. The organic phase was washed with 1 N HCl twice and aq. NaHCO$_3$ solution twice, dried over MgSO$_4$ and concentrated to give 83 mg of the object crude product, which was used for the next step without further purification.

MS: 1432.07

Prep 28

To a biphasic solution of the compound (A) (1.0 g), N,N,N,N-tetrabutylammonium chloride (45 mg) and 2,2,6,6-tetramethyl-1-piperidinyloxy, free radical (TEMPO; 25 mg) in CH$_2$Cl$_2$ (10 ml) and an aqueous mixed solution of NaHCO$_3$ (0.5 M) and potassium carbonate (0.05 M) (10 ml) was added N-chlorosuccinimide (162 mg) in portion. After the mixture was stirred at room temperature for overnight, two further portions of N,N,N,N-tetrabutylammonium chloride (18 mg), TEMPO (25 mg) and N-chlorosuccinimide (160 mg) were added at intervals of 2 hours. After the starting compound was consumed, the mixture was extracted with CH$_2$Cl$_2$ twice. The combined extracts were dried over MgSO$_4$ and concentrated.

The residue was chromatographed on silica gel (CH$_2$Cl$_2$:acetone=4:1 to 2:3) to give 86 mg of the object compound.

MS: 1232.31

Prep 29

The object compound was prepared according to a similar manner to that of Ex 43.

MS: 1247.25

Prep 30

To a solution of the compound (A) (1.23 g) in pyridine (8 ml) was added p-toluenesulfonyl chloride (760 mg). After the reaction mixture was stirred at room temperature for 4 hours, the mixture was diluted with EtOAc and ice water. The solution was treated with 6 N HCl and the organic phase was separated. After extracted with EtOAc, the combined organic phase was washed with water and brine. The solution was dried over MgSO$_4$ and concentrated in vacuo. The residue was chromatographed on silica gel (acetone:n-hexane=1:9 to 1:1) to give 1.09 g of the object compound.

ESI (M+H$_2$O)$^+$: 1405.50.

Prep 31

The mixture of the object compound of Prep 30 (2.93 g) in DMF (30 ml) was treated with imidazole (718 mg) and a 2.0 M toluene solution of t-butyldimethylsilyl chloride (4.22 ml) at room temperature for 4 hours. The reaction mixture was diluted with a 1/1 solvent mixture of EtOAc and hexane and washed with water and brine. The extract was dried over MgSO$_4$ and concentrated in vacuo. The residue was chromatographed on silica gel (acetone:n-hexane=1:9 to 3:7) to give 996 mg of the object minor compound (Prep 31-B) and 1.87 g of the object major compound (Prep 31-A).

Minor Compound

MS: 1366.55.

Major Compound

ESI (M+H$_2$O)$^+$: 1519.60

Prep 32

The mixture of the object minor compound of Prep 31 (100 mg) in DMF (1.4 ml) was treated with thiophenol (11 μl) and potassium carbonate (20 mg) at room temperature for 12 hours. The reaction mixture was diluted with EtOAc and washed with water and brine. The extract was dried over MgSO$_4$ and concentrated in vacuo. The residue was chromatographed on silica gel (acetone:n-hexane=1:9 to 3:7) to give 93.8 mg of the object compound.

MS: 1440.63

Prep 33

The mixture of the object compound of Prep 32 (144 mg) in CH$_2$Cl$_2$ (2 ml) was treated with m-chloroperbenzoic acid (52 mg) at 0° C. for 1 hour. The reaction mixture was diluted with EtOAc and washed with sat. sodium sulfite, NaHCO$_3$, water, and brine. The extract was dried over MgSO$_4$ and concentrated in vacuo. The residue was chromatographed on silica gel (acetone:n-hexane=1:9 to 4:6) to give 64.1 mg of the object compound.

MS: 1472.48.

Prep 34

The mixture of the object compound of Ex 49 (468 mg) in EtOH (9 ml) was treated with 2.6 M sodium ethoxide/EtOH (29 μl) at room temperature for 30 minutes. After treated with acetic acid (30 μl), the mixture was concentrated and the residue was chromatographed on silica gel (acetone:n-hexane=1:9 to 45:55) to give 354 mg of the object compound.

MS: 1250.22.

Prep 35

The mixture of the object major compound of Prep 31 (225 mg) in DMF (4.5 ml) was treated with 2,4-difluorophenol (43 μl) and NaH (12 mg) at room temperature for 12 hours. The reaction mixture was diluted with EtOAc and washed with water and brine. The extract was dried over MgSO$_4$ and concentrated in vacuo. The residue was chromatographed on silica gel (acetone:n-hexane=1:9 to 40:60) to give 129 mg of the object compound.

MS: 1460.66

Prep 36

The mixture of the object compound of Prep 30 (2.778 g) in DMF (20 ml) was treated with terabutylammonium azide (1.71 g) at 60° C. for 1 hour. The reaction mixture was diluted with EtOAc and washed with water and brine. The extract was dried over MgSO$_4$ and concentrated in vacuo. The residue was chromatographed on silica gel (acetone:n-hexane=1:9 to 1:1) to give 2.249 g of the object compound.

MS: 1259.47

Prep 37

To the mixture of the object compound of Prep 36 (2.08 g) and 2,6-lutidine (893 μl) in CH$_2$Cl$_2$ (30 ml) was added tert-butyldimethylsilyl trifluoromethanesulfonate (1.17 ml) at 0° C. After stirred at room temperature for 30 minutes, the reaction mixture was diluted with EtOAc and hexane and washed with water and brine. The extract was dried over MgSO$_4$ and concentrated in vacuo. The residue was chromatographed on silica gel (acetone:hexane=1:9 to 3:7) to give 1.39 g of the object compound.

MS: 1373.64

Prep 38

The mixture of the object compound of Prep 37 (120 mg) in toluene (1.2 ml) was treated with benzaldehyde (18 μl) and PPh$_3$ (34 mg) at 100° C. for 1.5 hours. The reaction mixture was poured into a solution of sodium borohydride (18 mg) in EtOH (1.2 ml) at 0° C. After stirred at room temperature for 30 minutes, the mixture was treated with acetic acid (100 μl) and concentrated. The residue was chromatographed on silica gel (MeOH:CH$_2$Cl$_2$ (0.2% TEA)=2:98 to 10:90) to give 57 mg of the object compound.

MS: 1437.74

Prep 39

The mixture of the object compound of Prep 36 (1.26 g) in toluene (5 ml) and EtOH (5 ml) was treated with PPh$_3$ (390 mg) at 90° C. for 2 hours. The mixture was concentrated. The residue was chromatographed on silica gel (MeOH:CH$_2$Cl$_2$ (0.2% TEA)=2:98 to 10:90) to give 1.03 g of the object compound.

MS: 1233.85

Prep 40

A solution of the object compound of Prep 36 (0.93 g) in MeOH (10 ml) was hydrogenated over 10% Pd/C (50% wet; 0.78 g) under hydrogen atmosphere for 2 hours. The mixture was filtered. Solvent was evaporated and the residue was chromatographed on silica gel (MeOH:CH$_2$Cl$_2$ (0.2% TEA)=2:98 to 8:92) to give the object compound.

MS: 1235.86.

Prep 41

To a solution of the object compound of Prep 30 (800 mg) in acetone (40 ml) was added NaI (432 mg), and the mixture was stirred 60° C. for 6 hours. After cooling to room temperature, the reaction was quenched with water and extracted with EtOAc. The organic phase was washed with aq. 5% NaHCO$_3$ solution twice, dried over MgSO$_4$ and concentrated to give 750 mg of the object crude product, which was used for the next step without further purification.

MS: 1344.46

Prep 42

To a solution of tert-butyl 4-{[(trifluoromethyl)sulfonyl]oxy}-3,6-dihydropyridine-1(2H)-carboxylate (610 mg) in 1,2-dimethoxyethane (15 ml) was added 3-thienylboronic acid (353 mg), tetrakis(triphenylphosphine) palladium (106 mg) and aq. 2M cesium carbonate solution (2.7 ml) and the mixture was refluxed 2 hours under nitrogen atmosphere. After removal of solvent in vacuo, the residue was extracted by EtOAc. The extract was washed with brine, dried over MgSO$_4$ and concentrated in vacuo. The resultant residue was purified by silica gel column (n-hexane:EtOAc=80:20) to give tert-butyl 4-(3-thienyl)-3,6-dihydropyridine-1(2H)-carboxylate (350 mg) as a colorless oil.

$^1$H NMR (DMSO-d$_6$, δ): 1.42 (9H, s), 2.43 (2H, br-s), 3.51 (2H, t, J=5.6 Hz), 3.97 (2H, br-s), 6.17 (1H, br-s), 7.34 (1H, dd, J=5.2, 1.4 Hz), 7.41 (1H, br-s), 7.51 (1H, dd, J=5.2, 3.0 Hz).

Prep 43

To a solution of tert-butyl 4-(3-thienyl)-3,6-dihydropyridine-1(2H)-carboxylate (170 mg) in EtOAc (1.7 ml) and water (0.085 ml) was added 4 N hydrogen chloride in EtOAc (1.7 ml) and the mixture was stirred at room temperature for 1 hour. Solvent was removed in vacuo to give 4-(3-thienyl)-1,2,3,6-tetrahydropyridine hydrochloride (120 mg) as a dark gray powder. The obtained crude product was used in next reaction without further purification.

$^1$H NMR (DMSO-d$_6$, δ): 2.66 (2H, br-s), 3.27 (2H, br-s), 3.71 (2H, br-s), 6.20 (1H, br-s), 7.39 (1H, dd, J=5.0, 1.4 Hz), 7.54 (1H, m), 7.56 (1H, dd, J=5.0, 2.8 Hz), 9.12 (1H, br-s).

Prep 44

To a solution of 1-methyl-1H-imidazole (2 g) in THF (15 ml) was added 1.59 M n-butyllithium in n-hexane solution (18.4 ml) slowly under ice bath cooling, and the mixture was stirred at room temperature for 3 hours. To this reaction mixture was added tert-butyl 4-oxopiperidine-1-carboxylate (5.8 g) in THF (15 ml) solution and the mixture was stirred at room temperature for 2 hours. The reaction mixture was extracted with EtOAc and was washed with brine, and was dried over MgSO$_4$. Solvent was removed in vacuo, and the residue was purified by silica gel column (CHCl$_3$:MeOH=95:5 to 90:10) to give tert-butyl 4-hydroxy-4-(1-methyl-1H-imidazol-2-yl)piperidine-1-carboxylate (4.02 g) as a pale yellow powder.

$^1$H NMR (DMSO-d$_6$, δ): 1.40 (9H, s), 1.79 (2H, d, J=13.6 Hz), 1.88-1.98 (2H, m), 3.23 (2H, br-s), 3.63-3.66 (2H, m), 3.77 (3H, s), 5.40 (1H, s), 6.71 (1H, d, J=1.1 Hz), 7.02 (1H, d, J=1.1 Hz).

Prep 45

To a solution of tert-butyl 4-hydroxy-4-(1-methyl-1H-imidazol-2-yl)piperidine-1-carboxylate (300 mg) in DMF (3 ml) was added NaH (60% dispersion in mineral oil; 77 mg) and MeI (120 μl) under ice bath cooling, and the mixture was stirred at room temperature for 2 hours. The reaction mixture was extracted with EtOAc and was washed with water and brine, and was dried over MgSO$_4$. Solvent was removed in vacuo, and the residue was purified by silica gel column (n-hexane:EtOAc=50:50 to EtOAc only) to give tert-butyl 4-methoxy-4-(1-methyl-1H-imidazol-2-yl)piperidine-1-carboxylate (182 mg) as a colorless oil.

NMR: 1.46 (9H, s), 2.11 (4H, br-d), 3.02 (3H, s), 3.22-3.29 (2H, m), 3.82 (3H, s), 3.79-3.89 (2H, m), 6.86 (1H, d, J=1.2 Hz), 6.95 (1H, d, J=1.2 Hz).

Prep 46

To a solution of tert-butyl 4-methoxy-4-(1-methyl-1H-imidazol-2-yl)piperidine-1-carboxylate (182 mg) in EtOAc (0.7 ml) and water (0.09 ml) was added 4N hydrogen chloride in EtOAc (0.7 ml) and the mixture was stirred at room temperature for 2 hours. Solvent was removed in vacuo to give 4-methoxy-4-(1-methyl-1H-imidazol-2-yl)piperidine dihydrochloride (122 mg) as a colorless powder. The obtained crude product was used in next reaction without further purification.

¹H NMR (DMSO-d$_6$, δ): 1.46 (9H, s), 2.39-2.45 (4H, m), 2.98-3.10 (2H, m), 3.07 (3H, s), 3.26 (2H, d, J=13 Hz), 7.01 (1H, d, J=2.0 Hz), 7.83 (1H, d, J=2.0 Hz), 9.35 (1H, br s), 9.53 (1H, br-s).

Prep 47

To a solution of tert-butyl 4-hydroxy-4-(1-methyl-1H-imidazol-2-yl)piperidine-1-carboxylate (800 mg) in CH$_2$Cl$_2$ (8 ml) was added methanesulfonyl chloride (0.44 ml) and TEA (1.6 ml) under ice bath cooling, and the mixture was stirred at room temperature for 4 hours. The reaction was quenched with aq. NaHCO$_2$ solution and extracted with EtOAc. The organic phase was washed with brine and dried over MgSO$_4$. Solvent was removed in vacuo, and the residue was purified by silica gel column (CHCl$_3$:MeOH=95:5 to 90:10) to give tert-butyl 4-(1-methyl-1H-imidazol-2-yl)-3,6-dihydropyridine-1(2H)-carboxylate (398 mg) as a colorless oil.

¹H NMR (DMSO-d$_6$, δ): 1.36-1.45 (2H, m), 1.42 (9H, s), 3.50 (2H, d, J=5.6 Hz), 3.67 (3H, s), 3.98-4.04 (2H, m), 6.05 (1H, br-s), 6.85 (1H, d, J=1.0 Hz), 7.10 (1H, d, J=1.0 Hz).

Prep 48

To a solution of tert-butyl 4-(1-methyl-1H-imidazol-2-yl)-3,6-dihydropyridine-1(2H)-carboxylate (398 mg) in MeOH (4.0 ml) was added 5% Pd/C (wet; 40 mg) and the mixture was stirred at room temperature for 7 hours under hydrogen atmosphere (1 atm). After removal of Pd/C with cerite, the filtrate was concentrated in vacuo. The resultant residue was purified by silica gel column (n-hexane:EtOAc=80:20 to EtOAc only) to give tert-butyl 4-(1-methyl-1H-imidazol-2-yl)piperidine-1-carboxylate (132 mg) as a colorless oil.

¹H NMR (DMSO-d$_6$, δ): 1.41 (9H, s), 1.53 (2H, m), 1.75 (2H, dd, J=13.4, 2.8 Hz), 2.86-2.97 (3H, m), 3.58 (3H, s), 3.98 (2H, d, J=13.3 Hz), 6.72 (1H, d, J=1.2 Hz), 6.97 (1H, d, J=1.2 Hz).

Prep 49

To a solution of tert-butyl 4-(1-methyl-1H-imidazol-2-yl)piperidine-1-carboxylate (132 mg) in EtOAc (1.3 ml) was added 4N hydrogen chloride in EtOAc (1.3 ml) and the mixture was stirred at room temperature for 2 hours. Solvent was removed in vacuo to give 4-(1-methyl-1H-imidazol-2-yl)piperidine dihydrochloride (108 mg) as a colorless powder. The obtained crude product was used in next reaction without further purification.

¹H NMR (DMSO-d$_6$, δ): 2.07-2.11 (4H, m), 2.96-3.09 (2H, m), 3.37 (2H, d, J=12.7 Hz), 3.52-3.62 (1H, m), 3.85 (3H, s), 7.58 (1H, d, J=2.0 Hz), 7.66 (1H, d, J=2.0 Hz), 9.31 (1H, br-s), 9.58 (1H, br-s), 14.82 (1H, br-s).

Prep 50

Azetidine-3-carboxylic acid (2.0 g) was dissolved in a mixed solvent of THF (20 ml) and water (10 ml). The pH value of the mixture was adjusted to 9 with 1N NaOH under ice-cooled bath. Boc$_2$O was added to the mixture, and the whole was stirred for 1.5 hours with keeping pH=9. The whole was made acidic with 0.5 N HCl and extracted with EtOAc, and the extract was washed with water and brine and dried over MgSO$_4$. Concentration under reduced pressure gave 1-(tert-butoxycarbonyl)azetidine-3-carboxylic acid (2.7 g).

ESI (M+Na)$^+$: 224.2

Prep 51

To a solution of 1-(tert-butoxycarbonyl)azetidine-3-carboxylic acid (2.0 g) in THF (30 ml) was added borane-dimethyl sulfide complex (4.0 ml; 10.0 M as borane) under ice-cooled bath, and the mixture was stirred for 8 hours at room temperature. 1 N HCl (10 ml) was added dropwise to the mixture under ice-cooled bath, and THF was removed under reduced pressure. The whole residue was extracted with EtOAc, and the extract was washed with brine and dried over MgSO$_4$. Concentration under reduced pressure gave tert-butyl 3-(hydroxymethyl)azetidine-1-carboxylate (1.6 g).

ESI (M+Na)$^+$: 210.4

Prep 52

To a solution of tert-butyl 3-(hydroxymethyl)azetidine-1-carboxylate (1.0 g) in DMF (20 ml) was added NaH (235 mg; 60% oil suspension) under nitrogen atmosphere, and the mixture was stirred for 30 minutes at room temperature. MeI (665 μl) was added to the mixture, and the whole was stirred for 2 hours. Water was added to the mixture, and the whole was extracted with EtOAc. The extract was washed with water and brine and dried over MgSO$_4$. Concentration under reduced pressure gave a residue, which was purified with silica gel chromatography eluting with n-hexane:EtOAc=5:1 to give tert-butyl 3-(methoxymethyl)azetidine-1-carboxylate (1.04 g).

MS: 202.08

Prep 53 tert-Butyl 3-(methoxymethyl)azetidine-1-carboxylate was dissolved in 4 N hydrogen chloride/EtOAc (13 ml) under ice-cooled bath and the whole was stirred for 2 hours at room temperature. Concentration under reduced pressure gave 3-(methoxymethyl)azetidine hydrochloride (559 mg).

MS: 102.2

Prep 54

To a stirred mixture of (2R)-1-aminopropan-2-ol (1.2 g) and di-tert-butyl dicarbonate (3.7 g) in THF (24 ml) was added TEA (3.3 ml), and the whole was stirred for overnight. Water was added to the mixture, and the whole was made acidic with citric acid. The whole was extracted with EtOAc, and the extract was washed with water, NaHCO$_3$, water and brine and dried over MgSO$_4$. Concentration under reduced pressure gave tert-butyl [(2R)-2-hydroxypropyl]carbamate (2.7 g).

ESI (M+Na)$^+$: 198.2

Prep 55

To a solution of tert-butyl [(2R)-2-hydroxypropyl]carbamate (2.7 g) in CH$_2$Cl$_2$ (41 ml) were added N,N,N',N'-tetramethylnaphthalene-1,8-diamine (3.63 g) and trimethyloxonium tetrafluoroborate (2.51 g), and the whole was stirred for 3 hours at room temperature. Water was added to the mixture, and the whole was extracted with EtOAc, and the extract was washed with water and brine and dried over MgSO$_4$. Concentration under reduced pressure gave tert-butyl [(2R)-2-methoxypropyl]carbamate (2.73 g).

ESI (M+Na)$^+$: 212.4

Prep 56

To a solution of tert-butyl [(2R)-2-methoxypropyl]carbamate (2.72 g) in DMF (41 ml) was added NaH (862 mg; 60% oil suspension) under nitrogen atmosphere, and the mixture was stirred at room temperature for 30 minutes. MeI (1.79 ml) was added to the mixture, and the whole was stirred for 3 hours at the same temperature. Water was added, and the whole was extracted with EtOAc and the extract was washed with water and brine and dried over MgSO$_4$. Concentration under reduced pressure gave a residual oil, which was purified with silica gel column eluting with EtOAc:n-hexane=1:5 to give tert-butyl [(2R)-2-methoxypropyl]methylcarbamate (1.94 g).

ESI (M+Na)$^+$: 226.3

Prep 57

The mixture of tert-butyl [(2R)-2-methoxypropyl]methylcarbamate (1.93 g) and 4 N hydrogen chloride in EtOAc (4.75 ml) was stirred for 3 hours at room temperature. The solvent was removed under reduced pressure to give (2R)-2-methoxy-N-methylpropan-1-amine hydrochloride (1.35 g).

MS: 104.3

Prep 58 tert-Butyl [(2S)-2-hydroxypropyl]carbamate was prepared according to a similar manner to that of Prep 54.

ESI (M+Na)$^+$: 198.2

Prep 59 tert-Butyl [(2S)-2-methoxypropyl]carbamate was prepared according to a similar manner to that of Prep 55.

ESI (M+Na)$^+$: 212.4

Prep 60 tert-Butyl [(2S)-2-methoxypropyl]methylcarbamate was prepared according to a similar manner to that of Prep 56.

ESI (M+Na)$^+$: 226.3

Prep 61

(2S)-2-Methoxy-N-methylpropan-1-amine hydrochloride was prepared according to a similar manner to that of Prep 57.

MS: 104.3

Prep 62

To a stirred solution of diisopropylamine (88 ml) in THF (650 ml) was added n-butyllithium (238 ml; 2.64 M in hexane) at −60° C. under nitrogen atmosphere, and the mixture was stirred for 30 minutes with warming to −10° C. The mixture was cooled to −60° C. again, and 4-benzylmorpholin-3-one in THF (100 ml) was added to the mixture. The whole was stirred for 30 minutes at the same temperature. To a stirred solution of ethylchlorocarbonate (60 ml) in THF (50 ml) under nitrogen atmosphere at −60° C. was added the above mixture at the same temperature, and the whole was stirred for 30 minutes at −40° C. The mixture was quenched with pH 7 buffer, and the whole was extracted with EtOAc. The extract was washed with water and brine and dried over MgSO$_4$. Concentration under reduced pressure gave a residual oil, which was purified with silica gel column eluting with EtOAc:n-hexane=1:4-1:3 to give diethyl 4-benzyl-3-oxomorpholine-2,2-dicarboxylate (25.0 g).

ESI (M+Na)$^+$: 358.1

Prep 63

To a stirring suspension of lithium aluminum hydride (8.49 g) in THF (500 ml) was added diethyl 4-benzyl-3-oxomorpholine-2,2-dicarboxylate (25 g) under ice-cooled bath, and the mixture was stirred for 1 hour at room temperature. Then the whole was warmed up to 65° C. (inner temperature), and the mixture was stirred for 2 hours. The whole was cooled with ice-cooled bath, and water (8.5 ml) was added dropwise to the mixture. The whole was stirred for 15 minutes. 4 N NaOH (8.5 ml) was added to the mixture, and the whole was stirred for 15 minutes. Then water (25.5 ml) was added again to the mixture and the whole was stirred for 1 hour at room temperature. The white precipitate was filtered off, and the filtrate was concentrated under reduced pressure. The residue was dissolved in diisopropyl ether, and triturated to yield white solid, which was collected by filteration to give (4-benzylmorpholine-2,2-diyl)dimethanol (10.3 g).

ESI (M+Na)$^+$: 260.2

Prep 64

To a stirred solution of (4-benzylmorpholine-2,2-diyl)dimethanol (10.3 g) in DMF (103 ml) was added NaH (3.82 g; 60% oil suspension) under ice-cooled bath. The mixture was allowed to room temperature, and stirred for 20 minutes. The whole was cooled to 10° C. (inner temperature) under ice-cooled bath again, and MeI (6.09 ml) was added dropwise to the mixture. The mixture was stirred for 45 minutes, and quenched with pH 7-buffer. The whole was extracted with EtOAc and the extract was washed with 1 N HCl (100 ml). The aqueous layer was made basic with aq. NaHCO$_3$, and the whole was extracted with EtOAc. The extract was washed with water and brine and dried over MgSO$_4$. Concentration under reduced pressure gave a residual oil (10.1 g), which was purified with silica gel chromatography eluting with n-hexane:EtOAc=20:1→4:1 to give 4-benzyl-2,2-bis(methoxymethyl)morpholine (6.88 g).

MS: 266.4

Prep 65

To a solution of 4-benzyl-2,2-bis(methoxymethyl)morpholine (6 g) and conc HCl (2.41 ml) in MeOH (60 ml) was added 20% palladium hydroxide on charcoal (1.2 g), and the whole was stirred for 2 hours at room temperature under hydrogen (2.0 atm). The catalyst was filtered off, and the filtrate was concentrated under reduced pressure to give 2,2-bis(methoxymethyl)morpholine hydrochloride (3.6 g). The obtained HCl salt was diluted with CH$_2$Cl$_2$ and washed with 1N—NaOH. The organic phase was concentrated under reduced pressure to give gave free form, which was used for next reaction.

MS: 176.2

Prep 66

To a solution of tert-butyl 4-(2-hydroxyethyl)-4-(hydroxymethyl)piperidine-1-carboxylate (500 mg) in DMF (5 ml) was added NaH (60% suspension in oil 185 mg) and MeI (600 µl) under ice bath cooling, and the mixture was stirred at ambient temperature for 2 hours. The reaction mixture was extracted with EtOAc and was washed with brine, and was dried over MgSO$_4$. Solvent was removed in vacuo to give tert-butyl 4-(2-methoxyethyl)-4-(methoxymethyl)piperidine-1-carboxylate (460 mg) as a white powder. The obtained crude product was used in next reaction without further purification.

ESI (M+Na)$^+$: 310.3.

Prep 67

To a solution of tert-butyl 4-(2-methoxyethyl)-4-(methoxymethyl)piperidine-1-carboxylate (400 mg) in EtOAc (7 ml) was added 1 N HCl (7 ml) under ice bath cooling, and the mixture was stirred at ambient temperature for 3 hours. The reaction mixture was concentrated in vacuo to give 4-(2-methoxyethyl)-4-(methoxymethyl)piperidine hydrochloride (260 mg) as a white powder. The obtained crude product was used in next reaction without further purification.

NMR: 1.50-1.74 (4H, m), 2.49 (4H, 5th, J=1.8 Hz), 2.90-3.07 (3H, m), 3.20 (2H, s), 3.21 (3H, s), 3.26 (3H, s), 3.34 (2H, t, J=6.8 Hz), 8.73 (1H, br s).

MS: 188.4.

Prep 68 tert-Butyl 4-methoxy-4-(3-methoxypropyl)piperidine-1-carboxylate was prepared according to a similar manner to that of Prep 66.

NMR: 1.32-1.42 (2H, m), 1.45 (9H, s), 1.47-1.64 (2H, m), 1.69-1.77 (2H, m), 2.98-3.11 (2H, m), 3.14 (3H, s), 3.33 (3H, s), 3.38 (2H, t, J=6.0 Hz), 3.68-3.85 (2H, m).

ESI (M+Na)$^+$: 310.3.

Prep 69

4-Methoxy-4-(3-methoxypropyl)piperidine hydrochloride was prepared according to a similar manner to that of Prep 67.

$^1$H NMR (DMSO-d$_6$, δ): 1.37-1.51 (2H, m), 1.53-1.68 (2H, m), 1.78-1.89 (2H, m), 2.78-2.93 (2H, m), 2.98-3.11 (2H, m), 3.05 (3H, s), 3.22 (3H, s), 3.31 (2H, t, J=5.5 Hz), 8.90 (2H, br-s).

MS: 188.4.

Prep 70

To a solution of 1-tert-butyl 4-ethyl piperidine-1,4-dicarboxylate (2.57 g) in THF (26 ml) was added 0.5 M solution of potassium bis(trimethylsilyl)amide in toluene (24.0 ml) under at −70° C. After 15 minutes, chloromethyl methyl ether (1.2 ml) was added and it was stirred at 0° C. for 2 hours. Water was added and extracted with EtOAc. The organic phase was washed with water and brine, dried over $MgSO_4$, evaporated under reduced pressure. The residue was purified by silica gel column to give 1-tert-butyl 4-ethyl 4-(methoxymethyl)piperidine-1,4-dicarboxylate (2.05 g) as oil.

NMR: 1.27 (3H, t, J=7.2 Hz), 1.46 (9H, s), 2.04-2.13 (2H, m), 2.88-3.03 (2H, m), 3.30 (3H, s), 3.38 (3H, s), 3.79-3.91 (2H, m), 4.20 (2H, q, J=7.2 Hz).

ESI $(M+Na)^+$: 324.2.

Prep 71

To a solution of 1-tert-butyl 4-ethyl 4-(methoxymethyl) piperidine-1,4-dicarboxylate (2.05 g) in toluene (21 ml) was added 0.99 M solution of diisobutyl aluminum hydride in toluene (16.5 ml) under at 0° C. It was stirred at room temperature for 2 hours. Water was added and extracted with EtOAc. The organic phase was washed with water and brine, dried over $MgSO_4$, evaporated off. The residue was purified by silica gel column to give tert-butyl 4-(hydroxymethyl)-4-(methoxymethyl)piperidine-1-carboxylate (0.95 g) as oil.

NMR: 1.26-1.57 (4H, m), 1.45 (9H, s), 2.20-2.90 (1H, br), 3.27-3.36 (2H, m), 3.36 (3H, s), 3.37 (3H, s), 3.40-3.55 (2H, m), 3.61 (2H, s).

ESI $(M+Na)^+$: 282.3.

Prep 72 tert-Butyl 4,4-bis(methoxymethyl)piperidine-1-carboxylate was prepared according to a similar manner to that of Prep 66.

NMR: 1.42-1.49 (4H, m), 1.45 (9H, s), 3.26 (4H, s), 3.33 (6H, s), 3.35-3.41 (4H, m).

ESI $(M+Na)^+$: 296.4.

Prep 73

4,4-bis(methoxymethyl)piperidine hydrochloride was prepared according to a similar manner to that of Prep 67.

$^1$H NMR (DMSO-$d_6$, δ): 1.59 (4H, t, J=6.0 Hz), 2.95-3.06 (4H, m), 3.22 (4H, s), 3.26 (6H, s), 8.87 (2H, br-s).

MS: 174.4.

Prep 74

To a solution tert-butyl [(2R)-2,3-dihydroxypropyl]carbamate (1.05 g) in $CH_2Cl_2$ (21 ml) were added N,N,N',N'-tetramethylnaphthalene-1,8-diamine (4.12 g) and molecular sieves 3A (2.89 g). To this was added trimethyloxonium tetrafluoroborate (2.84 g) portionwise under ice cooling. And it was stirred at room temperature for overnight. To this was added sat. eq. $NaHCO_2$, and insoluble materials were filtered off, and the filtrate was extracted with EtOAc. The organic phase was washed with 10% potassium hydrogen sulfate two times, sat. aq. $NaHCO_3$, and brine, dried over $MgSO_4$, filtered, and evaporated off. The crude residue containing tert-butyl [(2R)-2,3-dimethoxypropyl]carbamate was used to the next step without further purification.

NMR: 1.45 (9H, s), 3.15-3.48 (6H, m), 3.37 (3H, s), 3.43 (3H, s), 4.70-5.00 (1H, br).

Prep 75 tert-Butyl [(2R)-2,3-dimethoxypropyl]methylcarbamate was prepared according to a similar manner to that of Prep 66.

NMR: 1.46 (9H, s), 2.92 (3H, s), 3.22-3.61 (5H, m), 3.37 (3H, s), 3.48 (3H, s).

Prep 76

(2R)-2,3-Dimethoxy-N-methylpropan-1-amine hydrochloride was prepared according to a similar manner to that of Prep 67.

$^1$H NMR (DMSO-$d_6$, δ): 2.52 (3H, s), 2.87-3.08 (2H, m), 3.28 (3H, s); 3.36 (3H, s), 3.42 (2H, dd, J=10.6, 4.4 Hz), 3.47 (2H, dd, J=10.6, 4.6 Hz), 3.68-3.74 (1H, m), 8.69 (1H, br-s), 9.19 (1H, br-s).

MS: 134.4.

Prep 77 tert-Butyl [(2S)-2,3-dimethoxypropyl]carbamate was prepared according to a similar manner to that of Prep 74.

NMR: 1.45 (9H, s), 3.15-3.48 (6H, m), 3.37 (3H, s), 3.43 (3H, s), 4.70-5.00 (1H, br).

Prep 78 tert-Butyl [(2S)-2,3-dimethoxypropyl]methylcarbamate was prepared according to a similar manner to that of Prep 66.

NMR: 1.46 (9H, s), 2.92 (3H, s), 3.22-3.61 (5H, m), 3.37 (3H, s), 3.48 (3H, s).

Prep 79

(2S)-2,3-Dimethoxy-N-methylpropan-1-amine hydrochloride was prepared according to a similar manner to that of Prep 67.

$^1$H NMR (DMSO-$d_6$, δ): 2.52 (3H, s), 2.87-3.08 (2H, m), 3.28 (3H, s), 3.36 (3H, s); 3.42 (2H, dd, J=10.6, 4.4 Hz), 3.47 (2H, dd, J=10.6, 4.6 Hz), 3.68-3.74 (1H, m), 8.70 (1H, br-s), 9.20 (1H, br-s).

MS: 134.4.

Prep 80

To a solution of the compound (A) (12.4 g) in THF (60 ml) was added 4-methylbenzenesulfonic acid monohydrate (10.5 g) and the mixture was stirred at 55° C. for 22 hours. To the mixture was added 1 N NaOH and neutralized under ice bath cooling, and was added $Boc_2O$ (10.8 g). The pH value of the mixture was adjusted to 8 with 1 N NaOH under ice bath cooling. The mixture was stirred at ambient temperature for 5 hours. Resulting mixture was concentrated in vacuo and extracted with EtOAc. The organic phase was washed with brine, and dried over magnesium sulfate. Solvent was removed in vacuo, and the residue was purified by silica gel column (acetone:n-hexane=50:50) to give the object compound (7.7 g) as an amorphous powder.

MS: 1334.59.

Prep 81

To the solution of the object compound of Prep 80 (7.7 g) in MeOH (110 ml) was added 1 N NaOH (57 ml) under ice-bath cooling. After being stirred for 4 hours at ambient temperature, the solution was acidified with 1 N HCl to be pH=6.8, and was concentrated in vacuo to remove MeOH, and extracted with EtOAc. The organic layer was washed with brine, dried over $MgSO_4$, and concentrated in vacuo to give the object compound (6.4 g) as an amorphous powder. Obtained crude product was used in next reaction without further purification.

MS: 1352.74.

Prep 82

To a solution of the object compound of Prep 81 (6.4 g) in $CH_2Cl_2$ (120 ml) was added L-threonine methyl ester hydrochloride (1.5 g), HOAt (1.5 g) and WSC (1.7 ml) under ice bath cooling, and the mixture was stirred for 7 hours at ambient temperature. The resulting mixture was washed with 5% citric acid and brine, and dried over $MgSO_4$. Solvent was removed in vacuo, and the residue was purified by silica gel column (acetone:$CH_2Cl_2$=50:50) to give the object compound (6.5 g) as an amorphous powder.

MS: 1467.63.

Prep 83

To a solution of the object compound of Prep 82 (6.5 g) in $CH_2Cl_2$ (120 ml) was added collidine (6 ml) and acetyl chloride (1.6 ml) under ice bath cooling, and the mixture was stirred for 3.5 hours at ambient temperature. The resulting mixture was washed with 0.5 N HCl and brine, and dried over MgSO$_4$. Solvent was removed in vacuo, and the residue was purified by silica gel column MeOH:CH$_2$Cl$_2$=4:96) to give the object compound (5.6 g) as an amorphous powder.

MS: 1509.71.

Prep 84

To a solution of the object compound of Prep 83 (5.5 g) in CH$_2$Cl$_2$ (60 ml) was added trifluoroacetic acid (14 ml) under ice bath cooling, and the mixture was stirred for 2.5 hours under ice bath cooling. Resulting mixture was neutralized with potassium carbonate aqueous solution under ice bath cooling and concentrated in vacuo. To the residual solution was added sat. aq. NaHCO$_3$ solution to adjust pH=8, and the mixture was extracted with EtOAc. The organic phase was washed with sat. aq. NaHCO$_3$ solution and brine, and dried over MgSO$_4$. Solvent was removed in vacuo to give the object compound (5.6 g) as a solid. Obtained crude product was used in next reaction without further purification.

MS: 1409.64.

Prep 85

To a solution of the object compound of Prep 84 (5.5 g) in EtOAc (70 ml) was added a solution of isothiocyanatobenzene (940 µl) and DIPEA (2.0 ml) at ambient temperature. After being stirred for 3 hours at the same temperature, N,N-dimethylaminopropylamine (1.24 ml) was added to the solution. The solution was stirred for 0.5 hours. It was washed with 0.5 N HCl, aq. NaHCO$_3$ solution and brine, dried over MgSO$_4$, and concentrated in vacuo to give the object compound (5.5 g) as a solid. Obtained crude product was used in next reaction without further purification.

MS: 1544.95.

Prep 86

The object compound of Prep 85 (2.8 g) was dissolved in MeCN (30 ml) was added 1 N HCl (18 ml) under ice bath cooling. After being stirred at 30° C. for 2 hours, the solution was neutralized with 1 N NaOH (19 ml), concentrated in vacuo to remove MeCN, and extracted with EtOAc (150 ml). The organic phase was washed with aq. NaHCO$_3$ solution and brine, dried over MgSO$_4$, and concentrated in vacuo. The residue was purified by silica gel column (MeOH:CH$_2$Cl$_2$=10:90) to give the object compound (2.1 g) as an amorphous powder.

MS: 1308.42.

Prep 87

The object compound was prepared according to a similar manner to that of Prep 85.

MS: 1443.62.

Prep 88

The object compound was prepared according to a similar manner to that of Prep 86.

MS: 1237.58.

Prep 89

To a solution of the object compound of Prep 88 (670 mg) in CH$_2$Cl$_2$ (15 ml) was added (2R)-2-{[(9H-fluoren-9-ylmethoxy)carbonyl](methyl)amino}propanoic acid (265 mg), 1-hydroxy-7-azabenzotriazole (221 mg) and WSC (194 µl) under ice bath cooling, and the mixture was stirred at 5° C. for 4 hours. The reaction mixture was concentrated in vacuo and the residue was extracted with EtOAc. The organic phase was washed with 1 N HCl, sat. aq. NaHCO$_3$ solution, and brine, and was dried over MgSO$_4$. Solvent was removed in vacuo, and the residue was purified by silica gel column (acetone:hexane=45:55) to give the object compound (574 mg) as an amorphous powder.

MS: 1544.57.

Prep 90

To a solution of the object compound of Prep 89 (574 mg) in dioxane (6 ml) was added 1 N lithium hydroxide (1.5 ml) at ambient temperature and the mixture was stirred for 2 hours. To the reaction mixture was added 5% citric acid aqueous solution to adjust pH=5, and the solution was extracted with EtOAc. The organic phase was washed with brine, and was dried over MgSO$_4$. Solvent was removed in vacuo to give the object compound (200 mg) as a solid. The obtained crude product was used in next reaction without further purification.

MS: 1266.60.

Prep 91

To a solution of the object compound of Prep 90 (178 mg) in CH$_2$Cl$_2$ (141 ml) were added 1-hydroxy-7-azabenzotriazole (23 mg) and WSC (27 µl) under ice bath cooling, and the mixture was stirred at ambient temperature for 15 hours. The reaction mixture was washed with 0.5 N HCl, sat. aq. NaHCO$_3$ solution, and brine, and was dried over MgSO$_4$. Solvent was removed in vacuo, and the residue was purified by silica gel column (acetone:CH$_2$Cl$_2$=50:50) to give the object compound (102 mg) as an amorphous powder.

MS: 1248.59.

Retention time: 5.4 minutes (HPLC, column: Shiseido UG120 C18, 100 mm×4.6 mm ID, eluent: 60% MeCN/H$_2$O, flow rate: 1.0 ml/minute)

Prep 92

To a solution of the object compound of Prep 91 (102 mg) in CH$_2$Cl$_2$ (5 ml) were added 4-nitrophenyl chloroformate (131 mg) and N-methylmorpholine (72 µl) under ice bath cooling. After the mixture was stirred at room temperature for overnight, the mixture was diluted with EtOAc, washed with 1 N HCl and aq. NaHCO$_3$ solution, dried over MgSO$_4$ and concentrated. Solvent was removed in vacuo, and the residua was purified by silica gel column (acetone:CH$_2$Cl$_2$=50:50) to give the object compound (97 mg) as an amorphous powder.

MS: 1413.34.

Prep 93

The object compound was prepared according to a similar manner to that of Prep 28.

MS: 1246.99

Prep 94

The object compound was prepared according to a similar manner to that of Prep 28.

MS: 1277.01

Prep 95

The object compound, which was used for the next step without further purification, was prepared according to a similar manner to that of Prep 119.

MS: 1490.48

Prep 96

The object compound was prepared according to a similar manner to that of Prep 121.

The configuration at 3 position of this compound was determined to be (R) in comparison with the HPLC spectra of the authentic sample whose configuration at 3 position was confirmed to be (R), synthesized by alternative synthetic method as described below (Prep 154).

NMR: 0.70 (3H, d, J=6.8 Hz), 0.81 (3H, d, J=6.5 Hz), 0.83 (3H, d, J=6.5 Hz), 0.84-0.92 (9H, m), 0.92-1.08 (8H, m), 1.12 (6H, t-like, J=6.6 Hz), 1.20-1.48 (10H, m), 1.48-1.65 (3H, m), 1.66 (3H, d, J=5.2 Hz), 1.67-2.40 (23H, m), 2.43 (1H, d, J=4.9 Hz), 2.91 (3H, s), 3.00 (3H, s), 3.03 (3H, s), 3.07 (3H, s), 3.08 (3H, s), 3.22 (3H, s), 3.35-3.45 (2H, m), 3.45-3.55 (2H, m), 3.73 (1H, m), 4.05-4.40 (2H, m), 4.52 (1H, t-like, J=7.0 Hz), 4.70 (1H, t-like, J=7.0 Hz), 4.70-4.90 (2H, m), 4.90-5.02 (2H, m), 5.02-5.12 (3H, m), 5.12-5.58 (3H, m), 5.65 (1H, d, J=3.1 Hz), 6.69 (1H, d, J=8.0 Hz), 6.89 (1H, d, J=7.5 Hz), 7.00 (1H, d, J=9.0 Hz), 7.73 (1H, d, J=9.0 Hz), 9.03 (1H, d, J=9.2 Hz).

MS: 1262.30

Retention time: 5.9 minutes (purity 94%; HPLC, column: Shiseido UG120 C18, 100 mm×4.6 mm ID, eluent: 60% MeCN/$H_2O$, flow rate: 1.0 ml/minute)

Prep 97

The object compound was prepared according to a similar manner to that of Prep 2.

MS: 1427.37

Prep 98

To a solution of N,N-diisopropylamine (0.96 ml) in THF (15 ml) was added dropwise 1.5 M n-butyllithium in hexane (4.6 ml) at −20° C. and the mixture was stirred for 5 minutes at the same temperature. After cooling to −78° C., a solution of the starting compound (1.0 g) in THF (10 ml) was added dropwise over 10 minutes to the mixture and the whole was stirred for 15 minutes. To the resulting yellow solution was added portions allyl iodide (0.63 ml) at the same temperature, and the mixture was gradually warmed up to 5° C. After stirring at 5° C. for 5 minutes, the reaction was quenched with water and extracted with EtOAc. The organic phase was dried over $MgSO_4$ and concentrated. The residue was chromatographed on silica gel (hexane/acetone=7/3) to give 0.52 g of the objective intermediate as a mixture of the starting compound. This crude product was dissolved in MeOH (15 ml), and treated with 1 N aq. HCl solution (7 ml). After stirring at room temperature for 2 hours, the mixture was diluted with water and extracted with $CH_2Cl_2$ three times. The combined extracts were dried over $MgSO_4$ and concentrated. The residue was chromatographed on silica gel ($CH_2Cl_2$/acetone=1/1) to give 116 mg of the object compound.

MS: 1274.32

Retention time: 6.2 minutes (purity: 95%; HPLC, column: Shiseido UG120 C18, 100 mm×4.6 mm ID, eluent: 60% MeCN/$H_2O$, flow rate: 1.0 ml/minute)

Prep 99

The object compound was prepared according to a similar manner to that of Prep 2.

MS: 1439.91

Prep 100

The object compound was prepared according to a similar manner to that of Prep 89.

MS: 1498.9

Prep 101

The object compound was prepared according to a similar manner to that of Prep 90.

MS: 1342.7

Prep 102

The object compound was prepared according to a similar manner to that of Prep 91.

MS: 1324.7

Prep 103

The object compound was prepared according to a similar manner to that of Prep 92.

MS: 1489.8

Prep 104

The object compound was prepared according to a similar manner to that of Prep 89.

MS: 1466.9

Prep 105

The object compound was prepared according to a similar manner to that of Prep 90.

MS: 1310.7

Prep 106

The object compound was prepared according to a similar manner to that of Prep 91.

MS: 1292.7

Prep 107

The object compound was prepared according to a similar manner to that of Prep 92.

MS: 1457.8

Prep 108

To a solution of the object compound of Prep 119 (500 mg) in pyridine (10 ml) was added dropwise acetic anhydride (154 µl), and the mixture was stirred at room temperature for overnight. The mixture was diluted with water and extracted with EtOAc. The organic phase was washed with water twice, dried over $MgSO_4$ and concentrated. The residue was chromatographed on silica gel (hexane/acetone=7/3) to give 116 mg of the object compound.

MS: 1535.01

Prep 109

The object compound was prepared according to a similar manner to that of Prep 121.

MS: 1306.79

Prep 110

The object compound was prepared according to a similar manner to that of Prep 2.

MS: 1471.84

Prep 111

The object compound was prepared according to a similar manner to that of Prep 119 (Iodoethane was used instead of paraformaldehyde).

MS: 1519.70

Prep 112

The object compound was prepared according to a similar manner to that of Prep 121.

MS: 1291.74

Prep 113

The object compound was prepared according to a similar manner to that of Prep 2.

MS: 1456.64

Prep 114

The object compound was prepared according to a similar manner to that of Prep 30.

MS: 1401.46

Prep 115

The object compound was prepared according to a similar manner to that of Prep 36.

MS: 1272.45

Prep 116

To a solution of the object compound of Prep 115 in THF (15 ml) were added water (0.2 ml) and $PPh_3$ (326 mg), and the mixture was heated at 70° C. for 2 hours. The mixture was cooled, concentrated and coevaporated with toluene. The residue was chromatographed on silica gel ($CH_2Cl_2$/MeOH=10/0 to 4/1) to give 461 mg of the object compound.

MS: 1247.84

Prep 117

To a solution of the object compound of Prep 116 (46 mg) in EtOH (10 ml) was added acetaldehyde (0.1 ml), and the mixture was stirred at room temperature for 0.5 hour. After concentrating to a 1/10 volume in vacuo, the mixture was diluted with EtOH (5 ml). Sodium borohydride (10 mg) was added in portions to the mixture, and the whole was stirred at room temperature for 0.5 hour. The reaction was quenched with aq. NaHCO$_3$ solution and extracted with CH$_2$Cl$_2$ six times. The combined extracts were dried over MgSO$_4$ and concentrated to give 33 mg of the object compound, which was used for the next step without further purification.

MS: 1275.83

Prep 118

To a solution of the compound (A) (10.0 g) and 1H-imidazole (5.5 g) in DMF (100 ml) was added tert-butylchlorodimethylsilane (9.8 g) at room temperature. After stirring for 21 hours at room temperature, the reaction mixture was poured into a mixture of EtOAc and water. The organic layer was successively washed with brine and dried over MgSO$_4$. The solvent was evaporated in vacuo and the residue was purified by column chromatography on silica gel eluting with a mixture of hexane and acetone (100:0→50:50). The eluted fractions containing the desired product were collected and evaporated in vacuo to give the object compound (11.5 g) as a colorless amorphous.

Prep 119

To a solution of N,N-diisopropylamine (4.8 ml) in THF (100 ml) was added dropwise 1.5 M n-butyllithium in hexane (4.8 ml) at −20° C. and the mixture was stirred for 5 minutes at the same temperature. After cooling to −78° C., a solution of the object compound of Prep 118 (5.0 g) in THF (20 ml) was added dropwise over 10 minutes to the mixture and the whole was stirred for 15 minutes. To the resulting yellow solution was added portions paraformaldehyde (616 mg) at the same temperature, and the mixture was gradually warmed up to room temperature. After stirring at room temperature for 1.5 hours, the reaction was quenched with water and extracted with EtOAc. The organic phase was dried over MgSO$_4$ and concentrated. The residue was chromatographed on silica gel (hexane/acetone=7/3) to give 2.20 g of the object compound as a mixture of the corresponding bishydroxymethylated compound, which was used for the next step without further purification.

MS: 1492.39

Retention time: 6.8 minutes (purity: 60%; HPLC, column: YMC-C8 AS-202, 150 mm×4.6 mm ID, eluent: 100% MeCN, flow rate: 1.0 ml/minute)

Prep 120

To a solution of the object compound of Prep 119 (101.7 g) CH$_2$Cl$_2$ (2.03 l) were added N,N,N',N'-tetramethylnaphthalene-1,8-diamine (87.6 g) and molecular sieves 3A (55 g). To this was added trimethyloxonium tetrafluoroborate (50.4 g) portionwise under ice cooling. And it was stirred at room temperature for 5 hours. After insoluble materials were filtered off, to filtrate was added sat. aq. NaHCO$_3$ solution and CH$_2$Cl$_2$ was evaporated off. The residue was extracted with EtOAc. The organic phase was washed with 5% citric acid aq. (×2), sat. aq. NaHCO$_3$ solution, and brine, dried over MgSO$_4$, filtered, and evaporated off. The residue was purified by silica gel column (CH$_2$Cl$_2$/acetone=CH$_2$Cl$_2$ only to 70/30) to give the object compound (51.8 g) as a white powder.

MS: 1507.00

Prep 121

To a solution of the object compound of Prep 120 (5.9 g) in MeOH (59 ml) was added 1 N HCl (29.5 ml) and the mixture was stirred at room temperature for 5 hours. After removal of methanol in vacuo, the residue was extracted by CH$_2$Cl$_2$. The extract was washed with brine, dried over MgSO$_4$ and concentrated in vacuo. The residue was purified by silica gel column (CH$_2$Cl$_2$:acetone=CH$_2$Cl$_2$ only to 50:50) to give the object compound (3.5 g) as a white powder.

The configuration at 3 position of this compound was determined to be (R) in comparison with the HPLC spectra of the authentic sample whose configuration at 3 position was confirmed to be (R), synthesized by alternative synthetic method as described below (Prep 158).

NMR: 0.70 (3H, d, J=6.7 Hz), 0.75 (1H, t, J=5.6 Hz), 0.81 (6H, d, J=6.4 Hz), 0.87 (3H, d, J=6.8 Hz), 0.89 (3H, d, J=6.8 Hz), 0.90 (3H, d, J=7.0 Hz), 0.93 (3H, d, J=6.2 Hz), 0.94 (3H, d, J=6.4 Hz), 0.97-1.03 (9H, m), 1.10 (3H, d, J=6.8 Hz), 1.12 (3H, d, J=7.0 Hz), 1.26 (3H, s), 1.30-1.36 (5H, m), 1.52-1.65 (2H, m), 1.66 (3H, d, J=5.5 Hz), 1.70-2.15 (4H, m), 2.15-2.22 (6H, m), 2.44 (1H, d, J=4.8 Hz), 2.63 (2H, s), 2.91 (3H, s), 3.01 (3H, s), 3.06 (3H, s), 3.08 (3H, s), 3.09 (3H, s), 3.17 (3H, s), 3.37 (6H, s), 3.44-3.51 (1H, m), 3.55 (1H, dd, J=6.4, 9.8 Hz), 3.59-3.63 (1H, m), 3.75 (2H, s), 4.17-4.31 (2H, m), 4.52 (1H, dd, J=7.0, 9.0 Hz), 4.70 (tH, 6.9), 4.75-4.89 (2H, m), 4.91-5.03 (3H, m), 5.08 (1H, dd, J=5.0, 10.1 Hz), 5.15 (1H, dd, J=4.2, 11.8 Hz), 5.27-5.56 (4H, m), 5.65 (1H, d, J=3.2 Hz), 6.76 (1H, d, J=7.7 Hz), 6.86 (1H, d, J=7.7 Hz), 7.00 (1H, d, J=9.2 Hz), 7.67 (1H, d, J=9.2 Hz), 8.92 (1H, d, J=9.4 Hz).

MS: 1278.63

Retention time: 5.0 minutes (HPLC, column: Shiseido UG120 C18, 100 mm×4.6 mm ID, eluent: 60% MeCN/H$_2$O, flow rate: 1.0 ml/minute)

Prep 122

To a stirred solution of the object compound of Prep 119 (13.5 g) in MeCN (270 ml) were added DMAP (9.94 g) and O-(4-fluorophenyl)chlorothiocarbonate (7.76 g), and the mixture was stirred for 4 hours. The solvent was removed under reduced pressure. The residue was diluted with EtOAc and washed with 1 N HCl, water, aq. NaHCO$_2$ solution and brine and dried over MgSO$_4$. Concentration under reduced pressure gave a residue, which was purified with silica gel column chromatography eluting with acetone/CH$_2$Cl$_2$=0/100→50/50 to give the object compound (6.04 g).

MS: 1647.16

Prep 123

The object compound was prepared according to a similar manner to that of Prep 92.

MS: 1413.34.

Prep 124

The object compound was prepared according to a similar manner to that of Prep 92.

MS: 1443.87.

Prep 125

To a solution of the compound (A) (20 g) in 1,2-dimethoxyethane (200 ml) was added 4-methylbenzenesulfonic acid (7.7 g) and the mixture was stirred at 50° C. for 14 hours. To the mixture was added 1 N NaOH and neutralized under ice bath cooling, and was added di-tert-butyl dicarbonate (8.8 g). The pH value of the mixture was adjusted to 8 with 1 N NaOH under ice bath cooling. The mixture was stirred at ambient temperature for 2.5 hours. Resulting mixture was concentrated in vacuo and extracted with EtOAc. The organic phase was washed with sat. aq. sodium carbonate solution, 0.1 N HCl, and brine, and dried over sodium sulfate. Solvent was removed in vacuo to give the object compound (12.2 g) as brown foam. Obtained crude product was used in next reaction without further purification.

MS: 1334.7

Prep 126

To a solution of the object compound of Prep 125 (5.1 g) in MeOH (50 ml) was added sodium methoxide (1.24 g) in MeOH (50 ml) and the mixture was stirred for 14 hours. To the mixture was added 10% citric acid aqueous solution, extracted with EtOAc. The organic phase was washed with brine, and dried over sodium sulfate. Solvent was removed in vacuo to give brown form. Obtained crude product was purified by silica gel chromatography (CH$_2$Cl$_2$:acetone=60:40) to give the object compound (5.23 g).

MS: 1366.7

Prep 127

To a solution of the object compound of Prep 126 (6.3 g) in CH$_2$Cl$_2$ (64 ml) was added 2,4,6-trimethylpyridine (1.24 g) and acetyl chloride (0.5 ml) the mixture was stirred for 14 hours. The mixture was diluted with CH$_2$Cl$_2$ and washed with 10% citric acid aqueous solution, and brine, and dried over sodium sulfate. Solvent was removed in vacuo to give as the object compound (6.28 g).

MS: 1408.70

Prep 128

To a solution of the object compound of Prep 127 (6.28 g) was dissolved in 10% trifluoroacetic acid in CH$_2$Cl$_2$ (63 ml) under ice-bath cooling. After being stirred at the same temperature for 2 hours, to the reaction solution was added 1 M aq. NaHCO$_3$ solution to be pH 8. The reaction mixture was extracted with CHCl$_3$ and the organic layer was washed with sat. aq. NaHCO$_3$ solution and brine, dried over MgSO$_4$, and concentrated in vacuo to give the object compound (5.65 g).

MS: 1308.69

Prep 129

To a solution of the object compound of Prep 128 (3 g) in MeCN (45 ml) was added isothiocyanatobenzene (0.41 ml) at ambient temperature, and the pH value of the mixture was added to 7.5 with DIPEA (0.12 ml). The reaction mixture was stirred at ambient temperature for 1.5 hours. To the resulting solution was added N,N-dimethylpropanediamine (0.19 ml) and stirred for 5 minutes, then added 1 N HCl (45 ml) and the mixture was stirred at 30° C. for 2 hours. The resulting mixture was neutralized with sodium carbonate solution (3.8 g in H$_2$O 100 ml), and concentrated in vacuo. The pH value of residual solution was adjusted 8 with saturated aq. NaHCO$_3$ solution, and the solution was extracted with EtOAc. The organic phase was washed with sat. aq. NaHCO$_3$ solution and brine, and dried over sodium sulfate. Solvent was removed in vacuo to give the object compound (1.82 g).

MS: 1207.58

Prep 130

To a solution of the object compound of Prep 129 (1.58 g) in MeCN (23 ml) was added isothiocyanatobenzene (0.23 ml) at ambient temperature, and the pH value of the mixture was added to 7.5 with diisopropylethylamine (0.068 ml). The reaction mixture wad stirred at ambient temperature for 1.5 hours. To the resulting solution was added N,N-dimethylpropanediamine (0.33 ml) and stirred for 5 minutes, then added 1 N HCl (23 ml) and the mixture was stirred at 30° C. for 2 hours. The resulting mixture was neutralized with sodium carbonate solution (3.8 g in H$_2$O 100 ml), and concentrated in vacuo. The pH value of residual solution was adjusted 8 with sat. aq. NaHCO$_3$ solution, and the solution was extracted with EtOAc. The organic phase was washed with sat. aq. NaHCO$_3$ solution and brine, and dried over sodium sulfate. Solvent was removed in vacuo to give the object compound (1.1 g) as pale yellow foam.

MS: 1136.5

Prep 131

To a solution of the object compound of Prep 130 (390 mg) was added N-(tert-butoxycarbonyl)-N-ethyl-D-alanine (149 mg), bis(2-oxo-3-oxazolidinyl)phosphinic chloride (262 mg), and diisopropylethylamine (358 μl) under ice bath cooling. The mixture was stirred for 13 hours at ambient temperature, and extracted with EtOAc. The organic phase was washed with 10% citric acid aqueous solution, sat. aq. NaHCO$_3$ solution, and brine, and dried over sodium sulfate. Solvent was removed in vacuo, and the residue was dissolved in 10% trifluoroacetic acid in CH$_2$Cl$_2$ (5.7 ml) under ice-bath cooling. After being stirred at the same temperature for 2 hours, to the reaction solution was added 1 M aq. NaHCO$_3$ solution to be pH 8. The reaction mixture was extracted with CHCl$_3$ (50 ml) and the organic layer was washed with sat. aq. NaHCO$_3$ solution and brine, dried over MgSO$_4$, and concentrated in vacuo to give the object compound (0.38 g).

MS: 1235.6

Prep 132

To a solution of the object compound of Prep 131 (106 mg) was added 1-hydroxy-7-azabenzotriazole (23 mg), N-(tert-butoxycarbonyl)-L-threonyl-N-ethyl-D-alanine (37.6 mg) and O-(7-Azabenzotriazol-1-yl)-N,N,N',N'-tetramethyluronium hexafluorophosphate (65 mg) and diisopropylethylamine (276 μl) under ice bath cooling. The mixture was stirred for 13 hours at ambient temperature, and extracted with EtOAc. The organic phase was washed with 10% citric acid aqueous solution, sat. aq. NaHCO$_3$ solution, and brine, and dried over sodium sulfate. Solvent was removed in vacuo, and the residue was purified by preparative thin layer chromatography (CHCl$_3$:MeOH=90:10) to give the object compound (0.13 g).

MS: 1436.86

Prep 133

To a solution of the object compound of Prep 132 (130 mg) was dissolved in 10% trifluoroacetic acid in CH$_2$Cl$_2$ (2.6 ml) under ice-bath cooling. After being stirred at the same temperature for 2 hours, to the reaction solution was added 1 M aq. NaHCO$_3$ solution to be pH 8. The reaction mixture was extracted with CHCl$_3$ (50 ml) and the organic layer was washed with sat. aq. NaHCO$_3$ solution and brine, dried over MgSO$_4$, and concentrated in vacuo. The resulting residue in THF (1.5 ml) was added 1 N NaOH (0.015 ml) at ambient temperature and the mixture was stirred for 2 hours. To the reaction mixture was added 10% citric acid aqueous solution to adjust pH=4, and the solution was extracted with EtOAc. The organic phase was washed with brine, and was dried over sodium sulfate. Solvent was removed in vacuo and the residue was triturated with Et$_2$O to give the object compound (0.1 g).

MS: 1280.7

Prep 134

To a solution of the object compound of Prep 133 (100 mg) in CH$_2$Cl$_2$ (80 ml) was added 1-hydroxy-7-azabenzotriazole (21 mg) and WSC (30 mg) under ice bath cooling, and the mixture was stirred at 5° C. for 13 hours. The reaction mixture was concentrated in vacuo and the residue was extracted with EtOAc. The organic phase was washed with water, 10% citric acid aqueous solution, sat. aq. NaHCO$_3$ solution, and brine, and was dried over sodium sulfate. Solvent was removed in vacuo, and the residue was purified by preparative thin layer chromatography (CHCl$_3$:MeOH=95:5) to give the object compound (46 mg).

MS: 1262.66

Prep 135

To a solution of the object compound of Prep 134 (46 mg) in CH$_2$Cl$_2$ (1 ml) were added 4-nitrophenyl chloroformate (14 mg) and N-methylmorpholine (9 μl). After the mixture was stirred for overnight. After the starting compound was consumed, the mixture was diluted with EtOAc, washed with 1 N aq. HCl and aq. NaHCO$_3$ solution, dried over MgSO$_4$ and concentrated. The residue was chromatographed on silica gel (hexane/EtOAc=¼ and then CH$_2$Cl$_2$/MeOH=9/1) to give the object compound (50 mg).
MS: 1427.2

Prep 136

The object compound, which was used in the next step without further purification, was prepared according to a similar manner to that of Prep 92 then Ex 74 continuously.

Prep 137

The object compound was prepared according to a similar manner to that of Prep 81.
MS: 1478.51.

Prep 138

The object compound was prepared according to a similar manner to that of Prep 82.
MS: 1593.65.

Prep 139

The object compound was prepared according to a similar manner to that of Prep 84 then Prep 85 continuously.
MS: 1629.09.

Prep 140

The object compound was prepared according to a similar manner to that of Prep 86 then Prep 85 continuously.
MS: 1528.13.

Prep 141

The object compound was prepared according to a similar manner to that of Prep 86.
MS: 1322.04

Prep 142

The object compound was prepared according to a similar manner to that of Prep 89.
MS: 1628.88.

Prep 143

The object compound, which was used for the next step without further purification, was prepared according to a similar manner to that of Prep 90 (NaOH was used instead of lithium hydroxide).

Prep 144

The object compound was prepared according to a similar manner to that of Prep 89.
ESI MS (M+2H$^+$)/2: 822.10

Prep 145

The object compound was prepared according to a similar manner to that of Prep 90 (NaOH was used instead of lithium hydroxide).
MS: 1407.02.

Prep 146

To a solution of the object compound of Prep 118 (5.0 g) and MeI (426 µl) in DMF (100 ml) was added NaH (273 mg) under ice cooling. After stirring for 3 hours under ice cooling, the reaction mixture was poured into a mixture of EtOAc and water. The organic layer was successively washed with brine and dried over MgSO$_4$. The solvent was evaporated in vacuo and the residue was purified by column chromatography on silica gel eluting with a mixture of hexane and EtOAc (100:0→50:50). The eluted fractions containing the desired product were collected and evaporated in vacuo to give the object compound (4.23 g) as a colorless amorphous.
MS: 1477.09

Prep 147

The object compound was prepared according to a similar manner to that of Prep 119.
MS: 1507.10

Prep 148

The object compound was prepared according to a similar manner to that of Prep 120.
MS: 1538.27

Prep 149

The object compound was prepared according to a similar manner to that of Prep 121.
MS: 1292.99

Prep 150

The object compound was prepared according to a similar manner to that of Prep 92.
MS: 1457.99

Prep 151

The object compound was prepared according to a similar manner to that of Prep 89.
MS: 1437.07

Prep 152

The object compound was prepared according to a similar manner to that of Prep 157.
MS: 1336.78

Prep 153

The object compound was prepared according to a similar manner to that of Prep 90.
MS: 1280.82

Prep 154

The object compound was prepared according to a similar manner to that of Prep 91.
MS: 1262.27
Retention time: 5.9 minutes
(HPLC, column: Shiseido UG120 C18, 100 mm×4.6 mm ID, eluent: 60% MeCN/H$_2$O, flow rate: 1.0 ml/minute)

Prep 155

The object compound was prepared according to a similar manner to that of Prep 89.
MS: 1452.90

Prep 156

To a solution of the object compound of Prep 155 (46 mg) in CH$_2$Cl$_2$ (1.6 ml) was added trifluoroacetic acid (0.4 ml) at 0° C., and the mixture was stirred at the same temperature for 3 hours. The mixture was diluted with water, adjusted to pH=9 with aq. NaHCO$_3$ solution and extracted with CH$_2$Cl$_2$ three times. The combined extracts were dried over MgSO$_4$ and concentrated to give the object compound (31 mg).
MS: 1352.82

Prep 157

The object compound was prepared according to a similar manner to that of Prep 90.
MS: 1296.29

Prep 158

The object compound was prepared according to a similar manner to that of Prep 91.
MS: 1278.29
Retention time: 5.0 minutes
(HPLC, column: Shiseido UG120 C18, 100 mm×4.6 mm ID, eluent: 60% NeCN/H$_2$O, flow rate: 1.0 ml/minute)

Ex 1

To a solution of the object major compound of Prep 2 (50 mg) in DMF (1 ml) was added morpholine (16 µl), and the mixture was stirred at room temperature for overnight. The mixture was submitted to ODS purification to give 35 mg of the object compound.

Ex 12

To a solution of the object major compound of Prep 2 (50 mg) in DMF (2 ml) was added N-ethylmethylamine (15 µl) and the mixture was stirred at room temperature for 1 hour. The reaction was quenched with aq. NaHCO$_3$ solution and extracted with EtOAc. The organic phase was washed with aq. NaHCO$_3$ solution twice, dried over MgSO$_4$ and concentrated. The residue was chromatographed on silica gel (CH$_2$Cl$_2$/MeOH=95/5 to 90/10) to give 46 mg of the object compound.

Ex 18

To a solution of the object major compound of Prep 2 (50 mg) in DMF (0.4 ml) were added 5,6,7,8-tetrahydroimizazo[1,2-a]pyrazine dihydrochloride (21 mg) and DIPEA (31 µl), and the mixture was stirred at room temperature for overnight. The mixture was submitted to ODS purification to give 33 mg of the object compound.

Ex 21

To a solution of the object compound of Ex 40 (its structure is in the Table 3) (379 mg) in EtOAc was added dropwise 4 N hydrogen chloride in dioxane, and the mixture was stirred at room temperature for 1.5 hour. The mixture was basified with aq. NaHCO$_3$ solution and extracted with CH$_2$Cl$_2$ three times. The combined extracts were dried over MgSO$_4$ and concentrated. The residue was submitted to ODS purification to give 92 mg of the object compound.

Ex 22

To a solution of the object compound of Ex 41 (73 mg) in DMF (3 ml) were added (dimethylamino)acetic acid (20 mg), O-(7-azabenzotriazol-1-yl)-N,N,N',N'-tetramethyluronium hexafluorophosphate (31 mg) and DIPEA (30 µl) in sequence, and the mixture was stirred at room temperature for 1 hour. The mixture was diluted with EtOAc, washed with H$_2$O three times, dried over MgSO$_4$ and concentrated. The residue was chromatographed on silica gel (CH$_2$Cl$_2$/MeOH=100/0 to 95/5) to give 57 mg of the object compound.

Ex 34

To a solution of the object compound of Ex 13 (its structure is in the Table 1) (184 mg) in a mixed solvent of CH$_2$Cl$_2$ (8 ml) and MeOH (2 ml) were added 35% formaldehyde aqueous solution (90 µl) and sodium triacetoxyborohydride (85 mg) in sequence, and the mixture was stirred at room temperature for 2.5 hours. The mixture was basified with sat. aq. NaHCO$_3$ solution and extracted with CH$_2$Cl$_2$ three times. The combined extracts were dried over MgSO$_4$ and concentrated. The residue was chromatographed on silica gel (CH$_2$Cl$_2$:MeOH=100:0 to 90:10) to give 180 mg of the object compound.

Ex 43

To a solution of the object compound of Prep 28 (38 mg) and morpholine (10 µl) in CH$_2$Cl$_2$ was added sodium triacetoxyborohydride (30 mg), and the mixture was stirred at room temperature for 3 hours. The reaction was quenched with aq. NaHCO$_3$ solution and extracted with CH$_2$Cl$_2$ three times. The combined extracts were dried over MgSO$_4$ and concentrated. The residue was submitted to ODS purification to give 20 mg of the object compound.

Ex 44

The mixture of the object compound of Prep 32 (90 mg) in EtOH (1.8 ml) was treated with 1 N HCl (600 µL) at room temperature for 12 hours. The reaction mixture was concentrated in vacuo. The residue was chromatographed on silica gel (acetone:n-hexane=1:9 to 1:1) to give 55.8 mg of the object compound.

Ex 45

The mixture of the object compound of Prep 35 (125 mg) in EtOH (2.1 ml) was treated with 6 N HCl (700 µl) at room temperature for 12 hours. The reaction mixture was concentrated in vacuo. The residue was chromatographed on silica gel (acetone:n-hexane=1:9 to 1:1) to give 107 mg of the object compound.

Ex 46

The mixture of the object compound of Prep 38 (57 mg) in MeOH (2.1 ml) was treated with 6 N HCl (0.7 ml) at room temperature for 30 minutes. The reaction mixture was poured into a solution of sodium borohydride (18 mg) in EtOH (1.2 ml) at 0° C. To the mixture was added TEA (200 µl) and the solution was concentrated. The residue was chromatographed on silica gel (MeOH:CH$_2$Cl$_2$ (0.2% TEA)=0:100 to 1:9) to give 46 mg of the object compound.

Ex 47

The mixture of the object compound of Prep 33 (64 mg) in EtOH (1.8 ml) was treated with 1 N HCl (600 µl) at room temperature for 12 hours. After treated with TEA (100 µl), the mixture was concentrated. The residue was purified by preparative HPLC (MeCN:water=40:60 to 25:75) to give 44.5 mg of the object compound.

Ex 48

The mixture of the object compound of Prep 30 (69.4 mg) in DMF (1.0 ml) was treated with sodium 1,2,3-thiadiazole-5-thiolate (27 mg) at room temperature for 12 hours. After treated with acetic acid (10 µl), the mixture was concentrated. The residue was purified by preparative HPLC (CapcellPak UG; MeCN/water=2/8 to 7/3) to give 53.7 mg of the object compound.

Ex 49

The mixture of the object compound of Prep 30 (694 mg) in DMF (10 ml) was treated with thiobenzoic acid (207 mg) and potassium carbonate (207 mg) at room temperature for 12 hours. After treated with acetic acid (70 µl), the mixture was concentrated. The residue was chromatographed on silica gel (acetone:n-hexane=1:9 to 45:55) to give 607 mg of the object compound.

Ex 50

The mixture of the object compound of Ex 49 (68 mg) in EtOH (1.3 ml) was treated with 2.6 M sodium ethoxide in EtOH (29 µl) at room temperature for 30 minutes. To the solution was added benzyl bromide (18 µl). After stirred for 1 hour, the mixture was treated with acetic acid (10 µl). The mixture was concentrated and the residue was chromatographed on silica gel (acetone:n-hexane=1:9 to 45:55) to give 59.8 mg of the object compound.

Ex 51

To the mixture of the object compound of Prep 34 (64 mg) in CH$_2$Cl$_2$ (0.5 ml) was added 1.0 M dimethylaminopyridine/

$CH_2Cl_2$ (100 μl), and 1.0 M 4-nitrophenyl chloroformate in $CH_2Cl_2$ (100 μl) at 0° C. After stirred at 0° C. for 30 minutes, the mixture was treated with morpholine (44 μl) at room temperature for 30 minutes. To the mixture was added acetic acid (30 μl), and the solution was concentrated. The residue was purified by preparative HPLC (CapcellPak UG; MeCN/water=2/8 to 7/3) to give 36.3 mg of the object compound.

Ex 54

To a solution of the object compound of Prep 39 (37 mg), 4-methoxybenzoic acid (23 mg), and 1-hydroxybenzotriazole (24 mg) in N-methyl pyrrolidinone (0.6 ml) were added DIPEA (21 μl) and ethyl WSC hydrochloride (29 mg), and the mixture was stirred at room temperature for 4 hours. The mixture was diluted with EtOAc, washed with water and brine, dried over $MgSO_4$ and concentrated. The residue was chromatographed on silica gel (MeOH:$CH_2Cl_2$ (0.2% TEA) =2:98 to 8:92) to give 36 mg of the object compound.

Ex 64

To a solution of the object compound of Prep 22 (200 mg) in MeCN (5 ml) were added (trimethylsilyl)diazomethane (2.0 M in hexane; 0.2 ml) and 42% aqueous tetrafluoroboric acid solution (22 μl) in sequence at 0° C. Six further portions of (trimethylsilyl)diazomethane (2.0 M in hexane; 0.2 ml) and 42% aqueous tetrafluoroboric acid solution (22 μl) were added at intervals of 20 minutes at the same temperature. After stirring for 6 hours, the reaction was quenched with sat. aq. $NaHCO_3$ solution and extracted with EtOAc. The extract was washed with water three times, dried over $MgSO_4$ and concentrated. To a suspension of the residue in MeOH was added 1 N aq. NaOH solution (5 ml). After stirring at room temperature for overnight, the mixture was extracted with $CH_2Cl_2$ three times. The combined extracts were dried over $MgSO_4$ and concentrated. The residue was submitted to ODS purification to give 22 mg of the object compound.

Ex 66

To a solution of the object compound of Prep 27 (42 mg) in DMF (3 ml) was added morpholine (13 μl), and the mixture was stirred at 60° C. for 6 hours. The reaction was quenched with water and extracted with EtOAc. The extract was washed with water twice, dried over $MgSO_4$ and concentrated. The residue was chromatographed on silica gel ($CH_2Cl_2$:acetone=2:3 to 0:100) to give 23 mg of the object compound.

Ex 67

To a solution of the object compound of Prep 41 (50 mg) in DMSO (2 ml) was added the object compound of Prep 65 (23 mg), and the mixture was stirred at 40° C. for 12 hours. The reaction was quenched with water and extracted with EtOAc. The extract was washed with water twice, dried over $MgSO_4$ and concentrated. The residue was purified by reversed phase preparative HPLC (YMC Pack pro C8; MeCN:water=75:25) to give 40 mg of the object compound.

Ex 74

To a solution of the object compound of Prep 92 (20 mg) in THF (0.5 ml) was added (2-Methoxyethyl)methylamine (5 μL) and the mixture was stirred at room temperature for 3 hours. The reaction was quenched with potassium carbonate aqueous solution and extracted with EtOAc. The organic phase was washed with aq. $NaHCO_3$ solution, dried over $MgSO_4$ and concentrated. The residue was purified by silica gel column ($CH_2Cl_2$:acetone=75:25 to 60:40) to give the object compound (18 mg) as a white powder.

Ex 80

To a solution of the object compound of Ex 78 (32 mg) in MeOH (5 ml) was added sodium methoxide (2 mg), and the mixture was stirred at room temperature for 1 hour. The mixture was diluted with water and extracted with $CH_2Cl_2$ three times. The combined extracts were dried over $MgSO_4$ and concentrated to give the object compound (27 mg).

Ex 82

To a solution of the object compound of Prep 124 (30 mg) in DMF (1 ml) was added morpholine (20 μl), and the mixture was stirred at room temperature for 0.5 hour. The mixture was submitted purified to ODS column chromatographypurification to give 18 mg of the object compound.

Ex 98

To a solution of the object compound of Prep 92 (42 mg) in DMF (1.0 ml) was added (3R,5S)-3,5-dimethylmorpholine hydrochloride (90 mg), DIPEA (160 μl) and the mixture was stirred at room temperature for 3 hours. The reaction was quenched with potassium carbonate aqueous solution and extracted with EtOAc. The organic phase was washed with aq. $NaHCO_3$ solution, dried over $MgSO_4$ and concentrated. The residue was purified by silica gel column chromatography ($CH_2Cl_2$:acetone=75:25 to 60:40) to give the object compound (7 mg) as a white powder.

Ex 102

A solution of the object compound of Ex 76 (15 mg) in MeOH (1 ml) was hydrogenated over 10% Pd/C (50% wet; 5 mg) at room temperature for 5 hours. The mixture was filtered and filtrate was evaporated to give the object compound (10 mg) as a white powder.

Ex 204

A solution of 1,1,1,3,3,3-hexamethyl-2-(trimethylsilyl)trisilane (755 mg) in toluene (20 ml) was heated up to 120° C., and the mixture of the object compound of Prep 122 (1.0 g) and α,α'-azobisisobutyronitrile (99.7 mg) in toluene (10 ml) was added dropwise with stirring. The whole was stirred for 1 hour at the same temperature, and cooled to room temperature. The solvent was removed under reduced pressure. Then the residue was dissolved in MeOH (10 ml), and 1 N HCl (4.25 ml) was added. The mixture was stirred at room temperature for overnight. The whole was adjusted basic with aq. $NaHCO_3$ solution and extracted with $CH_2Cl_2$ (three times). The combined extracts were dried over $MgSO_4$ and concentrated under reduced pressure. The residue was purified with silica gel column chromatography eluting with acetone:$CH_2Cl_2$=0:100 to 50:50 to give the object compound (360 mg).

The configuration at 3 position of this compound was determined to be (R) in comparison with the HPLC spectra of the authentic sample whose configuration at 3 position was confirmed to be (R), synthesized by alternative synthetic method as described above (Prep 91).

Ex 205

To a solution of the object compound of Ex 204 (150 mg), molecular sieves, 3 Å (powder, 0.3 g) and N,N,N',N'-tetramethylnaphthalene-1,8-diamine (103 mg) in CH$_2$Cl$_2$ (10 ml) was added in portions trimethyloxonium tetrafluoroborate (35 mg) at 0° C., and the mixture was stirred at the same temperature for 1.5 hours. The reaction was quenched with aq. NaHCO$_3$ solution and extracted with EtOAc. The organic extract was washed with 1 N aq. HCl solution, dried over MgSO$_4$ and concentrated. The residue was submitted to ODS purification to give 32 mg of the object major compound (Ex 205-A) and 7 mg of the object minor compound (Ex 205-B).

Ex 207

To a solution of the object compound of Prep 117 (46 mg) in a mixed solvent of THF (5 ml) and sat. aq. NaHCO$_3$ solution (1 ml) was added isopropyl chlorocarbonate (15 μl), and the mixture was stirred at room temperature for 30 minutes. The mixture was diluted with water, extracted with CH$_2$Cl$_2$ three times. The combined extracts were dried over MgSO$_4$ and concentrated. The residue was submitted to ODS purification to give 18 mg of the object compound.

Ex 210

To a solution of the object compound of Prep 117 (50 mg) in CH$_2$Cl$_2$ were added DIPEA (100 μl) and dimethylcarbamic chloride (50 μl), and the mixture was stirred at room temperature for overnight. The mixture was diluted with water, extracted with EtOAc. The combined extracts were dried over MgSO$_4$ and concentrated. The residue was submitted by ODS purification to give 18 mg of the object compound.

Ex 233

To a solution of the object compound of Prep 135 (50 mg) in DMF (1 ml) was added morpholine (30 μl), and the mixture was stirred at room temperature for overnight. The reaction was quenched with potassium carbonate aqueous solution and extracted with EtOAc. The organic phase was washed with aq. NaHCO$_3$ solution, dried over MgSO$_4$ and concentrated. The residue was purified by silica gel column chromatography (CH$_2$Cl$_2$:acetone=75:25 to 60:40) to give the object compound (13 mg) as a white powder.

Ex 238

A solution of the object compound of Ex 21 (its structure is in the Table 2) (111 mg) in MeOH was hydrogenated over 20% Pd/C (50% wet; 20 mg) at room temperature for 1.5 hours. The mixture was filtered and the filtrate was concentrated. The residue was chromatographed on silica gel (CH$_2$Cl$_2$:MeOH=97:3 to 90:10) to give 108 mg of the object compound.

Ex 259

A solution of the object compound of Ex 227 (38 mg) in MeOH was hydrogenated over 10% Pd/C (50% wet; 20 mg) at room temperature for 1.5 hours. The mixture was filtered and the filtrate was concentrated. The residue was dissolved in CH$_2$Cl$_2$, dried over MgSO$_4$, filtered and concentrated to give 35 mg of the object compound.

The structure, the Data [physical data; MS: ESI (M+H)$^+$ unless otherwise indicated, NMR: the peak δ(ppm) of $^1$H-NMR data (chloroform-d as a solvent for measurement unless otherwise indicated using (CH$_3$)$_4$Si as internal reference)] and the Syn [Process for production (the number indicates the Example number corresponding to the production)] for the Example compounds are shown in the Tables below. And the structure for the compounds of Preparations 2, 21~41 and 80~158 are also shown in the Tables below.

TABLE 1

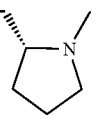

| Ex | Syn | E |
|---|---|---|
| 1 | — | 4-Mor- |
| 2 | 1 | (Me)$_2$N—(CH$_2$)$_2$—NH— |
| 3 | 1 | 4-Mor-(CH$_2$)$_2$—NH— |
| 4 | 1 | 4-Mor-(CH$_2$)$_2$—N(Me)- |
| 5 | 1 | (4-Py)-CH$_2$—NH— |
| 6 | 1 | [4-(2-Py)-1-Pipa]- |
| 7 | 1 | MeO—(CH$_2$)$_2$—N(Me)- |
| 8 | 1 | (4-Me-1-Pipa)- |
| 9 | 12 | CF$_3$—CH$_2$—NH— |
| 10 | 12 | [MeO—(CH$_2$)$_2$]$_2$N— |
| 11 | 12 | [(2R,6S)-2,6-(Me)$_2$-4-Mor]- |
| 12 | — | Et-N(Me)- |
| 13 | 1 | [(Et)$_2$N—(CH$_2$)$_2$]$_2$N— |
| 14 | 1 | {4-[Et-S(O)$_2$]-1-Pipa}- |
| 15 | 1 | {4-[(4-Mor)-C(O)—CH$_2$]-1-Pipa}- |
| 16 | 1 | MeO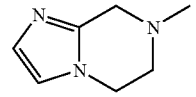 |
| 17 | 1 | (2-Py)-(CH$_2$)$_2$—N(Me)- |
| 18 | — | 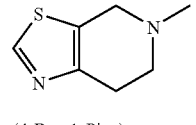 |
| 19 | 18 | 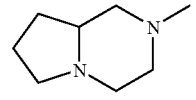 |
| 20 | 12 | (4-Boc-1-Pipa)- |
| 21 | — | 1-Pipa- |
| 22 | — | {4-[(Me)$_2$N—CH$_2$—C(O)]-1-Pipa}- |
| 23 | 1 | (structure shown) |
| 24 | 18 | [(3S,5S)-3,5-(Me)$_2$-4-Mor]- |
| 25 | 18 | [(3R,5S)-3,5-(Me)$_2$-4-Mor]- |

TABLE 1-continued

[Structure: cyclic peptide with E—O—CH2—... substituent]

| Ex | Syn | E |
|----|-----|---|
| 26 | 12 | [4-methyl-3,4-dihydro-2H-pyrido[3,2-b][1,4]oxazinyl] |
| 27 | 12 | [morpholinyl-azetidinyl-N-Me] |
| 28 | 18 | [3,3-(Me)₂-4-Mor]- |
| 29 | 1 | [1-Me-4-(N(Me)(Et))-pyrazolyl] |
| 30 | 18 | [(3R,5R)-3,5-(Me)₂-4-Mor]- |
| 31 | 1 | [1-(MeOCH₂CH₂)-4-N(Me)₂-pyrazolyl] |
| 32 | 18 | [(2R,6R)-2,4,6-(Me)₃-1-Pipa]- |
| 33 | 12 | [(3R,5S)-3,5-(Me)₂-1-Pipa]- |
| 34 | — | [(3R,5S)-3,4,5-(Me)₃-1-Pipa]- |
| 35 | 18 | [(2R,6S)-2,4,6-(Me)₃-1-Pipa]- |
| 36 | 1 | [1-(2-morpholinoethyl)-4-N(Me)₂-pyrazolyl] |
| 37 | 1 | (4-Py)-N(Me)- |
| 38 | 1 | (2-Py)-N(Me)- |
| 39 | 1 | (3-Py)-N(Me)- |
| 40 | 1 | (1-Me-4-Pyr)-CH₂—N(Me)- |
| 41 | 1 | Ph-N(Me)- |
| 42 | 1 | [2-(N(Me)₂)-thiazolyl] |

TABLE 2

[Structure: cyclic peptide with A— substituent]

| Ex | Syn | A |
|----|-----|---|
| 43 | — | 4-Mor- |
| 44 | — | Ph-S— |
| 45 | — | {[2,4-(F)₂]-Ph}-O— |
| 46 | — | Bn-NH— |
| 47 | — | Ph-S(O)₂— |
| 48 | — | [5-(SMe)-1,2,3-thiadiazolyl] |
| 49 | — | Ph-C(O)—S— |
| 50 | — | Bn-S— |
| 51 | — | Mor-C(O)—S— |
| 52 | 51 | (1-Me-4-Pipa)-C(O)—S— |
| 53 | 51 | MeO—(CH₂)₂—N(Me)-C(O)—S— |
| 54 | — | (4-MeO-Ph)-C(O)—NH— |
| 55 | 54 | (3-MeO-Ph)-C(O)—NH— |
| 56 | 54 | [4-(Me)₂N-Ph]-C(O)—NH— |
| 57 | 50 | [4-(Et)₂N-Ph]-C(O)—CH₂—S— |
| 58 | 50 | (3-MeO-Ph)-CH₂—S— |
| 59 | 50 | [4-(Ac—NH)-Ph]-CH₂—S— |
| 60 | 51 | {4-[4-Mor-C(O)—CH₂]-1-Pipa}-C(O)—S— |
| 62 | 54 | [4-(4-Mor)-Ph]-C(O)—NH— |
| 63 | 43 | (3-Py)-CH₂—N(Me)- |
| 64 | — | MeO— |
| 65 | 1 | 4-Mor-C(O)—O—(CH₂)₂—O— |
| 66 | — | 4-Mor-(CH₂)₂—O— |
| 67 | — | [2,2-(MeO—CH₂)₂]-4-Mor- |
| 68 | 67 | [(2R)-2-(MeO—CH₂)]-4-Mor- |
| 69 | 67 | 1-Pip- |
| 70 | 67 | Bn-N(Me)- |
| 71 | 67 | MeO—(CH₂)₂—N(Me)- |
| 72 | 67 | [MeO—(CH₂)₂]₂N— |

TABLE 3

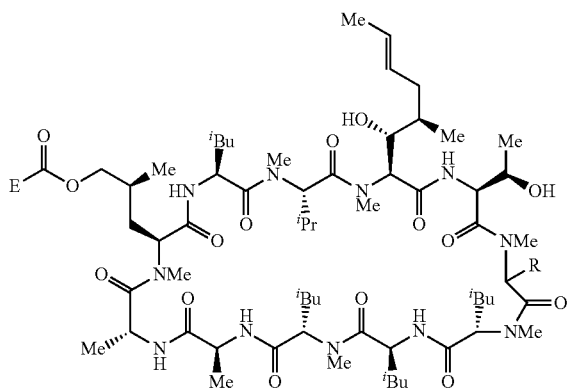

| Ex | Syn | E | R |
|---|---|---|---|
| 73 | 204 | (4-Me-Pipa)- | ⋯⋯Me |
| 74 | — | MeO—(CH$_2$)$_2$—N(Me)- | ⋯⋯Me |
| 75 | 74 | (4-Py)-N(Me)- | ⋯⋯Me |
| 76 | 74 | 4-Mor- | ⋯⋯Me |
| 77 | 98 | (1-Me-4-Py)-N(Me)- | ⋯⋯Me |
| 78 | 82 | (4-Me-1-Pipa)- | ⋯⋯CH$_2$OAc |
| 79 | 82 | 4-Mor- | ⋯⋯CH$_2$OAc |
| 80 | — | (4-Me-1-Pipa)- | ⋯⋯CH$_2$OH |
| 81 | 80 | 4-Mor- | ⋯⋯CH$_2$OH |
| 82 | — | 4-Mor- | ⋯⋯CH$_2$OMe |
| 83 | 82 | (4-Me-1-Pipa)- | ⋯⋯CH$_2$OMe |
| 84 | 82 | MeO—(CH$_2$)$_2$N(Me)- | ⋯⋯CH$_2$OMe |
| 85 | 82 | (Me)$_2$N— | ⋯⋯CH$_2$OMe |
| 86 | 74 | [(2R,6S)-2,6-(Me)$_2$-4-Mor]- | ⋯⋯Me |
| 87 | 74 | [MeO—(CH$_2$)$_2$]$_2$N— | ⋯⋯Me |
| 88 | 98 | 4-Mor-(CH$_2$)$_2$—N(Me)- | ⋯⋯Me |
| 89 | 74 | MeO—(CH$_2$)$_2$-Pipa | ⋯⋯Me |
| 90 | 82 | 4-Mor- | ⋯⋯Et |
| 91 | 82 | (4-Me-1-Pipa)- | ⋯⋯Et |
| 92 | 82 | MeO—(CH$_2$)$_2$—N(Me)- | ⋯⋯Et |
| 93 | 82 | (Me)$_2$N— | ⋯⋯Et |
| 94 | 82 | 4-Mor- | ⋯⋯CH$_2$CH=CH$_2$ |
| 95 | 82 | (4-Me-1-Pipa)- | ⋯⋯CH$_2$CH=CH$_2$ |
| 96 | 98 | [(3R,5S)- 3,4,5-(Me)$_3$-1-Pipa]- | ⋯⋯Me |
| 97 | 98 | [(2R,6S)-2,4,6-(Me)$_3$-1-Pipa]- | ⋯⋯Me |
| 98 | — | [(3R,5S)-3,5-(Me)$_2$-4-Mor]- | ⋯⋯Me |
| 99 | 98 | [(3R,5R)-3,5-(Me)$_2$-4-Mor]- | ⋯⋯Me |

TABLE 3-continued
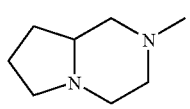
| Ex | Syn | E | R |
|---|---|---|---|
| 100 | 98 | [(3S,5S)-3,5-(Me)₂-4-Mor]- | ·······Me |
| 101 | 98 | [(2R,6S)-2,4,6-(Me)₃-1-Pipa]- | ·······Me |
| 103 | 74 | 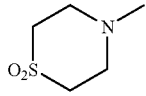<br>epimer mix | ·······Me |
| 104 | 74 | 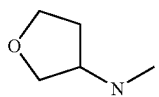 | ·······Me |
| 105 | 98 | [4-ⁿBu-4-MeO-1-Pip]- | ·······Me |
| 106 | 98 | 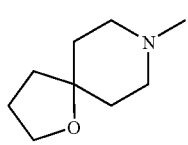<br>epimer mix | ·······Me |
| 107 | 98 | (4-MeO-1-Pip)- | ·······Me |
| 108 | 98 | {4-[MeO—(CH₂)₂—O]-1-Pip}- | ·······Me |
| 109 | 98 | 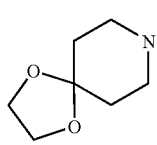 | ·······Me |
| 110 | 98 | {4-[MeO—(CH₂)₃]-4-MeO-1-Pip}- | ·······Me |
| 111 | 82 | 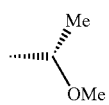 | ·······Me |
| 112 | 98 | (4-MeO-4-Me-1-Pip)- | ·······Me |
| 113 | 233 | (4-Me-1-Pipa)- | ·······Bn |
| 114 | 233 | 4-Mor- | ·······⟨Me, OMe⟩ |

TABLE 3-continued

| Ex | Syn | E | R |
|---|---|---|---|
| 115 | 82 | 4-Mor- | ⋯⋯CH₂OEt |
| 116 | 82 | MeO—(CH₂)₂—N(Me)- | ⋯⋯CH₂OEt |
| 117 | 98 | [(2R)-2-(MeO—CH₂)-4-Mor]- | ⋯⋯Me |
| 118 | 74 | 4-(4-methylpiperazin-1-yl)pyrimidin-2-yl | ⋯⋯Me |
| 119 | 98 | 8-methyl-2-oxa-8-azaspiro[4.5]decane | ⋯⋯Me |
| 120 | 98 | {4-[MeO—(CH₂)₂]-4-(MeO—CH₂)-1-Pip}- | ⋯⋯Me |
| 121 | 98 | [4-(1-Me-1H-5-Pyr)-1-Pip]- | ⋯⋯Me |
| 122 | 98 | [3-(MeO—CH₂)-4-Mor]- | ⋯⋯Me |
| 123 | 98 | [4,4-(MeO—CH₂)₂-1-Pip]- | ⋯⋯Me |
| 124 | 98 | (4-EtO-4-Me-1-Pip)- | ⋯⋯Me |
| 125 | 98 | [(2R)-2-(MeO—CH₂)-4-Mor]- | ⋯⋯CH₂OMe |
| 126 | 98 | N-methyl-2-oxa-5-azabicyclo[2.2.1]heptane | ⋯⋯Me |
| 127 | 98 | N-methyl-2-oxa-5-azabicyclo[2.2.1]heptane | ⋯⋯CH₂OMe |
| 128 | 98 | [4-(1-Me-1H-5-Pyr)-1-Pip]- | ⋯⋯CH₂OMe |
| 129 | 98 | 3-MeO-1-methylazetidine | ⋯⋯CH₂OMe |
| 130 | 82 | 4-methylthiomorpholine | ⋯⋯Me |

TABLE 3-continued
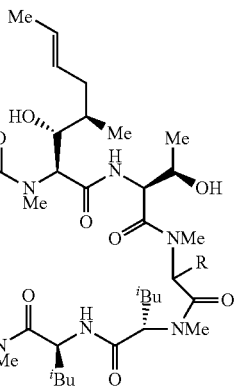
| Ex | Syn | E | R |
|---|---|---|---|
| 131 | 82 | [4,4-(F)$_2$-1-Pip]- | ••••••Me |
| 132 | 98 | (4-Et-4-MeO-1-Pip)- | ••••••Me |
| 133 | 98 | [(2S)-2-(MeO—CH$_2$)-4-Mor]- | ••••••CH$_2$OMe |
| 134 | 98 | 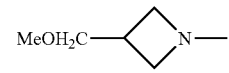 | ••••••CH$_2$OMe |
| 135 | 98 |  | ••••••CH$_2$OMe |
| 136 | 98 | [(3S,5S)-3,5-(Me)$_2$-4-Mor]- | ••••••CH$_2$OMe |
| 137 | 98 | [2,2-(Me)$_2$-4-Mor]- | ••••••Me |
| 138 | 98 | [2,2-(MeO—CH$_2$)$_2$-4-Mor]- | ••••••Me |
| 139 | 98 | (4-CF$_3$-1-Pip)- | ••••••Me |
| 140 | 82 | 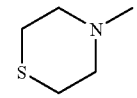 | ••••••CH$_2$OMe |
| 141 | 98 | 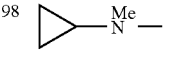 | ••••••Me |
| 142 | 98 | 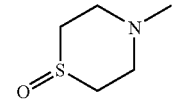 | ••••••Me |
| 143 | 98 |  | ••••••Me |
| 144 | 98 | 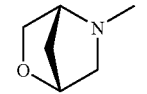 | ••••••CH$_2$OMe |
| 145 | 98 | CF$_3$—CH$_2$—N(Me)- | ••••••Me |
| 146 | 98 | 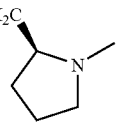 | ••••••Me |

TABLE 3-continued
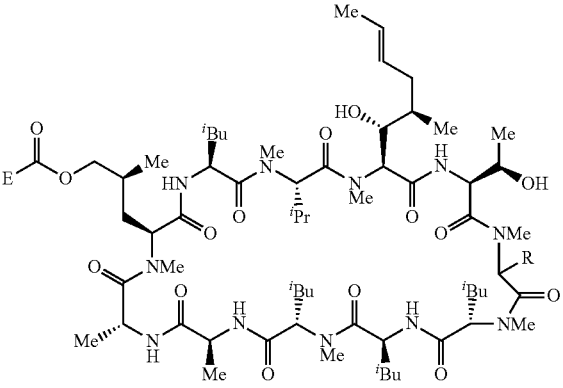
| Ex | Syn | E | R |
|---|---|---|---|
| 147 | 98 | {(2R)-2-[(1-Pip)-CH₂]-1-Pip}- | ·······ᶦᶦCH₂OMe |
| 148 | 98 | {(2S)-2-[(1-Pip)-CH₂-1-Pip}- | ·······ᶦᶦCH₂OMe |
| 149 | 98 | [(2R)-2-(MeO—CH₂)-1-Pip]- | ·······ᶦᶦCH₂OMe |
| 150 | 98 | [(2S)-2-(MeO—CH₂)-1-Pip]- | ·······ᶦᶦCH₂OMe |
| 151 | 98 | 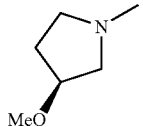 | ·······ᶦᶦCH₂OMe |
| 152 | 98 | 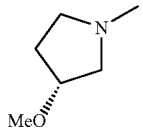 | ·······ᶦᶦCH₂OMe |
| 153 | 98 | 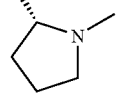 | ·······ᶦᶦMe |
| 154 | 98 | [3-(MeO—CH₂)-1-Pip]- | ·······ᶦᶦCH₂OMe |
| 155 | 82 | 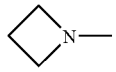 | ·······ᶦᶦCH₂OMe |
| 156 | 98 | 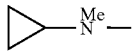 | ·······ᶦᶦCH₂OMe |
| 157 | 98 | 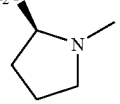 | ·······ᶦᶦCH₂OMe |
| 158 | 98 | 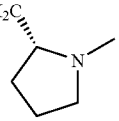 | ·······ᶦᶦCH₂OMe |

TABLE 3-continued

| Ex | Syn | E | R |
|----|-----|---|---|
| 159 | 98 | 1-Me-4-(4-pyridyl)-1,2,3,6-tetrahydropyridin-yl | ·······ıCH₂OMe |
| 160 | 98 | [4-(4-Py)-1-Pip]- | ·······ıCH₂OMe |
| 161 | 98 | [4-(3-Py)-1-Pip]- | ·······ıCH₂OMe |
| 162 | 98 | 4-methyl-1-(thiophen-3-yl)cyclohex-1-enyl | ·······ıCH₂OMe |
| 163 | 98 | [4-MeO-4-(1-Me-1H-2-Imi)-1-Pip]- | ·······ıCH₂OMe |
| 164 | 98 | 4-methyl-1,4-oxazepan-yl | ·······ıCH₂OMe |
| 165 | 98 | (Me)₂N— | ·······ıMe |
| 166 | 98 | [4-MeO-4-(1-Me-1H-2-Imi)-1-Pip]- | ·······ıMe |
| 167 | 98 | 3-MeO-1-Me-azetidin-yl | ·······ıMe |
| 168 | 98 | 3-(MeOCH₂)-1-Me-azetidin-yl | ·······ıMe |
| 169 | 98 | N-Me-thia-bicyclic | ·······ıMe |
| 170 | 98 | NH₂—C(O)—CH₂—N(Me)- | ·······ıMe |
| 171 | 98 | (3R)-3-MeO-1-Me-pyrrolidin-yl | ·······ıMe |

TABLE 3-continued

| Ex | Syn | E | R |
|---|---|---|---|
| 172 | 98 | (1-methyl-3-methoxypyrrolidinyl) | ·······Me |
| 173 | 98 | (4-methyl-1,4-oxazepanyl) | ·······Me |
| 174 | 98 | MeO—(CH$_2$)$_3$—N(Me)- | ·······Me |
| 175 | 98 | (MeO—CH$_2$)$_2$CH—N(Me)- | ·······Me |
| 176 | 82 | [4-(CH$_2$=CH—CH$_2$)-1-Pipa]- | ·······Me |
| 177 | 82 | (tetrahydrofuran-2-ylmethyl)-(4-methylpiperazinyl), epimer mix | ·······Me |
| 178 | 82 | MeO—(CH$_2$)$_2$N(Et)- | ·······Me |
| 179 | 82 | 2-(4-methylpiperazin-1-yl)pyrazine | ·······Me |
| 180 | 98 | [4-(1-Me-1H-2-Imi)-1-Pip]- | ·······Me |
| 181 | 82 | 2-(4-methylpiperazin-1-yl)-4,6-dimethylpyrimidine | ·······Me |
| 182 | 82 | 1-methylpyrrolidine | ·······Me |

TABLE 3-continued

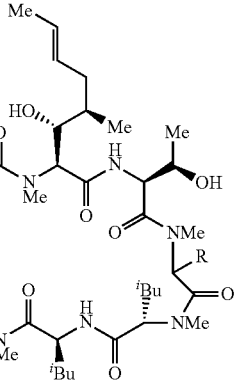

| Ex | Syn | E | R |
|---|---|---|---|
| 183 | 98 | 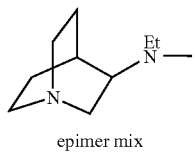<br>epimer mix | ·······Me |
| 184 | 98 | [(2S)-2-(MeO—CH$_2$)-1-Pip]- | ·······Me |
| 185 | 98 | {(2S)-2-[(1-Pip)-CH$_2$]-1-Pip}- | ·······Me |
| 186 | 98 | 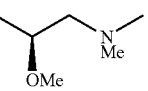 | ·······Me |
| 187 | 98 | 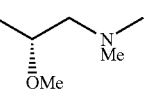 | ·······Me |
| 188 | 82 | {4-[1-Pip-(CH$_2$)$_2$]-1-Pipa}- | ·······Me |
| 189 | 82 | (Et)$_2$N—(CH$_2$)$_2$—N(Me)- | ·······Me |
| 190 | 82 | {4-[(Me)$_2$N—(CH$_2$)$_2$]-1-Pipa}- | ·······Me |
| 191 | 82 | (4-$^i$Pr-1-Pipa)- | ·······Me |
| 192 | 82 | [4-(1-Me-4-Pip)-1-Pipa]- | ·······Me |
| 193 | 82 | (Me)$_2$N—(CH$_2$)$_3$—N(Me)- | ·······Me |
| 194 | 82 | {4-[EtO—(CH$_2$)$_2$]-1-Pipa}- | ·······Me |
| 195 | 82 | {4-[(Me)$_2$N—(CH$_2$)$_3$]-1-Pipa}- | ·······Me |
| 196 | 98 | 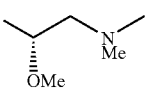 | ·······Me |
| 197 | 98 | 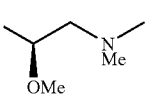 | ·······Me |
| 198 | 98 | 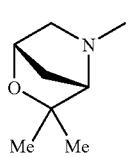 | ·······Me |

TABLE 3-continued

[Structure of cyclic peptide with E-O-CH2- and R substituents]

| Ex | Syn | E | R |
|----|-----|---|---|
| 199 | 98 | (1-methyl-3,4-dimethoxypyrrolidinyl, one stereochem) | ......Me |
| 200 | 98 | (1-methyl-3,4-dimethoxypyrrolidinyl, other stereochem) | ......Me |
| 201 | 98 | (N-methyl-2,2-dimethyl-oxa-azabicyclic) | ......CH₂OMe |
| 202 | 98 | (N-methyl-thia-azabicyclic) | ......CH₂OMe |

TABLE 4

[Structure of cyclic peptide with A-CH2- and R substituents]

| Ex | Syn | A | R |
|----|-----|---|---|
| 204 | — | OH | ......Me |
| 205-A | — | OMe | ......Me |

TABLE 4-continued

[Structure of cyclic peptide with A-CH2- and R substituents]

| Ex | Syn | A | R |
|----|-----|---|---|
| 206 | 43 | (Et)₂N— | ......Me |
| 207 | — | ⁱPrO—C(O)—N(Et)- | ......Me |

TABLE 4-continued

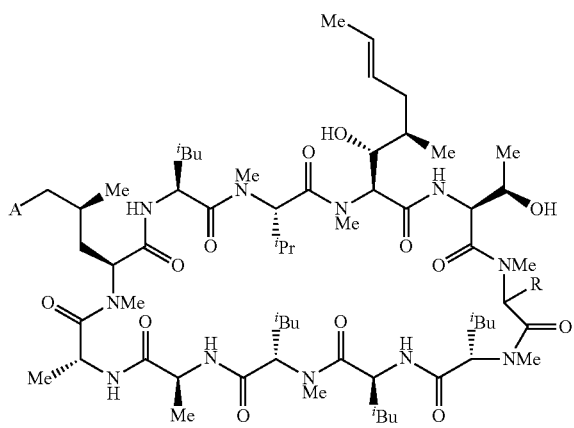

| Ex | Syn | A | R |
|---|---|---|---|
| 208 | 207 | iPr—C(O)—N(Et)- | ......"Me |
| 209 | 207 | 4-Mor-C(O)—N(Et)- | ......"Me |
| 210 | — | (Me)₂N—C(O)—N(Et)- | ......"Me |
| 211 | 207 | 4-Mor-C(O)—NH— | ......"Me |
| 212 | 43 | 4-Mor- | ......"Me |
| 213 | 43 | 1-Pip- | ......"Me |
| 214 | 43 | (4-Py-CH₂)—N(Me)- | ......"Me |
| 215 | 43 | (ⁿPr)₂N— | ......"Me |
| 216 | 43 | N-methylazepane | ......"Me |
| 217 | 43 | MeO—(CH₂)₂—N(Me)- | ......"Me |
| 218 | 43 | N-methyl-oxa-azabicyclic | ......"Me |
| 219 | 43 | [(2R)-2-(MeO—CH₂)-4-Mor]- | ......"Me |
| 220 | 43 | [(2S)-2-(MeO—CH₂)-4-Mor]- | ......"Me |
| 221 | 43 | [2,2-(MeO—CH₂)₂-4-Mor]- | ......"Me |
| 222 | 43 | [2,2-(Me)₂-4-Mor]- | |
| 223 | 43 | N-methylthiomorpholine | ......"Me |
| 224 | 43 | N-methyl-oxa-azabicyclic | ......"Me |
| 225 | 43 | [(3S)-3-(MeO—CH₂)-4-Mor]- | ......"Me |
| 226 | 43 | [(3R)-3-(MeO—CH₂)-4-Mor]- | ......"Me |

TABLE 4-continued

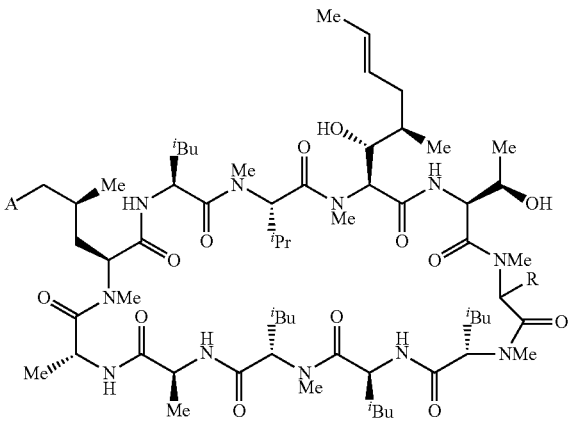

| Ex | Syn | A | R |
|---|---|---|---|
| 227 | 43 | [(2R)-2-(MeO—CH₂)-4-Mor]- | ......"CH₂OMe |
| 228 | 43 | [2,2-(MeO—CH₂)₂-4-Mor]- | ......"CH₂OMe |
| 230 | 228 | 4-Mor- | ......"CH₂OMe |
| 231 | 43 | [(3R)-3-(MeO—CH₂)-4-Mor]- | ......"CH₂OMe |

TABLE 5

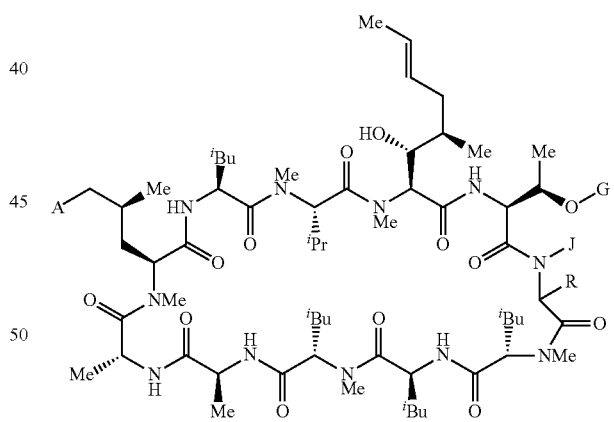

| Ex | Syn | A | G | J | R |
|---|---|---|---|---|---|
| 232 | 204 | (4-Me-1-Pipa)-C(O)—O— | H | Et | ......"Me |
| 233 | — | 4-Mor-C(O)—O— | H | Et | ......"Me |
| 205-B | — | MeO— | Me | Me | ......"Me |

TABLE 6
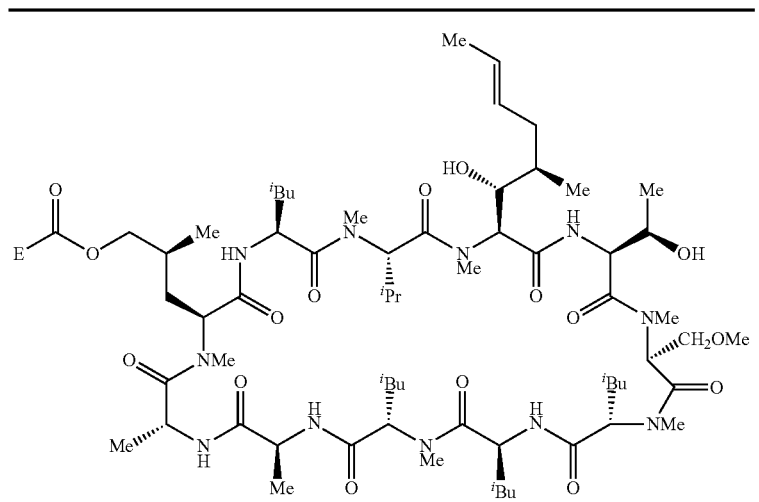
| Ex | Syn | E |
|---|---|---|
| 234 | 98 | |
| 235 | 98 | [(2R)-2-(MeO—CH$_2$)-4-Mor]- |
TABLE 7
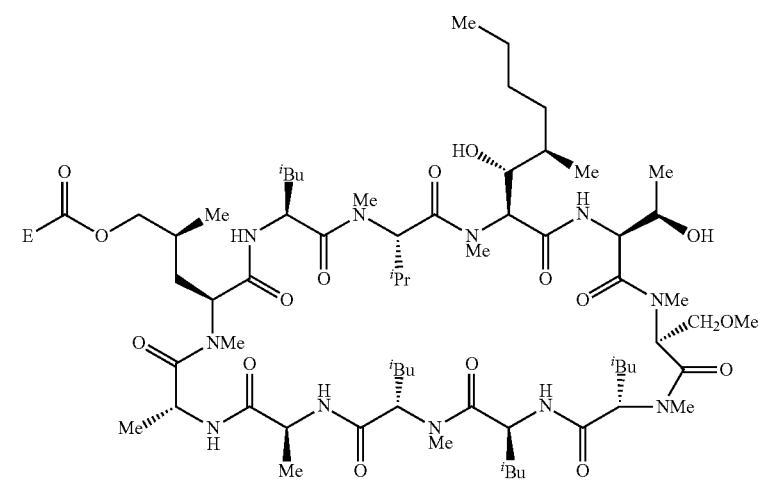
| Ex | Syn | E |
|---|---|---|
| 236 | 259 | |
| 237 | 259 | [(2R)-2-(MeO—CH$_2$)-4-Mor]- |

TABLE 8

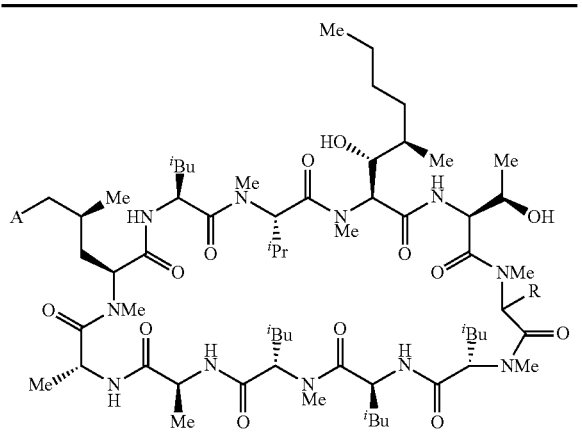

| Ex | Syn A | R |
|---|---|---|
| 61 | 54 (3-MeO-Ph)-C(O)—NH— | —H |
| 102 | — 4-Mor-C(O)—O— | ·······ııMe |
| 203 | 259 [(2R)-2-(MeO—CH$_2$)-4-Mor]-C(O)—O— | ·······ııCH$_2$OMe |
| 229 | 259 [2,2-(MeO—CH$_2$)$_2$-4-Mor]- | ·······ııCH$_2$OMe |
| 238 | — MeO—(CH$_2$)$_2$—N(Me)—C(O)—O— | —H |
| 239 | 238 (4-Me-1-Pipa)-C(O)—O— | —H |
| 240 | 238 {4-[4-Mor-C(O)—CH$_2$]-1-Pipa}-C(O)—O— | —H |
| 241 | 54 [4-(Me)$_2$N-Ph]-C(O)—NH— | —H |
| 242 | 238 [(4-Mor)-1-Pipa]-C(O)—O— | —H |
| 243 | 238 Et-N(Me)-C(O)—O— | —H |
| 244 | 238 | —H |
| 245 | 238 | —H |
| 246 | 238 | —H |
| 247 | 238 [(2R,6R)-2,4,6-(Me)$_3$-1-Pipa]-C(O)—O— | —H |
| 248 | 238 (4-Py)-N(Me)-C(O)—O— | —H |
| 249 | 238 (2-Py)-N(Me)-C(O)—O— | —H |
| 250 | 238 (1-Me-4-Pyr)-CH$_2$—N(Me)-C(O)—O— | —H |
| 251 | 238 Ph-N(Me)-C(O)—O— | —H |
| 252 | 259 (4-Me-1-Pipa)-C(O)—O— | ·······ııMe |
| 253 | 259 4-Mor-C(O)—O— | ·······ııCH$_2$OMe |
| 254 | 259 MeO—(CH$_2$)$_2$—N(Me)-C(O)—O— | ·······ııCH$_2$OMe |
| 255 | 259 4-Mor-C(O)—O— | ·······ıı$^n$Pr |

TABLE 8-continued

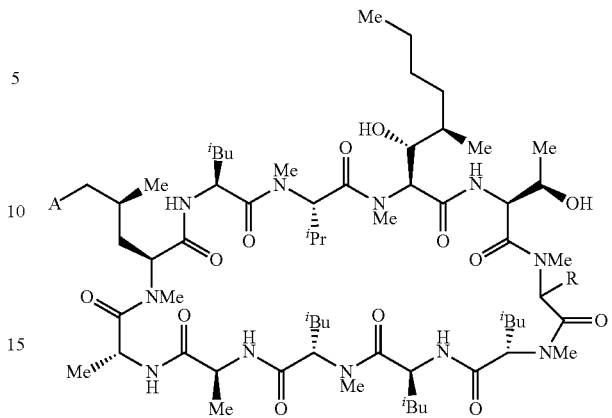

| Ex | Syn A | R |
|---|---|---|
| 256 | 259 (4-Me-1-Pipa)-C(O)—O— | ·······ıı$^n$Pr |
| 257 | 259 | ·······ııMe |
| 258 | 259 | ·······ııMe |
| 259 | — [(2R)-2-(MeO—CH$_2$)-4-Mor]- | ·······ııCH$_2$OMe |
| 260 | 259 [(2R)-2-(MeO—CH$_2$)-4-Mor]- | ·······ııMe |
| 261 | 259 [2,2-(MeO—CH$_2$)$_2$-4-Mor]- | ·······ııMe |
| 262 | 259 4-Mor- | ·······ııMe |
| 263* | 259 4-Mor- | ·······ııMe |
| 264 | 259 4-Mor- | ·······ııCH$_2$OMe |
| 265 | 259 [(3R)-3-(MeO—CH$_2$)-4-Mor]- | ·······ııCH$_2$OMe |

*Ex 263 is a HCl salt.

TABLE 9

| Ex | Data |
|---|---|
| 1 | NMR: 0.70-5.90 (113H, m), 6.82 (1H, d, J = 8.5 Hz), 6.91 (1H, d, J = 7.5 Hz), 7.02 (1H, d, J = 9.0 Hz), 7.63 (1H, d, J = 9.1 Hz), 9.04 (1H, d, J = 9.1 Hz). (for a major conformer) MS: 1346.74 |
| 2 | MS: 1347.79 |
| 3 | MS: 1389.60 |
| 4 | MS: 1403.60 |
| 5 | MS: 1367.63 |
| 6 | MS: 1422.69 |
| 7 | NMR: 0.70-5.90 (115H, m), 6.82 (1H, d, J = 8.7 Hz), 6.89 (1H, d, J = 7.3 Hz), 7.01 (1H, d, J = 8.8 Hz), 7.64 (1H, d, J = 9.1 Hz), 9.00 (1H, d, J = 9.6 Hz). (for a major conformer) MS: 1348.78 |

TABLE 9-continued

| Ex | Data |
|---|---|
| 8 | NMR: 0.70-5.90 (116H, m), 6.83 (1H, d, J = 8.2 Hz), 6.87 (1H, d, J = 7.5 Hz), 7.01 (1H, d, J = 9.2 Hz), 7.65 (1H, d, J = 9.1 Hz), 8.86 (1H, d, J = 9.2 Hz). (for a major conformer) MS: 1361.00 |
| 9 | MS: 1359.56 |
| 10 | MS: 1394.98 |
| 11 | MS: 1375.82 |
| 12 | NMR: 0.70-5.90 (113H, m), 6.82 (1H, d, J = 8.6 Hz), 6.88 (1H, d, J = 7.4 Hz), 7.64 (1H, d, J = 9.1 Hz), 8.99 (1H, d, J = 8.8 Hz). (for a major conformer) MS: 1319.51 |
| 13 | MS: 1475.73 |
| 14 | ESI (M + H$_2$O)$^+$: 1455.59 |
| 15 | MS: 1473.64 |
| 16 | ESI (M + H$_2$O)$^+$: 1392.00 |
| 17 | MS: 1396.61 |
| 18 | MS: 1383.58 |
| 19 | MS: 1400.42 |
| 20 | ESI (M + H$_2$O)$^+$: 1463.12 |
| 21 | NMR: 0.60-5.90 (113H, m), 6.83 (1H, d, J = 8.5 Hz), 6.87 (1H, d, J = 7.4 Hz), 7.01 (1H, d, J = 8.8 Hz), 7.64 (1H, d, J = 9.1 Hz), 8.90 (1H, d, J = 9.3 Hz). (for a major conformer) MS: 1346.11 |
| 22 | MS: 1431.78 |
| 23 | MS: 1386.95 |
| 24 | MS: 1375.95 |
| 25 | MS: 1375.95 |
| 26 | MS: 1396.90 |
| 27 | MS: 1402.88 |
| 28 | MS: 1376.82 |
| 29 | ESI (M + Na)$^+$: 1408.0 |
| 30 | MS: 1375.82 |
| 31 | ESI (M + Na)$^+$: 1437.8 |
| 32 | MS: 1388.61 |
| 33 | MS: 1374.66 |
| 34 | MS: 1388.67 |
| 35 | MS: 1388.53 |
| 36 | MS: 1492.9 |
| 37 | MS: 1368.37 |
| 38 | MS: 1368.91 |
| 39 | MS: 1368.45 |
| 40 | MS: 1385.51 |
| 41 | MS: 1367.42 |
| 42 | MS: 1374.50 |
| 43 | NMR: 0.50-2.60 (67H, m), 2.91 (3H, s), 2.97 (3H, s), 3.09 (3H, s), 3.15 (3H, s), 3.17 (3H, s), 3.22 (3H, s), 2.70-5.90 (28H, m), 6.82 (1H, d, J = 8.3 Hz), 6.93 (1H, d, J = 7.4 Hz), 6.99 (1H, d, J = 9.1 Hz), 7.66 (1H, d, J = 8.7 Hz), 9.07 (1H, d, J = 9.1 Hz). (for a major conformer) MS: 1303.95 |
| 44 | NMR: 0.70-2.45 (69H, m), 2.60-5.85 (18H, m), 2.73 (3H, s), 2.93 (3H, s), 2.96 (3H, s), 3.03 (3H, s), 3.16 (3H, s), 3.44 (3H, s), 6.79 (1H, d, J = 7.5 Hz), 6.83 (1H, d, J = 7.5 Hz), 6.94 (1H, d, J = 7.5 Hz), 7.18-7.32 (5H, m), 7.68 (1H, d, J = 9.1 Hz), 8.67 (1H, d, J = 9.6 Hz). (for a major conformer) MS: 1326.59, ESI (M + H$_2$O)$^+$: 1343.60 |
| 45 | NMR: 0.75-2.70 (69H, m), 2.75-5.80 (18H, m), 2.95 (3H, s), 3.10 (3H, s), 3.12 (3H, s), 3.15 (3H, s), 3.16 (3H, s), 3.17 (3H, s), 6.72-7.08 (6H, m), 7.69 (1H, d, J = 9.0 Hz), 8.74 (1H, d, J = 9.3 Hz). (for a major conformer) MS: 1346.57 |
| 46 | NMR: 0.70-2.60 (69H, m), 2.60-5.85 (20H, m), 2.91 (3H, s), 2.95 (3H, s), 3.05 (3H, s), 3.11 (3H, s), 3.15 (3H, s), 3.16 (3H, s), 6.83 (1H, d, J = 8.4 Hz), 6.88 (1H, d, J = 7.3 Hz), 7.05 (1H, d, J = 7.1 Hz), 7.31-7.34 (5H, m), 7.66 (1H, d, J = 9.1 Hz), 8.83 (1H, d, J = 9.1 Hz). (for a major conformer) MS: 1323.59 |
| 47 | NMR: 0.70-2.80 (69H, m), 2.80-5.85 (18H, m), 2.91 (3H, s), 2.97 (3H, s), 3.01 (3H, s), 3.12 (3H, s), 3.15 (3H, s), 3.17 (3H, s), 6.82 (1H, d, J = 8.4 Hz), 6.95 (1H, d, J = 7.4 Hz), 7.04 (1H, d, J = 9.0 Hz), 7.57 (2H, d, J = 7.9 Hz), 7.66 (1H, d, J = 7.5 Hz), 7.89 (2H, d, J = 8.0 Hz), 9.08 (1H, d, J = 9.2 Hz). (for a major conformer) MS: 1358.88 |
| 48 | NMR: 0.70-2.80 (69H, m), 2.80-5.85 (18H, m), 2.91 (3H, s), 2.97 (3H, s), 3.02 (3H, s), 3.09 (3H, s), 3.15 (3H, s), 3.16 (3H, s), 6.82 (1H, d, J = 8.4 Hz), 6.94 (1H, d, J = 7.4 Hz), 7.03 (1H, d, J = 9.0 Hz), 7.61 (1H, d, J = 9.0 Hz), 8.41 (1H, d), 9.07 (1H, d, J = 9.1 Hz). (for a major conformer) MS: 1334.88 |
| 49 | NMR: 0.70-2.80 (69H, m), 2.80-5.80 (18H, m), 2.94 (3H, s), 3.08 (3H, s), 3.12 (3H, s), 3.15 (3H, s), 3.16 (3H, s), 3.44 (3H, s), 6.80-8.00 (6H, m), 8.66 (1H, d, J = 9.1 Hz). (for a major conformer) MS: 1354.95 |
| 50 | NMR: 0.70-2.45 (69H, m), 2.60-5.80 (20H, m), 2.73 (3H, s), 2.94 (3H, s), 3.03 (3H, s), 3.16 (3H, s), 3.44 (3H, s), 3.67 (3H, s), 6.60-8.60 (10H, m). (for a major conformer) MS: 1340.79 |
| 51 | NMR: 0.70-2.45 (69H, m), 2.80-5.90 (26H, m), 2.91 (3H, s), 2.96 (3H, s), 3.07 (3H, s), 3.10 (3H, s), 3.15 (3H, s), 3.17 (3H, s), 6.82 (1H, d, J = 8.6 Hz), 6.93 (1H, d, J = 7.6 Hz), 7.01 (1H, d, J = 9.0 Hz), 7.66 (1H, d, J = 9.1 Hz), 9.01 (1H, d, J = 9.2 Hz). (for a major conformer) MS: 1364.25 |
| 52 | MS: 1376.23 |
| 53 | MS: 1365.20 |
| 54 | NMR: 0.70-2.45 (69H, m), 2.60-5.80 (18H, m), 2.92 (3H, s), 2.96 (3H, s), 3.05 (3H, s), 3.11 (3H, s), 3.15 (3H, s), 3.16 (3H, s), 3.85 (3H, s), 6.55-8.30 (3H, m), 6.92 (2H, d, J = 8.8 Hz), 7.65 (1H, d, J = 9.0 Hz), 7.75 (2H, d, J = 8.7 Hz), 8.02 (1H, d, J = 9.0 Hz), 8.94 (1H, d, J = 9.2 Hz). (for a major conformer) MS: 1367.09 |
| 55 | MS: 1367.02 |
| 56 | MS: 1380.12 |
| 57 | MS: 1439.16 |
| 58 | MS: 1370.14 |
| 59 | MS: 1397.13 |
| 60 | MS: 1489.00 |
| 61 | NMR: 0.70-2.45 (73H, m), 2.70-5.80 (16H, m), 2.92 (3H, s), 2.97 (3H, s), 3.06 (3H, s), 3.08 (3H, s), 3.16 (3H, s), 3.17 (3H, s), 3.85 (3H, s), 6.70-8.20 (9H, m), 9.20 (1H, d, J = 9.3 Hz). (for a major conformer) MS: 1369.23 |
| 62 | MS: 1422.39 |
| 63 | MS: 1338.85 |
| 64 | $^1$H NMR (pyridine-d$_5$, δ): 0.50-2.90 (67H, m), 2.99 (3H, s), 3.26 (3H, s), 3.27 (3H, s), 3.32 (3H, s), 3.43 (3H, s), 3.65 (3H, s), 4.24 (3H, s), 3.00-7.00 (19H, m), 7.62 (1H, d, J = 6.9 Hz), 7.86 (1H, d, J = 6.7 Hz), 7.91 (1H, d, J = 9.3 Hz), 8.44 (1H, d, J = 9.0 Hz), 8.53 (1H, d, J = 9.4 Hz), 9.66 (1H, d, J = 6.0 Hz). (for a major conformer) MS: 1248.45 |
| 65 | NMR: 0.50-2.60 (67H, m), 2.91 (3H, s), 2.96 (3H, s), 3.05 (3H, s), 3.10 (3H, s), 3.15 (3H, s), 3.16 (3H, s), 2.70-6.00 (32H, m), 6.82 (1H, d, J = 8.5 Hz), 6.88 (1H, d, J = 7.4 Hz), 7.00 (1H, d, J = 8.9 Hz), 7.65 (1H, d, J = 9.0 Hz), 8.95 (1H, d, J = 9.2 Hz). (for a major conformer) MS: 1391.20 |
| 66 | NMR: 0.50-2.80 (67H, m), 2.91 (3H, s), 2.96 (3H, s), 3.06 (3H, s), 3.09 (3H, s), 3.15 (3H, s), 3.17 (3H, s), 2.90-5.90 (32H, m), 6.83 (1H, d, J = 8.5 Hz), 6.88 (1H, d, J = 7.5 Hz), 7.00 (1H, d, J = 8.8 Hz), 7.65 (1H, d, J = 9.1 Hz), 8.98 (1H, d, J = 9.2 Hz). (for a major conformer) MS: 1347.16 |
| 67 | NMR: 0.70-2.50 (67H, m), 2.70-5.88 (30H, m), 2.92 (3H, s), 2.96 (3H, s), 3.07 (3H, s), 3.11 (3H, s), 3.15 (3H, s), 3.16 (3H, s), 3.35 (3H, s), 3.36 (3H, s), 6.83 (1H, d, J = 8.6 Hz), 6.90 (1H, d, J = 7.4 Hz), 6.99 (1H, d, J = 9.0 Hz), 7.66 (2H, d, J = 9.0 Hz), |

TABLE 9-continued

| Ex | Data |
|---|---|
|  | 8.88 (1H, d, J = 9.2 Hz). (for a major conformer) |
|  | MS: 1391.80 |
| 68 | MS: 1344.46 |
| 69 | MS: 1301.68 |
| 70 | MS: 1337.69 |
| 71 | MS: 1305.72 |
| 72 | MS: 1349.78 |
| 73 | MS: 1374.84 |
| 74 | MS: 1363.79 |
| 75 | MS: 1382.76 |
| 76 | NMR: 0.71 (3H, d, J = 6.7 Hz), 0.72-1.07 (10H, m), 0.80 (3H, d, J = 6.4 Hz), 0.82 (3H, d, J = 6.5 Hz), 0.86 (3H, d, J = 6.5 Hz), 0.89 (3H, d, J = 6.8 Hz), 0.92 (3H, d, J = 6.6 Hz), 0.95 (3, d, J = 6.5 Hz), 1.03 (3H, d, J = 6.8 Hz), 1.10 (3H, d, J = 6.5 Hz), 1.12 (3H, d, J = 7.0 Hz), 1.33 (3H, d, J = 7.0 Hz), 1.38 (3H, d, J = 7.5 Hz), 1.45-2.48 (23H, m), 1.65 (3H, d, J = 5.7 Hz), 2.91 (3H, s), 2.97 (3H, s), 3.04 (3H, s), 3.06 (3H, s), 3.09 (3H, s), 3.16 (3H, s), 3.39-3.50 (4H, m), 3.56-3.80 (4H, m), 3.84-4.00 (2H, m), 4.08-4.32 (2H, m), 4.52 (1H, dd, J = 8.9 and 7.1 Hz), 4.70 (1H, t, J = 7.1 Hz), 4.76-5.62 (7H, m), 5.06 (1H, dd, J = 10.0 and 5.1 Hz), 5.15 (2H, dd, J = 11.2 and 4.3 Hz), 5.67 (1H, d, J = 3.2 Hz), 6.77 (1H, d, J = 8.3 Hz), 6.84 (1H, d, J = 7.6 Hz), 6.96-7.04 (1H, m), 7.66 (1H, d, J = 9.0 Hz), 8.76 (1H, d, J = 9.4 Hz). (for a major conformer) |
|  | MS: 1346.74 |
| 77 | MS: 1385.81 |
| 78 | MS: 1432.85 |
| 79 | ESI (M + H$_2$O)$^+$: 1436.83 |
| 80 | MS: 1390.84 |
| 81 | MS: 1377.81 |
| 82 | NMR: 0.71 (3H, d, J = 6.8 Hz), 0.80 (6H, s, J = 6.5 Hz), 0.87 (3H, d, J = 6.4 Hz), 0.88-1.05 (26H, m), 1.11 (6H, t, J = 7.5 Hz), 1.20-2.60 (27H, m), 2.90 (3H, s), 3.02 (3H, s), 3.04 (3H, s), 3.06 (3H, s), 3.07 (3H, s), 3.17 (3H, s), 3.37 (3H, s), 3.45 (4H, t-like), 3.64 (4H, t-like), 3.85-4.00 (2H, m), 4.05-4.40 (2H, m), 4.52 (1H, t-like, J = 7.0 Hz), 4.69 (1H, t-like, J = 7.0 Hz), 4.70-4.90 (2H, m), 4.90-5.05 (4H, m), 5.15 (1H, dd, J = 10.0, 5.3 Hz), 5.20-5.60 (3H, m), 5.65 (1H, d, J = 3.1 Hz), 6.76 (1H, d, J = 8.5 Hz), 6.89 (1H, d, J = 7.3 Hz), 7.00 (1H, d, J = 8.8 Hz), 7.65 (1H, d, J = 8.8 Hz), 9.04 (1H, d, J = 9.3 Hz). (for a major conformer) |
|  | ESI (M + H$_2$O)$^+$: 1408.35 |
| 83 | NMR: 0.71 (3H, d, J = 6.8 Hz), 0.81 (6H, d, J = 6.5 Hz), 0.87 (3H, d, J = 6.5 Hz), 0.88 (3H, d, J = 6.4 Hz), 0.89-1.05 (26H, m), 1.11 (6H, t, J = 7.7 Hz), 1.20-2.50 (31H, m), 2.90 (3H, s), 3.02 (3H, s), 3.05 (3H, s), 3.06 (3H, s), 3.17 (3H, s), 3.37 (3H, s), 3.40-3.54 (4H, m), 3.54-3.70 (2H, m), 3.75 (1H, t, J = 9.0 Hz), 3.92 (2H, d, J = 6.0 Hz), 4.10-4.30 (2H, m), 4.52 (1H, t-like, J = 8.5 Hz), 4.69 (1H, t-like, J = 7.5 Hz), 4.76-4.85 (1H, m), 4.86 (1H, d, J = 7.2 Hz), 4.90-5.10 (4H, m), 5.16 (1H, dd, J = 10.0, 5.3 Hz), 5.20-5.60 (3H, m), 5.65 (1H, d, J = 3.1 Hz), 6.76 (1H, d, J = 8.2 Hz), 6.89 (1H, d, J = 7.7 Hz), 7.00 (1H, d, J = 8.8 Hz), 7.65 (1H, d, J = 8.8 Hz), 9.07 (1H, d, J = 9.8 Hz). (for a major conformer) |
|  | MS: 1404.35 |
| 84 | NMR: 0.71 (3H, d, J = 6.8 Hz), 0.81 (6H, d, J = 6.5 Hz), 0.87 (3H, d, J = 6.5 Hz), 0.88 (3H, d, J = 6.4 Hz), 0.89-1.05 (26H, m), 1.11 (6H, t, J = 7.7 Hz), 1.20-2.70 (26H, m), 2.90 (3H, s), 2.95 (3H, s), 3.02 (3H, s), 3.06 (6H, s), 3.17 (3H, s), 3.20-3.60 (10H, m), 3.76 (1H, t, J = 9.2 Hz), 3.91 (2H, d, J = 6.0 Hz), 4.10-4.30 (2H, m), 4.52 (1H, t-like, J = 7.0 Hz), 4.69 (1H, t-like, J = 7.0 Hz), 4.70-4.90 (2H, m), 4.90-5.05 (4H, m), 5.16 (1H, dd, J = 10.0, 5.3 Hz), 5.20-5.60 (3H, m), 5.65 (1H, d, J = 3.1 Hz), 6.76 (1H, d, J = 8.1 Hz), 6.92 (1H, d, J = 7.4 Hz), 7.00 (1H, d, J = 8.9 Hz), 7.65 (1H, d, J = 8.9 Hz), 9.19 (1H, d, J = 9.2 Hz). (for a major conformer) |
|  | MS: 1393.35 |
| 85 | MS: 1349.34 |
| 86 | NMR: 0.71 (3H, d, J = 6.8 Hz), 0.75-1.15 (13H, m), 0.81 (3H, d, J = 6.5 Hz), 0.82 (3H, d, J = 6.6 Hz), 0.87 (3H, d, J = 6.6 Hz), 0.89 (3H, d, J = 6.8 Hz), 0.95 (6H, d, J = 8.0 Hz), 0.99 (3H, d, J = 6.0 Hz), 1.03 (3H, d, J = 7.6 Hz), 1.10 (3H, d, J = 6.5 Hz), 1.12 (3H, d, J = 7.0 Hz), 1.17 (6H, d, J = 6.3 Hz), 1.27-1.64 (10H, m), 1.66 (3H, d, J = 6.0 Hz), 1.69-2.57 (13H, m), 2.91 (3H, s), 2.97 (3H, s), 3.05 (3H, s), 3.06 (3H, s), 3.08 (3H, s), 3.16 (3H, s), 3.44-4.05 (8H, m), 4.17-4.31 (2H, m), 4.52 (1H, dd, J = 8.9 and 7.0 Hz), 4.70 (1H, t, J = 7.1 Hz), 4.74-5.03 (4H, m), 5.06 (1H, dd, J = 10.2 and 5.2 Hz), 5.15 (1H, dd, J = 11.2 and 4.0 Hz), 5.31-5.61 (2H, m), 5.37 (2H, d, J = 10.2 Hz), 5.67 (1H, d, J = 3.3 Hz), 6.76 (1H, J = 8.3 Hz), 6.86 (1H, d, J = 7.6 Hz), 6.99 (1H, d, J = 8.9 Hz), 7.66 (1H, d, J = 9.0 Hz), 8.87 (1H, d, J = 9.2 Hz). (for a major conformer) |
|  | MS: 1389.42 |
| 87 | MS: 1407.43 |
| 88 | MS: 1418.44 |
| 89 | MS: 1418.46 |
| 90 | MS: 1375.37 |
| 91 | MS: 1388.37 |
| 92 | MS: 1377.39 |
| 93 | MS: 1333.36 |
| 94 | MS: 1387.41 |
| 95 | MS: 1400.33 |
| 96 | MS: 1402.47 |
| 97 | NMR: 0.71 (3H, d, J = 6.8 Hz), 0.72-1.37 (10H, m), 0.81 (3H, d, J = 6.5 Hz), 0.82 (3H, d, J = 6.5 Hz), 0.87 (3H, d, J = 6.6 Hz), 0.89 (3H, d, J = 6.9 Hz), 0.92 (3H, d, J = 6.7 Hz), 0.95 (6H, d, J = 6.5 Hz), 0.99 (3H, d, J = 6.6 Hz), 1.03 (3H, d, J = 8.3 Hz), 1.10 (3H, d, J = 6.5 Hz), 1.12 (3H, d, J = 6.9 Hz), 1.33 (6H, d, J = 6.5 Hz), 1.38 (3H, d, J = 7.3 Hz), 1.52-2.51 (22H, m), 1.66 (3H, d, J = 5.6 Hz), 2.24 (3H, s), 2.90 (3H, s), 2.98 (3H, s), 3.04 (3H, s), 3.06 (3H, s), 3.07 (3H, s), 3.17 (3H, s), 3.67-4.01 (6H, m), 4.05-4.32 (2H, m), 4.52 (1H, dd, J = 8.8 and 7.0 Hz), 4.70 (1H, t, J = 7.1 Hz), 4.74-5.02 (4H, m), 5.06 (1H, dd, J = 10.2 and 5.3 Hz), 5.15 (1H, dd, J = 11.3 and 4.1 Hz), 5.22-5.58 (2H, m), 5.36 (2, d, J = 10.2 Hz), 5.67 (1H, d, J = 3.3 Hz), 6.76 (1H, d, J = 7.5 Hz), 6.90 (1H, d, J = 7.5 Hz), 6.99 (1H, d, J = 8.7 Hz), 7.63 (1H, d, J = 9.1 Hz), 9.11 (1H, d, J = 8.9 Hz). (for a major conformer) |
|  | MS: 1402.43 |
| 98 | NMR: 0.71 (3H, d, J = 6.8 Hz), 0.73-1.07 (10H, m), 0.81 (3H, d, J = 6.4 Hz), 0.82 (3H, d, J = 6.5 Hz), 0.87 (3H, d, J = 6.7 Hz), 0.89 (3H, d, J = 6.8 Hz), 0.92 (3H, d, J = 6.6 Hz), 0.94 (3H, d, J = 6.5 Hz), 0.96 (3H, d, J = 6.5 Hz), 0.99 (3H, d, J = 6.6 Hz), 1.03 (3H, d, J = 6.5 Hz), 1.10 (3H, d, J = 6.5 Hz), 1.12 (3H, d, J = 6.9 Hz), 1.31 (6H, d, J = 6.8 Hz), 1.34 (3H, d, J = 7.4 Hz), 1.38 (3H, d, J = 7.4 Hz), 1.52-1.64 (4H, m), 1.66 (3H, d, J = 5.6 Hz), 1.70-2.48 (13H, m), 2.90 (3H, s), 2.98 (3H, s), 3.04 (3H, s), 3.06 (3H, s), 3.07 (3H, s), 3.17 (3H, s), 3.50-3.60 (2H, m), 3.67-4.04 (6H, m), 4.16-4.33 (2H, m), 4.52 (1H, dd, J = 8.0 and 6.9 Hz), 4.70 (1H, t, J = 7.1 Hz), 4.77-5.02 (4H, m), 5.06 (1H, dd, J = 10.0 and 5.2 Hz), 5.15 (1H, dd, J = 11.3 and 4.0 Hz), 5.31-5.59 (2H, m), 5.36 (2H, d, J = 10.2), 5.67 (1H, d, J = 3.2 Hz), 6.76 (1H, d, J = 8.3 Hz), 6.91 (1H, d, J = 7.4 Hz), 7.00 (1H, d, J = 8.8 Hz), 7.64 (1H, d, J = 8.9 Hz), 9.14 (1H, d, J = 9.2 Hz). (for a major conformer) |
|  | MS: 1389.45 |
| 99 | NMR: 0.71 (3H, d, J = 6.8 Hz), 0.73-1.07 (10H, m), 0.81 (3H, d, J = 6.5 Hz), 0.82 (3H, d, J = 6.4 Hz), 0.87 (3H, d, J = 6.7 Hz), 0.89 (3H, d, J = 6.8 Hz), 0.92 (3H, d, J = 6.6 Hz), 0.94 (3H, d, J = 6.6 Hz), 0.96 (3H, d, J = 6.6 Hz), 0.99 (3H, d, J = 6.6 Hz), 1.03 (3H, d, J = 8.0 Hz), 1.10 (3H, d, J = 6.4 Hz), 1.12 (3H, d, J = 6.9 Hz), 1.31 (6H, d, J = 6.6 Hz), 1.33 (3H, d, J = 7.0 Hz), 1.38 (3H, d, J = 7.4 Hz), 1.50-1.64 (4H, m), 1.66 (3H, d, J = 5.6 Hz), 1.69-2.49 (13H, m), 2.90 (3H, s), 2.98 (3H, s), 3.04 (3H, s), |

TABLE 9-continued

| Ex | Data |
|---|---|
| | 3.06 (3H, s), 3.07 (3H, s), 3.17 (3H, s), 3.40-3.52 (2H, m), 3.62-3.98 (6H, m), 4.10-4.32 (2H, m), 4.52 (1H, dd, J = 8.8 and 7.0 Hz), 4.70 (1H, t, J = 7.1 Hz), 4.73-5.02 (4H, m), 5.06 (1H, dd, J = 10.0 and 5.3 Hz), 5.15 (1H, dd, J = 11.3 and 4.0 Hz), 5.30-5.59 (2H, m), 5.36 (2H, d, J = 10.1 Hz), 5.67 (1H, d, J = 3.2 Hz), 6.76 (1H, d, J = 8.2 Hz), 6.91 (1H, d, J = 7.4 Hz), 7.00 (1H, d, J = 9.0 Hz), 7.64 (1H, d, J = 9.0 Hz), 9.12 (1H, d, J = 8.5 Hz). (for a major conformer) MS: 1389.43 |
| 100 | NMR: 0.71 (3H, d, J = 6.8 Hz), 0.73-1.07 (12H, m), 0.81 (3H, d, J = 6.4 Hz), 0.82 (3H, d, J = 6.5 Hz), 0.87 (3H, d, J = 6.7 Hz), 0.89 (3H, d, J = 6.8 Hz), 0.92 (3H, d, J = 6.7 Hz), 0.94 (3H, d, J = 6.6 Hz), 1.10 (3H, d, J = 6.5 Hz), 1.12 (3H, d, J = 6.9 Hz), 1.30 (6H, d, J = 6.6 Hz), 1.33 (3H, d, J = 6.8 Hz), 1.37 (3H, d, 7.4 Hz), 1.50-1.64 (4H, m), 1.66 (3H, d, J = 5.6 Hz), 1.69-2.47 (20H, m), 2.90 (3H, s), 2.98 (3H, s), 3.04 (3H, s), 3.06 (6H, s), 3.17 (3H, s), 3.41-3.52 (2H, m), 3.78-3.89 (4H, m), 3.94 (2H, d, J = 6.0 Hz), 4.17-4.31 (2H, m), 4.52 (1H, dd, J = 8.9 and 6.9 Hz), 4.69 (1H, t, J = 7.2 Hz), 4.76-5.02 (5H, m), 5.06 (1H, dd, J = 10.0 and 5.2 Hz), 5.15 (1H, dd, J = 11.2 and 4.0 Hz), 5.35 (2H, d, J = 10.5 Hz), 5.38-5.54 (1H, m), 5.67 (1H, d, J = 3.2 Hz), 6.76 (1H, d, J = 8.7 Hz), 6.90 (1H, d, J = 7.0 Hz), 7.00 (1H, d, J = 8.9 Hz), 7.69 (1H, d, J = 9.0 Hz), 9.15 (1H, d, J = 9.2 Hz). (for a major conformer) MS: 1389.47 |
| 101 | MS: 1402.50 |
| 102 | NMR: 0.71 (3H, d, J = 6.8 Hz), 0.79-1.07 (14H, m), 0.80 (3H, d, 6.4 Hz), 0.82 (3H, d, J = 6.5 Hz), 0.87 (3H, d, J = 6.6 Hz), 0.90 (3H, d, J = 6.6 Hz), 0.92 (3H, d, J = 6.9 Hz), 0.94 (3H, d, J = 6.6 Hz), 1.03 (3H, d, J = 6.5 Hz), 1.09 (3H, d, J = 6.5 Hz), 1.11 (3H, d, J = 6.9 Hz), 1.33 (3H, d, J = 6.9 Hz), 1.38 (3H, d, J = 7.4 Hz), 1.48-2.49 (26H, m), 2.91 (3H, s), 2.98 (3H, s), 3.04 (3H, s), 3.05 (3H, s), 3.06 (3H, s), 3.17 (3H, s), 3.42-3.48 (4H, m), 3.59-3.74 (4H, m), 3.90-3.99 (2H, m), 4.18-4.29 (2H, m), 4.52 (1H, dd, J = 8.8 and 7.1 Hz), 4.69 (1H, t, J = 7.1 Hz), 4.77-5.02 (6H, m), 5.05 (1H, dd, J = 10.3 and 5.2 Hz), 5.16 (1H, dd, J = 11.3 and 4.2 Hz), 5.35 (2H, d J = 10.3), 5.69 (1H, d, J = 3.2 Hz), 6.77 (1H, d, J = 8.2 Hz), 6.91 (1H, d, J = 7.6 Hz), 7.00 (1H, d, J = 9.0 Hz), 7.62 (1H, d, J = 9.1 Hz), 9.23 (1H, d, 9.0 Hz). (for a major conformer) MS: 1363.34 |
| 103 | MS: 1400.78 |
| 104 | MS: 1409.72 |
| 105 | MS: 1445.63 |
| 106 | MS: 1375.75 |
| 107 | MS: 1389.49 |
| 108 | MS: 1433.93 |
| 109 | MS: 1415.79 |
| 110 | MS: 1461.61 |
| 111 | MS: 1417.99 |
| 112 | MS: 1403.81 |
| 113 | MS: 1449.7 |
| 114 | MS: 1404.7 |
| 115 | MS: 1421.68 |
| 116 | MS: 1423.71 |
| 117 | ESI (M + H$_2$O)$^+$: 1421.70 |
| 118 | MS: 1437.67 |
| 119 | ESI (M + H$_2$O)$^+$: 1431.66 |
| 120 | MS: 1460.66 |
| 121 | MS: 1438.45 |
| 122 | MS: 1404.46 |
| 123 | MS: 1447.61 |
| 124 | NMR: 0.71 (3H, d, J = 6.8 Hz) 0.81 (3H, d, J = 6.5 Hz), 0.82 (3H, d, J = 6.4 Hz), 0.85-1.04 (26H, m), 1.10 (3H, d, J = 6.5 Hz), 1.12 (3H, d, J = 6.9 Hz), 1.16 (3H, s), 1.17 (3H, t, J = 7.0 Hz), 1.33 (3H, d, J = 7.0 Hz), 1.38 (3H, d, J = 7.4 Hz), 1.26-2.14 (24H, m), 2.33-2.49 (4H, m), 2.90 (3H, s), 2.91 (3H, s), 2.98 (3H, s), 3.05 (6H, s), 3.07 (3H, s), 3.16 (3H, s), 3.37 (2H, q, J = 13.9, 6.9 Hz), 3.72-3.91 (6H, m), 4.20-4.29 (2H, m), 4.53 (1H, dd, J = 8.8, 6.9 Hz), 4.69 (1H, t-like, J = 7.1 Hz), 4.78-5.01 (3H, m), 5.06 (1H, dd, J = 10.2, 5.2 Hz), 5.15 (1H, dd, J = 11.4, 4.1 Hz), 5.33-5.54 (3H, m), 5.67 (1H, d, J = 3.1 Hz), 6.76 (1H, d, J = 8.2 Hz), 6.89 (1H, d, J = 7.5 Hz), 7.00 (1H, d, J = 9.0 Hz), 7.65 (1H, d, J = 9.0 Hz), 9.06 (1H, d, J = 8.8 Hz). (for a major conformer) MS: 1418.08 |
| 125 | NMR: 0.71 (3H, d, J = 6.8 Hz), 0.75 (1H, t, J = 6.4 Hz), 0.80 (3H, d, J = 6.5 Hz), 0.81 (3H, d, J = 6.6 Hz), 0.86 (3H, d, J = 6.7 Hz), 0.88 (3H, d, J = 7.0 Hz), 0.92 (3H, d, J = 6.7 Hz), 0.94 (3H, d, J = 6.6 Hz), 0.93-0.97 (3H, m), 0.97-1.03 (14H, m), 1.10 (3H, d, J = 6.8 Hz), 1.12 (3H, d, J = 7.7 Hz), 1.26 (1H, t, J = 7.1 Hz), 1.30-1.38 (3H, m), 1.34 (3H, d, J = 6.8 Hz), 1.50-1.63 (3H, m), 1.66 (3H, d, J = 5.6 Hz), 1.69-2.18 (10H, m), 2.22-2.44 (3H, m), 2.60-2.86 (4H, m), 2.90 (3H, s), 3.02 (3H, s), 3.06 (3H, s), 3.07 (3H, s), 3.17 (3H, s), 3.38 (6H, d, J = 3.2 Hz), 3.40-3.46 (1H, m), 3.50-3.63 (3H, m), 3.76 (1H, t, J = 9.5 Hz), 3.85-3.98 (6H, m), 4.12 (1H, q, J = 7.2 Hz), 4.21 (1H, dd, J = 2.2, 6.5 Hz), 4.28 (1H, dd, J = 3.1, 10.4 Hz), 4.52 (1H, dd, J = 7.0, 8.8 Hz), 4.69 (1H, t, J = 7.1 Hz), 4.74-4.83 (1H, m), 4.83-4.89 (1H, m), 4.91-5.03 (4H, m), 5.08 (1H, dd, J = 5.2, 10.1 Hz), 5.15 (1H, dd, J = 4.0, 11.4 Hz), 5.30-5.56 (4H, m), 5.65 (1H, d, J = 3.2 Hz), 6.76 (1H, d, J = 8.2 Hz), 6.90 (1H, d, J = 7.5 Hz), 7.01 (1H, d, J = 8.8 Hz), 7.66 (1H, d, J = 9.0 Hz), 9.07 (1H, d, J = 9.4 Hz). (for a major conformer) MS: 1435.92 |
| 126 | MS: 1373.96 |
| 127 | MS: 1403.83 |
| 128 | NMR: 0.71 (3H, d, J = 6.7 Hz), 0.81 (6H, d, J = 6.5 Hz), 0.87 (3H, d, J = 6.8 Hz), 0.88 (3H, d, J = 7.3 Hz), 0.90-0.97 (9H, m), 0.97-1.04 (11H, m), 1.10 (3H, d, J = 7.3 Hz), 1.12 (3H, d, J = 7.5 Hz), 1.34 (6H, d, J = 6.9 Hz), 1.50-1.63 (5H, m), 1.66 (3H, d, J = 5.5 Hz), 1.70-2.10 (20H, m), 2.21-2.42 (2H, m), 2.45 (1H, d, J = 4.7 Hz), 2.69-2.79 (1H, m), 2.90 (3H, s), 3.05 (3H, s), 3.06 (3H, s), 3.07 (3H, s), 3.17 (3H, s), 3.37 (3H, s), 3.55 (1H, dd, J = 6.8, 10.5 Hz), 3.61-3.66 (1H, m), 3.76 (1H, t, J = 9.1 Hz), 3.84 (3H, s), 3.90-4.00 (2H, m), 4.15-4.34 (3H, m), 4.52 (1H, t, J = 7.6 Hz), 4.70 (1H, t, J = 6.9 Hz), 4.73-4.89 (2H, m), 4.90-5.03 (3H, m), 5.08 (1H, dd, J = 4.8, 9.6 Hz), 5.15 (1H, dd, J = 4.1, 11.0 Hz), 5.30 (1H, s), 5.30-5.40 (1H, m), 5.40-5.60 (1H, m), 5.65 (1H, d, J = 2.8 Hz), 6.00 (1H, d, J = 1.8 Hz), 6.76 (1H, d, J = 7.6 Hz), 6.92 (1H, d, J = 7.2 Hz), 7.01 (1H, d, J = 9.2 Hz), 7.39 (1H, d, J = 1.4 Hz), 7.65 (1H, d, J = 9.1 Hz), 9.17 (1H, d, J = 9.4 Hz). (for a major conformer) MS: 1471.03 |
| 129 | NMR: 0.71 (3H, d, J = 6.9 Hz), 0.80 (3H, d, J = 6.6 Hz), 0.81 (3H, d, J = 6.6 Hz), 0.86 (3H, d, J = 6.6 Hz), 0.88 (3H, d, J = 8.0 Hz), 0.92 (6H, d, J = 6.9 Hz), 0.93 (3H, d, J = 5.4 Hz), 0.94 (3H, d, J = 6.9 Hz), 0.97-1.04 (12H, m), 1.10 (3H, d, J = 7.4 Hz), 1.12 (3H, d, J = 7.2 Hz), 1.30-1.36 (3H, m), 1.33 (3H, d, J = 6.9 Hz), 1.50-1.63 (3H, m), 1.66 (3H, d, J = 5.8 Hz), 1.86-1.98 (14H, m), 2.45 (1H, d, J = 4.8 Hz), 2.90 (3H, s), 3.02 (3H, s), 3.05 (6H, s), 3.06 (3H, s), 3.17 (3H, s), 3.28 (3H, s), 3.37 (3H, s), 3.55 (1H, dd, J = 6.2, 9.7 Hz), 3.63 (1H, d, J = 1.8 Hz), 3.76 (1H, dd, J = 8.4, 9.5 Hz), 3.81-3.92 (3H, m), 4.08-4.17 (3H, m), 4.52 (1H, dd, J = 7.0, 8.9 Hz), 4.69 (1H, t, J = 7.3 Hz), 4.86 (1H, dd, J = 2.2, 9.2 Hz), 5.00 (1H, dd, J = 6.4, 8.2 Hz), 5.08 (1H, dd, J = 5.3, 10.2 Hz), 5.15 (1H, dd, J = 4.0, 11.4 Hz), 5.30 (1H, s), 5.31-5.38 (2H, m), 5.39-5.56 (2H, m), 5.65 (1H, d, J = 3.3 Hz), 6.76 (1H, d, J = 8.3 Hz), 6.90 (1H, d, J = 7.6 Hz), 7.00 (1H, d, J = 8.8 Hz), 7.65 (1H, d, J = 9.1 Hz), 9.17 (1H, d, J = 9.4 Hz). (for a major conformer) MS: 1392.07 |
| 130 | NMR: 0.71 (3H, d, J = 6.8 Hz) 0.81 (3H, d, J = 6.5 Hz), 0.82 (3H, d, J = 6.4 Hz), 0.85-1.04 (26H, m), 1.10 (3H, d, J = 6.5 Hz), 1.12 (3H, d, J = 6.9 Hz), |

TABLE 9-continued

| Ex | Data |
|---|---|
|  | 1.33 (3H, d, J = 7.0 Hz), 1.38 (3H, d, J = 7.4 Hz), 1.54-2.13 (18H, m), 2.18-2.29 (6H, m), 2.53-2.63 (5H, m), 2.90 (3H, s), 2.98 (3H, s), 3.04 (3H, s), 3.06 (6H, s), 3.19 (3H, s), 3.68-3.77 (6H, m), 3.94 (2H, dd, J = 6.4, 2.9 Hz), 4.20-4.29 (2H, m), 4.53 (1H, dd, J = 8.8, 6.9 Hz), 4.69 (1H, t-like, J = 7.1 Hz), 4.78-5.01 (3H, m), 5.06 (1H, dd, J = 10.2, 5.2 Hz), 5.15 (1H, dd, J = 11.4, 4.1 Hz), 5.33-5.54 (3H, m), 5.67 (1H, d, J = 3.1 Hz), 6.76 (1H, d, J = 8.2 Hz), 6.93 (1H, d, J = 7.5 Hz), 7.02 (1H, d, J = 9.0 Hz), 7.64 (1H, d, J = 9.0 Hz), 9.21 (1H, d, J = 9.3 Hz). (for a major conformer) MS: 1378.81 |
| 131 | NMR: 0.71 (3H, d, J = 6.8 Hz) 0.81 (3H, d, J = 6.5 Hz), 0.82 (3H, d, J = 6.4 Hz), 0.85-1.04 (26H, m), 1.10 (3H, d, J = 6.5 Hz), 1.12 (3H, d, J = 6.9 Hz), 1.33 (3H, d, J = 7.0 Hz), 1.38 (3H, d, J = 7.4 Hz), 1.54-2.13 (22H, m), 2.10-2.16 (4H, m), 2.26-2.48 (3H, m), 2.90 (3H, s), 2.98 (3H, s), 3.04 (3H, s), 3.06 (6H, s), 3.17 (3H, s), 3.52-3.63 (6H, m), 3.94 (2H, dd, J = 6.4, 2.9 Hz), 4.20-4.29 (2H, m), 4.53 (1H, dd, J = 8.8, 6.9 Hz), 4.69 (1H, t-like, J = 7.1 Hz), 4.78-5.01 (3H, m), 5.06 (1H, dd, J = 10.2, 5.2 Hz), 5.15 (1H, dd, J = 11.4, 4.1 Hz), 5.33-5.54 (3H, m), 5.67 (1H, d, J = 3.1 Hz), 6.76 (1H, d, J = 8.2 Hz), 6.93 (1H, d, J = 7.5 Hz), 7.02 (1H, d, J = 9.0 Hz), 7.64 (1H, d, J = 9.0 Hz), 9.21 (1H, d, J = 9.3 Hz). (for a major conformer) MS: 1396.01 |
| 132 | MS: 1418.30 |
| 133 | MS: 1436.74 |
| 134 | MS: 1406.86 |
| 135 | MS: 1406.59 |
| 136 | MS: 1420.76 |
| 137 | NMR: 0.71 (3H, d, J = 6.8 Hz) 0.81 (3H, d, J = 6.5 Hz), 0.82 (3H, d, J = 6.4 Hz), 0.85-1.04 (26H, m), 1.10 (3H, d, J = 6.5 Hz), 1.12 (3H, d, J = 6.9 Hz), 1.21 (6H, s), 1.33 (3H, d, J = 7.0 Hz), 1.38 (3H, d, J = 7.4 Hz), 1.54-2.13 (18H, m), 2.26-2.43 (2H, m), 2.47-2.62 (5H, m), 2.90 (3H, s), 2.98 (3H, s), 3.04 (3H, s), 3.06 (6H, s), 3.17 (3H, s), 3.22-3.25 (2H, m), 3.37-3.42 (3H, m), 3.65-3.72 (3H, m), 3.94 (2H, dd, J = 6.4, 2.9 Hz), 4.20-4.29 (2H, m), 4.53 (1H, dd, J = 8.8, 6.9 Hz), 4.69 (1H, t-like, J = 7.1 Hz), 4.78-5.01 (3H, m), 5.06 (1H, dd, J = 10.2, 5.2 Hz), 5.15 (1H, dd, J = 11.4, 4.1 Hz), 5.33-5.54 (3H, m), 5.67 (1H, d, J = 3.1 Hz), 6.76 (1H, d, J = 8.2 Hz), 6.92 (1H, d, J = 7.5 Hz), 7.01 (1H, d, J = 9.0 Hz), 7.64 (1H, d, J = 9.0 Hz), 9.16 (1H, d, J = 9.3 Hz). (for a major conformer) MS: 1390.64 |
| 138 | MS: 1450.54 |
| 139 | MS: 1428.46 |
| 140 | MS: 1408.51 |
| 141 | MS: 1346.56 |
| 142 | MS: 1394.60 |
| 143 | MS: 1373.38 |
| 144 | MS: 1404.74 |
| 145 | NMR: 0.71 (3H, d, J = 6.8 Hz) 0.81 (3H, d, J = 6.5 Hz), 0.82 (3H, d, J = 6.4 Hz), 0.85-1.04 (26H, m), 1.10 (3H, d, J = 6.5 Hz), 1.12 (3H, d, J = 6.9 Hz), 1.33 (3H, d, J = 7.0 Hz), 1.38 (3H, d, J = 7.4 Hz), 1.54-2.51 (27H, m), 2.90 (3H, s), 2.98 (3H, s), 3.02 (3H, s), 3.04 (6H, s), 3.08 (3H, s), 3.16 (3H, s), 3.61-3.98 (4H, m), 4.20-4.29 (2H, m), 4.53 (1H, dd, J = 8.8, 6.9 Hz), 4.69 (1H, t-like, J = 7.1 Hz), 4.78-5.01 (3H, m), 5.06 (1H, dd, J = 10.2, 5.2 Hz), 5.15 (1H, dd, J = 11.4, 4.1 Hz), 5.33-5.54 (3H, m), 5.67 (1H, d, J = 3.1 Hz), 6.77 (1H, d, J = 8.2 Hz), 6.88 (1H, d, J = 7.5 Hz), 6.99 (1H, br s), 7.64 (1H, d, J = 8.3 Hz), 8.99 (1H, d, J = 8.8 Hz). (for a major conformer) MS: 1388.48 |
| 146 | MS: 1390.41 |
| 147 | NMR: 0.71 (3H, d, J = 6.8 Hz), 0.81 (6H, d, J = 6.5 Hz), 0.87 (3H, d, J = 6.5 Hz), 0.88 (3H, d, J = 6.4 Hz), 0.90-0.96 (9H, m), 0.99 (3H, d, J = 6.6 Hz), 1.00 (3H, d, J = 6.4 Hz), 1.02 (3H, d, J = 5.8 Hz), 1.10 (3H, d, J = 6.7 Hz), 1.12 (3H, d, J = 7.8 Hz), |

TABLE 9-continued

| Ex | Data |
|---|---|
|  | 1.33 (3H, d, J = 6.8 Hz), 1.38-1.62 (4H, m), 1.66 (3H, d, J = 5.6 Hz), 1.67-2.40 (37H, m), 2.90 (3H, s), 3.03 (3H, s), 3.05 (6H, s), 3.07 (3H, s), 3.17 (3H, s), 3.37 (3H, s), 3.55 (1H, dd, J = 6.5, 9.7 Hz), 3.62 (1H, dd, J = 6.1, 11.2 Hz), 3.70-3.83 (2H, m), 3.84-3.93 (1H, m), 3.98 (1H, dd, J = 5.8, 10.6 Hz), 4.17-4.35 (3H, m), 4.52 (1H, dd, J = 6.9, 9.0 Hz), 4.69 (1H, t, J = 7.0 Hz), 4.74-4.83 (1H, m), 4.86 (1H, dd, J = 2.0, 9.4 Hz), 4.90-5.04 (2H, m), 5.08 (1H, dd, J = 5.2, 10.0 Hz), 5.15 (1H, dd, J = 3.8, 11.5 Hz), 5.30-5.38 (3H, m), 5.39-5.55 (2H, m), 5.65 (1H, d, J = 3.2 Hz), 6.76 (1H, d, J = 8.2 Hz), 7.04 (1H, d, J = 9.2 Hz), 7.65 (1H, d, J = 9.1 Hz), 9.25 (1H, d, J = 9.3 Hz). (for a major conformer) |
| 148 | NMR: 0.70 (3H, d, J = 6.8 Hz), 0.81 (6H, d, J = 6.4 Hz), 0.87 (3H, d, J = 6.4 Hz), 0.88 (3H, d, J = 6.3 Hz), 0.92 (3H, d, J = 6.7 Hz), 0.93 (3H, d, J = 6.3 Hz), 0.94 (3H, d, J = 6.8 Hz), 0.97-1.03 (12H, m), 1.10 (3H, d, J = 6.6 Hz), 1.12 (3H, d, J = 8.1 Hz), 1.26 (1H, s), 1.33 (3H, d, J = 6.8 Hz), 1.52-2.50 (40H, m), 2.90 (3H, s), 3.03 (3H, s), 3.05 (6H, s), 3.07 (3H, s), 3.17 (3H, s), 3.37 (3H, s), 3.55 (1H, dd, J = 6.3, 9.7 Hz), 3.59-3.68 (1H, m), 3.72-3.82 (2H, m), 3.86-4.06 (3H, m), 4.17-4.32 (3H, m), 4.52 (1H, dd, J = 6.9, 9.0 Hz), 4.69 (1H, t, J = 7.1 Hz), 4.74-4.82 (1H, m), 4.86 (1H, dd, J = 1.7, 9.0 Hz), 4.89-4.98 (1H, m), 5.00 (1H, dd, J = 6.5, 8.0 Hz), 5.08 (1H, dd, J = 5.1, 9.9 Hz), 5.15 (1H, dd, J = 4.2, 11.8 Hz), 5.28-5.56 (4H, m), 5.65 (1H, d, J = 3.2 Hz), 6.76 (1H, d, J = 8.2 Hz), 6.94 (1H, d, J = 7.4 Hz), 7.05 (1H, d, J = 9.1 Hz), 7.65 (1H, d, J = 9.2 Hz), 9.24 (1H, d, J = 9.3 Hz). (for a major conformer) |
| 149 | MS: 1434.69 |
| 150 | MS: 1434.71 |
| 151 | NMR: 0.71 (3H, d, J = 6.8 Hz), 1.48-0.78 (20H, m), 0.81 (3H, d, J = 6.4 Hz), 0.85 (3H, d, J = 6.8 Hz), 0.88 (3H, d, J = 6.9. Hz), 0.92 (3H, d, J = 6.7 Hz), 0.94 (3H, d, J = 6.6 Hz), 1.10 (3H, d, J = 6.8 Hz), 1.12 (3H, d, J = 7.2 Hz), 1.34 (3H, d, J = 6.8 Hz), 2.17-1.50 (17H, m), 1.66 (3H, d, J = 5.6 Hz), 2.82-2.22 (5H, m), 2.90 (3H, s), 3.02 (3H, s), 3.05 (3H, s), 3.06 (6H, s), 3.17 (3H, s), 3.32 (3H, s), 3.37 (3H, s), 3.48-3.40 (4H, m), 3.55 (1H, dd, J = 9.6, 6.4 Hz), 3.76 (1H, dd, J = 9.4, 8.6 Hz), 3.99-3.83 (3H, m), 4.21 (1H, dd, J = 6.4, 2.0 Hz), 4.28 (1H, dd, J = 10.5, 3.1 Hz), 4.52 (1H, dd, J = 8.8, 7.0 Hz), 4.69 (1H, t-like, J = 7.0 Hz), 4.83-4.74 (1H, m), 4.86 (1H, dd, J = 9.2, 2.0 Hz), 5.04-4.91 (2H, m), 5.08 (1H, dd, J = 10.1, 5.2 Hz), 5.15 (1H, dd, J = 11.5, 4.0 Hz), 5.55-5.28 (4H, m), 5.65 (1H, d, J = 3.1 Hz), 6.76 (1H, d, J = 8.1 Hz), 6.92 (1H, d, J = 7.2 Hz), 7.01 (1H, d, J = 9.0 Hz), 7.66 (1H, d, J = 8.8 Hz), 9.19 (1H, d, J = 9.2 Hz). (for a major conformer) MS: 1406.56 |
| 152 | NMR: 0.71 (3H, d, J = 6.8 Hz), 0.78-1.48 (20H, m), 0.81 (3H, d, J = 6.5 Hz), 0.87 (3H, d, J = 6.8 Hz), 0.89 (3H, d, J = 7.0 Hz), 0.92 (3H, d, J = 6.7 Hz), 0.94 (3H, d, J = 6.5 Hz), 1.10 (3H, d, J = 6.7 Hz), 1.12 (3H, d, J = 7.2 Hz), 1.33 (3H, d, J = 6.8 Hz), 1.50-2.17 (17H, m), 1.66 (3H, d, J = 5.5 Hz), 2.22-2.82 (5H, m), 2.90 (3H, s), 3.02 (3H, s), 3.05 (3H, s), 3.06 (6H, s), 3.16 (3H, s), 3.32 (3H, s), 3.37 (3H, s), 3.40-3.48 (4H, m), 3.55 (1H, dd, J = 9.6, 6.4 Hz), 3.76 (1H, dd, J = 9.5, 8.6 Hz), 3.83-3.99 (3H, m), 4.22 (1H, dd, J = 6.4, 2.1 Hz), 4.28 (1H, dd, J = 10.5, 3.2 Hz), 4.52 (1H, dd, J = 8.8, 7.0 Hz), 4.70 (1H, t-like, J = 7.2 Hz), 4.74-4.83 (1H, m), 4.86 (1H, dd, J = 9.4, 2.2 Hz), 4.91-5.04 (2H, m), 5.08 (1H, dd, J = 10.1, 5.2 Hz), 5.15 (1H, dd, J = 11.5, 4.1 Hz), 5.28-5.55 (4H, m), 5.65 (1H, d, J = 3.2 Hz), 6.76 (1H, d, J = 8.1 Hz), 6.91 (1H, d, J = 7.2 Hz), 7.01 (1H, d, J = 8.7 Hz), 7.66 (1H, d, J = 9.1 Hz), 9.17 (1H, d, J = 9.3 Hz) (for a major conformer). MS: 1406.50 |
| 153 | MS: 1390.24 |
| 154 | MS: 1434.22 |
| 155 | MS: 1462.29 |

TABLE 9-continued

| Ex | Data |
| --- | --- |
| 156 | MS: 1376.22 |
| 157 | MS: 1420.56 |
| 158 | MS: 1420.28 |
| 159 | MS: 1464.97 |
| 160 | MS: 1466.96 |
| 161 | MS: 1467.10 |
| 162 | MS: 1469.80 |
| 163 | MS: 1499.94 |
| 164 | MS: 1406.02 |
| 165 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (9H, m), 2.22-2.72 (9H, m), 2.90 (6H, s), 2.91 (3H, s), 2.97 (3H, s), 3.05 (3H, s), 3.06 (3H, s), 3.08 (3H, s), 3.17 (3H, s), 3.31 (3H, s), 3.84-3.95 (2H, m), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.76 (1H, d, J = 8.3 Hz), 6.87 (1H, d, J = 7.4 Hz), 6.99 (1H, d, J = 9.0 Hz), 7.64 (1H, d, J = 9.0 Hz), 8.93 (1H, br s). (for a major conformer) MS: 1320.14 |
| 166 | MS: 1470.10 |
| 167 | MS: 1362.39 |
| 168 | MS: 1362.39 |
| 169 | MS: 1390.37 |
| 170 | MS: 1363.40 |
| 171 | NMR: 0.71 (3H, d, J = 6.8 Hz), 0.78-2.14 (34H, m), 0.81 (3H, d, J = 6.5 Hz), 0.82 (3H, d, J = 6.5 Hz), 0.87 (3H, d, J = 6.7 Hz), 0.89 (3H, d, J = 6.8 Hz), 0.91 (3H, d, J = 6.6 Hz), 0.95 (3H, d, J = 6.4 Hz), 1.10 (3H, d, J = 6.5 Hz), 1.12 (3H, d, J = 7.0 Hz), 1.33 (3H, d, J = 6.9 Hz), 1.38 (3H, d, J = 7.4 Hz), 1.66 (3H, d, J = 5.5 Hz), 2.24-2.48 (3H, m), 2.91 (3H, s), 2.97 (3H, s), 3.05 (3H, s), 3.05 (3H, s), 3.08 (3H, s), 3.17 (3H, s), 3.32 (3H, s), 3.36-3.56 (5H, m), 3.80-3.98 (3H, m), 4.21 (1H, dd, J = 6.4, 2.1 Hz), 4.28 (1H, dd, J = 10.3, 3.2 Hz), 4.53 (1H, dd, J = 8.9, 7.0 Hz), 4.70 (1H, t, J = 6.9 Hz), 4.76-5.02 (4H, m), 5.07 (1H, dd, J = 10.1, 5.1 Hz), 5.15 (1H, dd, J = 11.2, 4.0 Hz), 5.28-5.58 (4H, m), 5.67 (1H, d, J = 3.3 Hz), 6.76 (1H, d, J = 8.4 Hz), 6.86 (1H, d, J = 7.4 Hz), 6.98 (1H, d, J = 9.6 Hz), 7.64 (1H, d, J = 8.8 Hz), 8.93 (1H, d, J = 9.6 Hz). (for a major conformer) MS: 1393.05 |
| 172 | NMR: 0.71 (3H, d, J = 6.8 Hz), 0.78-2.14 (34H, m), 0.81 (3H, d, J = 6.5 Hz), 0.82 (3H, d, J = 6.5 Hz), 0.87 (3H, d, J = 6.6 Hz), 0.89 (3H, d, J = 6.7 Hz), 0.92 (3H, d, J = 6.7 Hz), 0.95 (3H, d, J = 6.4 Hz), 1.10 (3H, d, J = 6.4 Hz), 1.12 (3H, d, J = 6.9 Hz), 1.33 (3H, d, J = 6.8 Hz), 1.38 (3H, d, J = 7.4 Hz), 1.66 (3H, d, J = 5.4 Hz), 2.24-2.48 (3H, m), 2.91 (3H, s), 2.97 (3H, s), 3.05 (3H, s), 3.05 (3H, s), 3.08 (3H, s), 3.17 (3H, s), 3.32 (3H, s), 3.36-3.56 (5H, m), 3.80-3.98 (3H, m), 4.17-4.24 (1H, m), 4.28 (1H, dd, J = 10.8, 3.3 Hz), 4.48-4.57 (1H, m), 4.70 (1H, t, J = 7.0 Hz), 4.76-5.02 (4H, m), 5.07 (1H, dd, J = 10.1, 5.1 Hz), 5.15 (1H, dd, J = 11.4, 4.2 Hz), 5.28-5.58 (4H, m), 5.67 (1H, d, J = 3.3 Hz), 6.76 (1H, d, J = 8.4 Hz), 6.86 (1H, d, J = 8.0 Hz), 6.98 (1H, d, J = 10.2 Hz), 7.64 (1H, d, J = 9.0 Hz), 8.95 (1H, d, J = 9.4 Hz). (for a major conformer) MS: 1376.09 |
| 173 | MS: 1376.25 |
| 174 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (11H, m), 2.22-2.72 (7H, m), 2.89 (3H, s), 2.91 (3H, s), 2.98 (3H, s), 3.05 (3H, s), 3.06 (3H, s), 3.07 (3H, s), 3.17 (3H, s), 3.26-3.50 (6H, m), 3.31 (3H, s), 3.84-3.95 (2H, m), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.76 (1H, d, J = 8.2 Hz), 6.89 (1H, d, J = 7.5 Hz), 6.99 (1H, d, J = 9.0 Hz), 7.63 (1H, d, J = 9.0 Hz), 9.06 (1H, d, J = 8.8 Hz). (for a major conformer) MS: 1378.86. |
| 175 | MS: 1408.11 |
| 176 | NMR: 0.71 (3H, d, J = 6.8 Hz), 0.78-2.54 (37H, m), 0.81 (3H, d, J = 6.5 Hz), 0.82 (3H, d, J = 6.5 Hz), 0.87 (3H, d, J = 6.7 Hz), 0.89 (3H, d, J = 6.8 Hz), 0.92 (3H, d, J = 7.0 Hz), 0.95 (3H, d, J = 6.5 Hz), 1.10 (3H, d, J = 6.4 Hz), 1.12 (3H, d, J = 7.0 Hz), 1.33 (3H, d, J = 6.8 Hz), 1.38 (3H, d, J = 7.4 Hz), 1.66 (3H, d, J = 5.5 Hz), 2.86-3.24 (3H, m), 2.90 (3H, s), 2.98 (3H, s), 3.04 (3H, s), 3.05 (3H, s), 3.07 (3H, s), 3.17 (3H, s), 3.40-3.60 (4H, m), 3.67-3.74 (1H, m), 3.87-3.98 (3H, m), 4.16-4.34 (2H, m), 4.52 (1H, dd, J = 8.8, 6.9 Hz), 4.69 (1H, t, J = 7.0 Hz), 4.76-5.02 (4H, m), 5.06 (1H, dd, J = 10.1, 5.2 Hz), 5.11-5.28 (1H, m), 5.29-5.57 (4H, m), 5.67 (1H, d, J = 3.2 Hz), 5.78-5.94 (1H, m), 6.76 (1H, d, J = 8.1 Hz), 6.91 (1H, d, J = 7.5 Hz), 7.00 (1H, d, J = 9.0 Hz), 7.62 (1H, d, J = 9.2 Hz), 9.15 (1H, d, J = 9.3 Hz). (for a major conformer) MS: 1399.92 |
| 177 | MS: 1443.90 |
| 178 | MS: 1378.16 |
| 179 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (9H, m), 2.22-2.72 (9H, m), 2.91 (3H, s), 2.98 (3H, s), 3.05 (3H, s), 3.07 (6H, s), 3.17 (3H, s), 3.60 (8H, s), 3.84-3.95 (2H, m), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.76 (1H, d, J = 8.3 Hz), 6.93 (1H, d, J = 7.4 Hz), 7.01 (1H, d, J = 9.2 Hz), 7.62 (1H, d, J = 8.9 Hz), 7.89 (1H, s), 8.09 (1H, s), 8.15 (1H, s), 9.16 (1H, d, J = 9.1 Hz). (for a major conformer) MS: 1439.34 |
| 180 | MS: 1440.17 |
| 181 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (9H, m), 2.22-2.72 (9H, m), 2.30 (6H, s), 2.91 (3H, s), 2.98 (3H, s), 3.04 (3H, s), 3.06 (3H, s), 3.07 (3H, s), 3.17 (3H, s), 3.52 (4H, br s), 3.82 (4H, br s), 3.84-3.95 (2H, m), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.31 (1H, s), 6.76 (1H, d, J = 8.2 Hz), 6.91 (1H, d, J = 7.4 Hz), 7.01 (1H, d, J = 9.0 Hz), 7.63 (1H, d, J = 9.0 Hz), 9.13 (1H, d, J = 9.2 Hz). (for a major conformer) MS: 1466.98 |
| 182 | MS: 1346.12 |
| 183 | NMR: 0.71 (3H, d, J = 6.9 Hz), 0.82 (6H, d, J = 6.5 Hz), 0.84-0.92 (12H, m), 0.95 (3H, d, J = 6.6 Hz), |

TABLE 9-continued

| Ex | Data |
|---|---|
|  | 0.97-1.01 (9H, m), 1.03 (3H, d, J = 6.4 Hz), 1.10 (3H, d, J = 6.5 Hz), 1.13 (3H, d, J = 7.0 Hz), 1.30-1.40 (6H, m), 1.50-1.63 (3H, m), 1.66 (3H, d, J = 5.8 Hz), 1.70-2.44 (35H, m), 2.90 (3H, s), 2.99 (3H, s), 3.04 (3H, s), 3.06 (3H, s), 3.09 (3H, s), 3.17 (3H, s), 3.34-3.44 (1H, m), 3.45-3.53 (1H, m), 4.18-4.25 (1H, m), 4.28 (1H, dd, J = 3.3, 10.6 Hz), 4.52 (1H, dd, J = 7.0, 8.8 Hz), 4.70 (1H, t, J = 7.3 Hz), 4.76-4.91 (3H, m), 4.91-5.01 (1H, m), 5.07 (1H, dd, J = 5.2, 10.0 Hz), 5.15 (1H, dd, J = 4.2, 11.6 Hz), 5.28-5.38 (2H, m), 5.38-5.58 (2H, m), 5.67 (1H, d, J = 3.4 Hz), 6.76 (1H, d, J = 8.2 Hz), 6.94 (1H, d, J = 7.6 Hz), 7.03 (1H, d, J = 9.0 Hz), 7.65 (1H, d, J = 9.0 Hz), 9.23 (1H, d, J = 9.6 Hz). (for a major conformer) |
| 184 | MS: 1404.47 |
| 185 | NMR: 0.71 (3H, d, J = 6.9 Hz), 0.81 (3H, d, J = 6.2 Hz), 0.82 (3H, d, J = 6.5 Hz), 0.84-0.97 (18H, m), 0.97-1.01 (9H, m), 1.03 (3H, d, J = 6.5 Hz), 1.10 (3H, d, J = 6.5 Hz), 1.12 (3H, d, J = 6.5 Hz), 1.25 (3H, s), 1.33 (3H, d, J = 7.0 Hz), 1.38 (3H, d, J = 7.3 Hz), 1.52-2.34 (37H, m), 2.90 (3H, s), 2.98 (3H, s), 3.04 (3H, s), 3.06 (3H, s), 3.07 (3H, s), 3.17 (3H, s), 3.58-3.68 (2H, m), 3.76-3.84 (1H, m), 3.88-4.09 (3H, m), 4.18-4.32 (3H, m), 4.52 (1H, dd, J = 6.8, 9.0 Hz), 4.70 (1H, t, J = 7.2 Hz), 4.89-5.00 (3H, m), 5.06 (1H, dd, J = 5.2, 10.0 Hz), 5.15 (1H, dd, J = 4.3, 11.5 Hz), 5.32-5.42 (1H, m), 5.42-5.54 (1H, m), 5.67 (1H, d, J = 3.4 Hz), 6.76 (1H, d, J = 8.5 Hz), 6.93 (1H, d, J = 7.4 Hz), 7.04 (1H, d, J = 8.9 Hz), 7.63 (1H, d, J = 9.0 Hz), 9.22 (1H, d, J = 9.5 Hz). (for a major conformer) |
| 186 | NMR: 0.71 (3H, d, J = 6.8 Hz), 0.79-1.05 (10H, m), 0.81 (3H, d, J = 6.5 Hz), 0.82 (3H, d, J = 6.5 Hz), 0.87 (3H, d, J = 6.8 Hz), 0.89 (3H, d, J = 6.7 Hz), 0.92 (3H, d, J = 6.7 Hz), 0.95 (3H, d, J = 6.6 Hz), 1.10 (3H, d, J = 6.4 Hz), 1.12 (3H, d, J = 6.9 Hz), 1.32 (3H, d, J = 6.7 Hz), 1.38 (3H, d, J = 7.3 Hz), 1.51-1.64 (4H, m), 1.66 (3H, d, J = 5.6 Hz), 1.69-2.16 (10H, m), 2.27-2.87 (7H, m), 2.90 (3H, s), 2.96 (3H, s), 2.99 (3H, s), 3.05 (3H, s), 3.06 (6H, s), 3.17 (3H, s), 3.24-3.60 (6H, m), 3.37 (3H, s), 3.43 (3H, s), 3.91 (2H, d, J = 5.3 Hz), 4.21 (1H, dd, J = 6.5, 1.9 Hz), 4.28 (1H, dd, J = 10.4, 3.1 Hz), 4.53 (1H, dd, J = 8.8, 7.0 Hz), 4.70 (1H, t-like, J = 7.1 Hz), 4.75-5.04 (4H, m), 5.07 (1H, dd, J = 10.1, 5.2 Hz), 5.15 (1H, dd, J = 11.4, 4.0 Hz), 5.30-5.58 (3H, m), 5.36 (2H, d, J = 10.4 Hz), 5.67 (1H, d, J = 3.1 Hz), 6.76 (1H, d, J = 8.2 Hz), 6.94 (1H, d, J = 7.3 Hz), 7.01 (1H, d, J = 8.9 Hz), 7.64 (1H, d, J = 9.0 Hz), 9.24 (1H, br-s) . (for a major conformer) MS: 1408.16 |
| 187 | NMR: 0.71 (3H, d, J = 6.7 Hz), 0.81 (3H, d, J = 6.4 Hz), 0.82 (3H, d, J = 6.4 Hz), 1.05-0.84 (10H, m), 0.87 (3H, d, J = 6.9 Hz), 0.89 (3H, d, J = 6.7 Hz), 0.92 (3H, d, J = 6.7 Hz), 0.95 (3H, d, J = 6.5 Hz), 1.10 (3H, d, J = 6.5 Hz), 1.12 (3H, d, J = 6.9 Hz), 1.33 (3H, d, J = 6.7 Hz), 1.38 (3H, d, J = 7.4 Hz), 1.64-1.51 (4H, m), 1.66 (3H, d, J = 5.5 Hz), 2.16-1.69 (10H, m), 2.87-2.27 (7H, m), 2.90 (3H, s), 2.96 (3H, s), 2.98 (3H, s), 3.05 (3H, s), 3.06 (6H, s), 3.17 (3H, s), 3.37 (3H, s), 3.43 (3H, s), 3.59-3.26 (6H, m), 3.98-3.84 (2H, m), 4.25-4.17 (1H, m), 4.28 (1H, dd, J = 10.5, 3.0 Hz), 4.52 (1H, dd, J = 8.6, 7.1 Hz), 4.70 (1H, t-like, J = 7.1 Hz), 5.03-4.76 (4H, m), 5.07 (1H, dd, J = 10.1, 5.2 Hz), 5.15 (1H, dd, J = 11.4, 4.0 Hz), 5.59-5.31 (3H, m), 5.36 (2H, d, J = 10.4 Hz), 5.67 (1H, d, J = 3.0 Hz), 6.76 (1H, d, J = 8.2 Hz), 6.92 (1H, d, J = 7.4 Hz), 7.01 (1H, d, J = 8.8 Hz), 7.64 (1H, d, J = 9.0 Hz), 9.18 (1H, d, J = 9.3 Hz). (for a major conformer) MS: 1408.16 |
| 188 | MS: 1471.95 |
| 189 | MS: 1404.80 |
| 190 | MS: 1431.86 |
| 191 | 1NMR: 0.71 (3H, d, J = 6.8 Hz), 0.78-1.48 (17H, m), 0.81 (3H, d, J = 6.5 Hz), 0.82 (3H, d, J = 6.4 Hz), 0.87 (3H, d, J = 6.8 Hz), 0.92 (3H, d, J = 6.7 Hz), 0.94 (3H, d, J = 6.8 Hz), 0.95 (3H, d, J = 6.5 Hz), 1.05 (6H, d, J = 6.6 Hz), 1.10 (3H, d, J = 6.4 Hz), 1.13 (3H, d, J = 6.9 Hz), 1.34 (3H, d, J = 6.9 Hz), 1.38 (3H, d, J = 7.5 Hz), 1.50-2.18 (13H, m), 1.66 (3H, d, J = 5.6 Hz), 2.24-2.78 (10H, m), 2.90 (3H, s), 2.99 (3H, s), 3.05 (3H, s), 3.05 (3H, s), 3.06 (3H, s), 3.17 (3H, s), 3.42-3.54 (4H, m), 3.70-3.77 (1H, m), 3.88-3.98 (2H, m), 4.18-4.33 (2H, m), 4.48-4.57 (1H, m), 4.69 (1H, t, J = 7.1 Hz), 4.76-5.04 (4H, m), 5.07 (1H, dd, J = 10.1, 5.3 Hz), 5.15 (1H, dd, J = 11.4, 4.0 Hz), 5.30-5.56 (4H, m), 5.67 (1H, d, J = 3.3 Hz), 6.76 (1H, d, J = 8.2 Hz), 6.97 (1H, d, J = 7.4 Hz), 7.03 (1H, d, J = 9.0 Hz), 7.64 (1H, d, J = 9.0 Hz), 9.29 (1H, d, J = 9.2 Hz). (for a major conformer) MS: 1402.85 |
| 192 | MS: 1457.92 |
| 193 | MS: 1390.87 |
| 194 | MS: 1432.84 |
| 195 | MS: 1445.95 |
| 196 | NMR: 0.71 (3H, d, J = 6.8 Hz), 0.81 (3H, d, J = 6.5 Hz), 0.82 (3H, d, J = 6.5 Hz), 0.87 (3H, d, J = 6.7 Hz), 0.90 (3H, d, J = 4.2 Hz), 0.93 (3H, d, J = 4.8 Hz), 0.95 (3H, d, J = 6.5 Hz), 0.99 (3H, d, J = 6.8 Hz), 1.00 (3H, d, J = 6.6 Hz), 1.03 (3H, d, J = 6.5 Hz), 1.07-1.15 (9H, m), 1.33 (3H, d, J = 6.8 Hz), 1.38 (3H, d, J = 7.4 Hz), 1.52-1.65 (2H, m), 1.66 (3H, d, J = 5.4 Hz), 1.70-2.15 (8H, m), 2.15-2.22 (16H, m), 2.24-2.42 (3H, m), 2.90 (3H, s), 2.96 (3H, s), 2.99 (3H, s), 3.04 (3H, s), 3.06 (6H, s), 3.17 (3H, s), 3.29-3.38 (4H, m), 3.42-3.60 (1H, m), 3.84-3.97 (3H, m), 4.21 (1H, dd, J = 2.1, 6.6 Hz), 4.28 (1H, dd, J = 3.3, 10.5 Hz), 4.52 (1H, dd, J = 6.6, 9.2 Hz), 4.70 (1H, t, J = 6.6 Hz), 4.78-4.90 (3H, m), 4.91-5.01 (1H, m), 5.06 (1H, dd, J = 5.6, 10.2 Hz), 5.15 (1H, dd, J = 4.1, 11.2 Hz), 5.5-5.4 (2H, m), 5.40-5.57 (1H, m), 5.67 (1H, d, J = 3.6 Hz), 6.76 (1H, d, J = 8.2 Hz), 7.00 (1H, d, J = 8.7 Hz), 7.64 (1H, d, J = 9.1 Hz), 9.25 (1H, d, J = 9.2 Hz). (for a major conformer) MS: 1378.46 |
| 197 | MS: 1378.46 |
| 198 | MS: 1402.45 |
| 199 | MS: 1405.98 |
| 200 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (9H, m), 2.22-2.72 (9H, m), 2.90 (3H, s), 2.98 (3H, s), 3.04 (3H, s), 3.05 (3H, s), 3.06 (3H, s), 3.19 (3H, s), 3.36 (6H, s), 3.40-3.57 (4H, m), 3.76-3.83 (2H, m), 3.84-3.95 (2H, m), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.76 (1H, d, J = 8.3 Hz), 6.90 (1H, d, J = 7.4 Hz), 7.00 (1H, d, J = 9.0 Hz), 7.64 (1H, d, J = 9.0 Hz), 9.19 (1H, d, J = 9.6 Hz). (for a major conformer) MS: 1406.00 |
| 201 | MS: 1432.48 |
| 202 | MS: 1420.45 |
| 203 | NMR: 0.71 (3H, d, J = 6.8 Hz), 0.81 (3H, d, J = 6.5 Hz), 0.81 (3H, d, J = 6.5 Hz), 0.87 (3H, d, J = 6.6 Hz), 0.88-1.03 (26H, m), 1.09 (3H, d, J = 6.6 Hz), 1.12 (3H, d, J = 7.1 Hz), 1.33 (3H, d, J = 6.7 Hz), 1.16-2.20 (21H, m), 2.24-2.96 (5H, m), 2.91 (3H, s), 3.03 (3H, s), 3.04 (3H, s), 3.05 (6H, s), 3.17 (3H, s), 3.37 (3H, s), 3.38 (3H, s), 3.40-3.47 (2H, m), 3.47-3.70 (4H, m), 3.73-4.04 (7H, m), 4.17-4.29 (2H, m), 4.69 (1H, t-like, J = 7.1 Hz), 4.74-4.83 (1H, m), 4.86 (1H, dd, J = 9.2, 2.0 Hz), 4.91-5.02 (2H, m), 5.07 (1H, dd, J = 10.2, 5.3 Hz), 5.15 (1H, dd, J = 11.5, 4.0 Hz), 5.31-5.39 (2H, m), 5.67 (1H, d, J = 3.2 Hz), |

TABLE 9-continued

| Ex | Data |
|---|---|
|  | 6.77 (1H, d, J = 8.1 Hz), 6.95 (1H, d, J = 7.4 Hz), 7.02 (1H, d, J = 8.8 Hz), 7.64 (1H, d, J = 9.0 Hz), 9.27 (1H, d, J = 9.2 Hz). (for a major conformer) MS: 1437.92 |
| 204 | NMR: 0.71 (3H, d, J = 6.8 Hz), 0.81 (3H, d, J = 6.5 Hz), 0.82 (3H, d, J = 6.4 Hz), 0.84-1.07 (11H, m), 0.87 (3H, d, J = 6.6 Hz), 0.89 (3H, d, J = 6.9 Hz), 0.92 (3H, d, J = 6.6 Hz), 0.94 (3H, d, J = 6.5 Hz), 0.95 (3H, d, J = 6.8 Hz), 1.10 (3H, d, J = 6.5 Hz), 1.12 (3H, d, J = 6.9 Hz), 1.33 (3H, d, J = 6.8 Hz), 1.37 (3H, d, J = 7.4 Hz), 1.48-1.69 (9H, m), 1.69-2.16 (9H, m), 2.22-2.72 (9H, m), 2.90 (3H, s), 2.90 (3H, s), 2.99 (3H, s), 3.04 (3H, s), 3.06 (3H, s), 3.08 (3H, s), 3.17 (3H, s), 3.36-3.53 (2H, m), 3.74 (1H, br-s), 4.21 (1H, dd, J = 6.4, 2.1 Hz), 4.27 (1H, dd, J = 10.6, 3.4 Hz), 4.53 (1H, dd, J = 8.8, 6.9 Hz), 4.70 (1H, t-like, J = 7.1 Hz), 4.76-5.02 (3H, m), 5.07 (1H, dd, J = 10.2, 5.2 Hz), 5.15 (1H, dd, J = 11.3, 4.1 Hz), 5.33-5.51 (3H, m), 5.66 (1H, d, J = 3.3 Hz), 6.76 (1H, d, J = 8.3 Hz), 6.95 (1H, d, J = 7.5 Hz), 7.03 (1H, d, J = 9.0 Hz), 7.65 (1H, d, J = 8.9 Hz), 9.28 (1H, d, J = 9.3 Hz). MS: 1248.80 Retention time: 5.4 minitues (HPLC, column: Shiseido UG120 C18, 100 mm × 4.6 mm ID, eluent: 60% MeCN/H₂O, flow rate: 1.0 ml/minute) |
| 205-A | MS: 1261.58 |
| 205-B | MS: 1275.59 |
| 206 | MS: 1303.88 |
| 207 | MS: 1361.91 |
| 208 | MS: 1346.03 |
| 209 | MS: 1389.17 |
| 210 | MS: 1347.18 |
| 211 | MS: 1361.08 |
| 212 | NMR: 0.68 (3H, d, J = 6.6 Hz), 0.80 (3H, d, J = 6.5 Hz), 0.85 (3H, d, J = 6.7 Hz), 0.87 (3H, d, J = 6.6 Hz), 0.90 (3H, d, J = 7.0 Hz), 0.90-1.50 (24H, m), 1.50-1.65 (3H, m), 1.66 (3H, d, J = 5.7 Hz), 1.66-2.20 (12H, m), 2.21-2.88 (20H, m), 2.90 (3H, s), 2.98 (3H, s), 3.04 (3H, s), 3.06 (3H, s), 3.10 (3H, s), 3.16 (3H, s), 3.35-3.70 (2H, m), 3.85-4.05 (4H, m), 4.06-4.20 (2H, m), 4.51 (1H, t-like, J = 7.0 Hz), 4.67 (1H, t-like, J = 7.2 Hz), 4.75-5.10 (5H, m), 5.15 (1H, dd, J = 11.4, 4.0 Hz), 5.20-5.60 (3H, m), 5.66 (1H, d, J = 3.2 Hz), 6.78 (1H, d, J = 8.2 Hz), 6.95 (1H, d, J = 7.4 Hz), 7.15 (1H, d, J = 8.9 Hz), 7.58 (1H, d, J = 8.8 Hz), 9.22 (1H, d, J = 9.3 Hz). (for a major conformer) MS: 1317.82 |
| 213 | MS: 1316.13 |
| 214 | MS: 1352.99 |
| 215 | MS: 1331.89 |
| 216 | MS: 1329.80 |
| 217 | MS: 1319.96 |
| 218 | MS: 1330.06 |
| 219 | NMR: 0.71 (3H, d, J = 6.7 Hz), 0.80 (3H, d, J = 6.5 Hz), 0.85 (3H, d, J = 6.7 Hz), 0.87 (3H, d, J = 6.6 Hz), 0.90 (3H, d, J = 7.0 Hz), 0.92-0.99 (8H, m), 1.10 (3H, d, J = 6.5 Hz), 1.13 (3H, d, J = 7.1 Hz), 1.21-1.51 (10H, m), 1.51-1.65 (3H, m), 1.66 (3H, d, J = 5.6 Hz), 1.67-2.45 (31H, m), 2.46 (1H, d, J = 4.9 Hz), 2.56 (1H, d, J = 10.8 Hz), 2.69 (1H, d, J = 10.8 Hz), 2.90 (3H, s), 2.98 (3H, s), 3.04 (3H, s), 3.05 (3H, s), 3.06 (3H, s), 3.25-3.35 (1H, m), 3.35 (3H, s), 3.36-3.50 (1H, m), 3.55-3.75 (4H, m), 3.85 (1H, d, J = 10.4 Hz), 4.15-4.40 (3H, m), 4.54 (1H, t-like, J = 7.0 Hz), 4.71 (1H, t-like, J = 7.2 Hz), 4.78-5.10 (5H, m), 5.15 (1H, dd, J = 11.4, 4.0 Hz), 5.20-5.60 (3H, m), 5.67 (1H, d, J = 3.2 Hz), 6.76 (1H, d, J = 8.2 Hz), 6.94 (1H, d, J = 7.2 Hz), 6.97 (1H, d, J = 8.8 Hz), 7.65 (1H, d, J = 8.8 Hz), 9.23 (1H, d, J = 9.3 Hz). (for a major conformer) MS: 1362.05 |
| 220 | MS: 1362.02 |
| 221 | NMR: 0.71 (3H, d, J = 6.7 Hz), 0.80 (3H, d, J = 6.5 Hz), 0.85 (3H, d, J = 6.7 Hz), 0.87 (3H, d, J = 6.6 Hz), 0.90 (3H, d, J = 7.0 Hz), 0.92-0.97 (8H, m), 1.10 (3H, d, J = 6.5 Hz), 1.13 (3H, d, J = 7.1 Hz), 1.20-1.50 (10H, m), 1.50-1.65 (3H, m), 1.66 (3H, d, J = 5.6 Hz), 1.67-2.45 (30H, m), 2.46 (1H, d, J = 4.9 Hz), 2.90 (3H, s), 2.99 (3H, s), 3.04 (3H, s), 3.06 (3H, s), 3.07 (3H, s), 3.17 (3H, s), 3.35 (3H, s), 3.36 (3H, s), 3.40-3.90 (9H, m), 4.15-4.40 (2H, m), 4.55 (1H, t-like), 4.72 (1H, t, J = 7.2 Hz), 4.80-5.10 (9H, m), 5.15 (1H, dd, J = 11.4, 4.0 Hz), 5.20-5.60 (3H, m), 5.67 (1H, d, J = 3.2 Hz), 6.76 (1H, d, J = 8.4 Hz), 6.95 (1H, d, J = 7.4 Hz), 6.99 (1H, d, J = 6.8 Hz), 7.65 (1H, d, J = 9.3 Hz), 9.26 (1H, d, J = 9.0 Hz). (for a major conformer) MS: 1407.05 |
| 222 | MS: 1346.04 |
| 223 | NMR: 0.71 (3H, d, J = 6.7 Hz), 0.81 (6H, dd, J = 6.5, 2.7 Hz), 0.85 (3H, d, J = 6.5 Hz), 0.88 (3H, d, J = 6.6 Hz), 0.91 (6H, t, J = 6.6 Hz), 0.95-1.08 (8H, m), 1.10 (3H, d, J = 6.5 Hz), 1.12 (3H, d, J = 7.1 Hz), 1.15-1.50 (10H, m), 1.50-1.65 (3H, m), 1.66 (3H, d, J = 5.6 Hz), 1.65-2.25 (19H, m), 2.25-2.44 (2H, m), 2.45 (1H, d, J = 4.9 Hz), 2.50-2.75 (8H, m), 2.91 (3H, s), 2.98 (3H, s), 3.04 (3H, s), 3.05 (3H, s), 3.07 (3H, s), 3.17 (3H, s), 4.10-4.30 (2H, m), 4.54 (1H, t-like, J = 7.0 Hz), 4.73 (1H, t-like, J = 7.2 Hz), 4.75-5.13 (5H, m), 5.15 (1H, dd, J = 11.4, 4.0 Hz), 5.20-5.60 (5H, m), 5.67 (1H, d, J = 3.2 Hz), 6.76 (1H, d, J = 8.2 Hz), 6.89 (1H, d, J = 7.6 Hz), 6.96 (1H, d, J = 8.9 Hz), 7.65 (1H, d, J = 8.9 Hz), 9.08 (1H, d, J = 9.4 Hz). (for a major conformer) MS: 1333.96 |
| 224 | MS: 1330.01 |
| 225 | MS: 1362.08 |
| 226 | MS: 1362.07 |
| 227 | MS: 1392.07 |
| 228 | NMR: 0.71 (3H, d, J = 6.7 Hz), 0.80 (3H, d, J = 6.5 Hz), 0.81 (3H, d, J = 6.6 Hz), 0.85 (3H, d, J = 6.7 Hz), 0.87 (3H, d, J = 6.6 Hz), 0.90 (3H, d, J = 7.0 Hz), 0.92-0.97 (8H, m), 1.10 (3H, d, J = 6.5 Hz), 1.12 (3H, d, J = 7.1 Hz), 1.17-1.49 (10H, m), 1.49-1.63 (3H, m), 1.66 (3H, d, J = 5.6 Hz), 1.68-2.15 (12H, m), 2.19 (1H, d, J = 11.4 Hz), 2.25-2.43 (12H, m), 2.45 (1H, d, J = 4.9 Hz), 2.91 (3H, s), 3.02 (3H, s), 3.06 (3H, s), 3.07 (3H, s), 3.07 (3H, s), 3.17 (3H, s), 3.34 (3H, s), 3.36 (3H, s), 3.37 (3H, s), 3.45-3.64 (6H, m), 3.70-3.83 (3H, m), 4.17-4.25 (1H, m), 4.25-4.31 (1H, m), 4.53 (1H, dd, J = 8.8, 7.1 Hz), 4.70 (1H, t, J = 7.2 Hz), 4.75-4.84 (1H, m), 4.86 (1H, dd, J = 9.4, 2.4 Hz), 4.91-5.03 (3H, m), 5.09 (1H, dd, J = 10.2, 5.1 Hz), 5.15 (1H, dd, J = 11.4, 4.0 Hz), 5.23-5.57 (3H, m), 5.65 (1H, d, J = 3.2 Hz), 6.76 (1H, d, J = 8.2 Hz), 6.87 (1H, d, J = 7.6 Hz), 6.97 (1H, d, J = 8.9 Hz), 7.67 (1H, d, J = 9.0 Hz), 8.96 (1H, d, J = 9.4 Hz). (for a major conformer) MS: 1436.11 |
| 229 | MS: 1438.14 |
| 230 | NMR: 0.71 (3H, d, J = 6.8 Hz), 0.81 (6H, d, J = 6.5 Hz), 0.84-1.07 (17H, m), 1.10 (3H, d, J = 6.5 Hz), 1.12 (3H, d, J = 6.9 Hz), 1.16-1.49 (10H, m), 1.49-1.63 (3H, m), 1.66 (3H, d, J = 5.4 Hz), 1.68-2.46 (25H, m), 2.50 (1H, d, J = 4.8 Hz), 2.90 (3H, s), 3.03 (3H, s), 3.05 (9H, s), 3.17 (3H, s), 3.37 (3H, s), 3.52-3.80 (7H, m), 4.18-4.31 (2H, m), 4.53 (1H, dd, J = 8.9, 7.0 Hz), 4.70 (1H, t, J = 7.2 Hz), 4.74-4.83 (1H, m), 4.86 (1H, dd, J = 9.3, 2.1 Hz), 4.91-5.03 (3H, m), 5.09 (1H, dd, J = 10.0, 5.2 Hz), 5.15 (1H, dd, J = 11.4, 3.9 Hz), 5.30-5.56 (3H, m), 5.65 (1H, d, J = 3.3 Hz), 6.76 (1H, d, J = 8.1 Hz), 6.96 (1H, d, J = 7.5 Hz), 6.99 (1H, d, J = 9.0 Hz), 7.67 (1H, d, J = 9.0 Hz), 9.26 (1H, d, J = 9.3 Hz). (for a major conformer) MS: 1348.01 |
| 231 | MS: 1392.15 |
| 232 | NMR: 0.71 (3H, d, J = 7.0 Hz), 0.78-1.45 (43H, m), 1.09 (3H, d, J = 6.4 Hz), 1.12 (3H, d, J = 6.8 Hz), 1.34 (3H, d, J = 6.8 Hz), 1.42 (3H, d, J = 7.4 Hz), 1.50-2.52 (23H, m), 2.90 (3H, s), 2.98 (3H, s), 3.06 (3H, s), 3.08 (3H, s), 3.20 (3H, s), 3.43-3.54 (8H, m), 3.92 (2H, d, J = 6.1 Hz), 4.15-4.32 (2H, m) |

TABLE 9-continued

| Ex | Data |
|---|---|
| | 4.53 (1H, dd, J = 8.6, 7.1 Hz), 4.69 (1H, t-like, J = 7.1 Hz), 4.78 (1H, dd, J = 14.4, 7.4 Hz), 4.81-5.00 (2H, m), 5.03 (1H, dd, J = 10.3, 5.0 Hz), 5.18 (1H, dd, J = 11.5, 4.2 Hz), 5.28-5.57 (4H, m), 5.67 (1H, d, J = 3.3 Hz), 6.91 (1H, d, J = 7.1 Hz), 6.92 (1H, d, J = 8.5 Hz), 7.02 (1H, d, J = 8.9 Hz), 7.49 (1H, d, J = 8.9 Hz), 9.32 (1H, d, J = 9.3 Hz). (for a major conformer) MS: 1408.16, ESI (M + Na)⁺: 1392.8 |
| 233 | MS: 1374.7 |
| 234 | MS: 1417.88 |
| 235 | NMR: 0.71 (3H, d, J = 6.8 Hz), 0.78-1.04 (23H, m), 0.82 (3H, d, J = 6.4 Hz), 0.82 (3H, d, J = 6.5 Hz), 0.87 (3H, d, J = 6.8 Hz), 0.92 (3H, d, J = 6.7 Hz), 1.10 (3H, d, J = 6.4 Hz), 1.17 (3H, d, J = 6.5 Hz), 1.21-2.86 (22H, m), 1.43 (3H, d, J = 7.3 Hz), 2.92 (3H, s), 3.01 (3H, s), 3.01 (3H, s), 3.06 (3H, s), 3.09 (3H, s), 3.20 (3H, s), 3.22 (3H, s), 3.34 (3H, s), 3.38 (3H, s), 3.40-3.62 (6H, m), 3.72-4.02 (7H, m), 4.17-4.30 (2H, m), 4.82-5.05 (3H, m), 4.85 (1H, dd, J = 9.2, 2.4 Hz), 5.07-5.18 (3H, m), 5.28-5.56 (3H, m), 5.31 (1H, d, J = 10.4 Hz), 5.38 (1H, dd, J = 12.2, 3.2 Hz), 5.63 (1H, d, J = 3.2 Hz), 6.88 (1H, d, J = 8.6 Hz), 7.45 (1H, d, J = 8.8 Hz), 7.60 (1H, d, J = 10.0 Hz), 8.98 (1H, d, J = 9.2 Hz). (for a major conformer) MS: 1450.00 |
| 236 | MS: 1420.06 |
| 237 | MS: 1452.15 |
| 238 | MS: 1351.60 |
| 239 | ESI (M + Na)⁺: 1384.9 |
| 240 | MS: 1475.79 |
| 241 | MS: 1382.26 |
| 242 | ESI (M + Na)⁺: 1472.9 |
| 243 | ESI (M + Na)⁺: 1343.8 |
| 244 | MS: 1388.97 |
| 245 | ESI (M + Na)⁺: 1441.9 |
| 246 | ESI (M + H₂O)⁺: 1404.88 |
| 247 | MS: 1390.75 |
| 248 | MS: 1370.57 |
| 249 | MS: 1370.80 |
| 250 | MS: 1388.69 |
| 251 | MS: 1370.14 |
| 252 | MS: 1376.75 |
| 253 | MS: 1393.39 |
| 254 | MS: 1395.41 |
| 255 | MS: 1391.36 |
| 256 | MS: 1404.36 |
| 257 | NMR: 0.71 (3H, d, J = 6.8 Hz), 0.79-1.05 (14H, m), 0.81 (3H, d, J = 6.5 Hz), 0.82 (3H, d, J = 6.4 Hz), 0.87 (3H, d, J = 6.6 Hz), 0.90 (3H, d, J = 6.7 Hz), 0.92 (3H, d, J = 6.8 Hz), 0.94 (3H, d, J = 6.6 Hz), 1.03 (3H, d, J = 6.6 Hz), 1.09 (3H, d, J = 6.4 Hz), 1.12 (3H, d, J = 6.9 Hz), 1.33 (3H, d, J = 6.8 Hz), 1.38 (3H, d, J = 7.4 Hz), 1.51-1.69 (9H, m), 1.69-2.16 (9H, m), 2.26-2.65 (7H, m), 2.91 (3H, s), 2.96 (3H, s), 2.99 (3H, s), 3.05 (6H, s), 3.06 (3H, s), 3.17 (3H, s), 3.18-3.58 (6H, m), 3.37 (3H, s), 3.42 (3H, s), 3.84-4.00 (2H, m), 4.18-4.30 (2H, m), 4.52 (1H, dd, J = 8.8, 6.9 Hz), 4.70 (1H, t-like, J = 7.1 Hz), 4.76-5.04 (4H, m), 5.06 (1H, dd, J = 10.1, 5.2 Hz), 5.15 (1H, dd, J = 11.4, 4.0 Hz), 5.35 (2H, d, J = 10.4 Hz), 5.69 (1H, d, J = 3.3 Hz), 6.77 (1H, d, J = 8.2 Hz), 6.95 (1H, d, J = 7.3 Hz), 7.01 (1H, d, J = 8.9 Hz), 7.62 (1H, d, J = 9.0 Hz), 9.31 (1H, d, J = 9.2 Hz). (for a major conformer) MS: 1410.26 |
| 258 | MS: 1408.28 |
| 259 | MS: 1394.11 |
| 260 | MS: 1364.09 |
| 261 | MS: 1408.14 |
| 262 | MS: 1320.00 |
| 263 | MS: 1320.05 |
| 264 | NMR: 0.71 (3H, d, J = 6.8 Hz), 0.81 (3H, d, J = 6.4 Hz), 0.81 (3H, d, J = 6.4 Hz), 0.84-1.07 (17H, m), 1.09 (3H, d, J = 6.5 Hz), 1.12 (3H, d, J = 7.0 Hz), 1.16-2.46 (45H, m), 2.51 (1H, d, J = 4.8 Hz), 2.91 (3H, s), 3.02 (3H, s), 3.06 (9H, s), 3.17 (3H, s), 3.37 (3H, s), 3.52-3.87 (7H, m), 4.18-4.29 (2H, m), 4.52 (1H, dd, J = 8.8, 7.0 Hz), 4.70 (1H, t, J = 7.2 Hz), 4.74-4.84 (1H, m), 4.87 (1H, dd, J = 9.4, 2.1 Hz), 4.91-5.03 (3H, m), 5.08 (1H, dd, J = 10.2, 5.1 Hz), 5.15 (1H, dd, J = 11.5, 4.0 Hz), 5.28-5.42 (1H, m), 5.68 (1H, d, J = 3.3 Hz), 6.77 (1H, d, J = 8.2 Hz), 6.92 (1H, d, J = 7.5 Hz), 6.97 (1H, d, J = 8.9 Hz), 7.66 (1H, d, J = 9.0 Hz), 9.17 (1H, d, J = 9.2 Hz). (for a major conformer) MS: 1350.09 |
| 265 | MS: 1394.08 |

TABLE 10

[Structure of cyclic peptide with substituents A and G]

| Prep | A | G |
|---|---|---|
| 2-A | (4-NO₂-Ph)-O—C(O)—O— | —H |
| 2-B | (4-NO₂-Ph)-O—C(O)—O— | —C(O)—O—(4-NO₂-Ph) |
| 21 | ᵗBu-Si(Me)₂-(O)— | —H |
| 24 | HO₂C—CH₂—O— | —H |
| 25 | HO—(CH₂)₂—O— | —H |
| 26 | (4-NO₂-Ph)-O—C(O)—O—(CH₂)₂—O— | —H |
| 27 | (4-Me-Ph)-SO₂—O—(CH₂)₂—O— | —H |
| 29 | Me-NH— | —H |
| 30 | (4-Me-Ph)-SO₂—O— | —H |
| 31-A | (4-Me-Ph)-SO₂—O— | —Si(Me)₂-ᵗBu |
| 31-B | Cl— | —Si(Me)₂-ᵗBu |
| 32 | Ph-S— | —Si(Me)₂-ᵗBu |
| 33 | Ph-S(O)₂— | —Si(Me)₂-ᵗBu |
| 34 | HS— | —H |
| 35 | [2,4-(F)₂-Ph]—O— | —Si(Me)₂-ᵗBu |
| 36 | N₃— | —H |
| 37 | N₃— | —Si(Me)₂-ᵗBu |
| 38 | Ph-CH₂—NH— | —Si(Me)₂-ᵗBu |
| 39 | H₂N— | —H |
| 41 | I— | —H |
| 118 | ᵗBu-Si(Me)₂-O— | —Si(Me)₂-ᵗBu |

TABLE 11
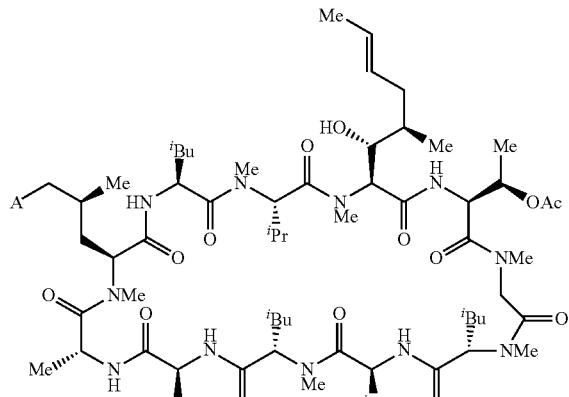
| Prep | A |
|---|---|
| 22 | HO— |
| 23 | EtO$_2$C—CH$_2$—O— |
TABLE 12
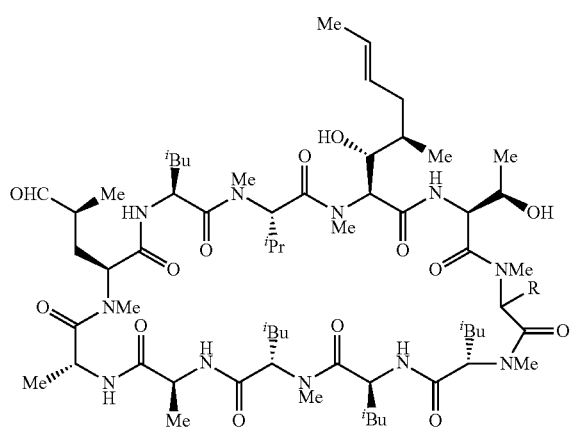
| Prep | R |
|---|---|
| 28 | —H |
| 93 | ⋯Me |
| 94 | ⋯CH$_2$OMe |
TABLE 13
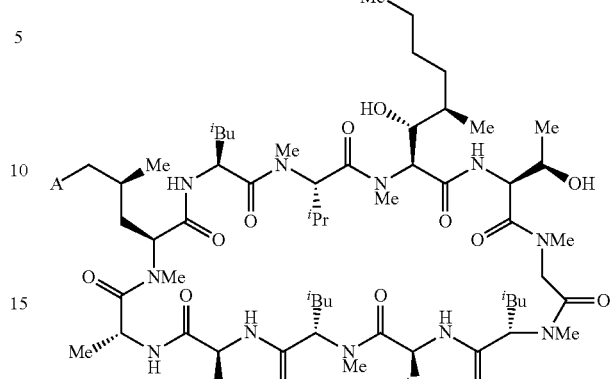
| Prep | A |
|---|---|
| 40. | H$_2$N— |
TABLE 14
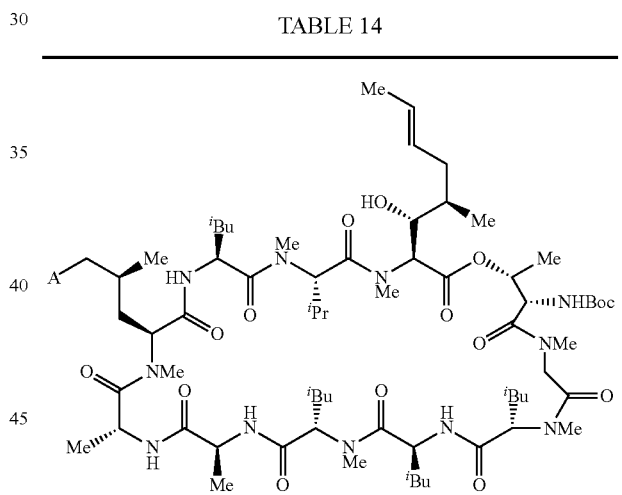
| Prep | A |
|---|---|
| 80/125 | |
| 136 | HO— <br> (4-Me-1-Pipa)-C(O)—O— |

TABLE 15
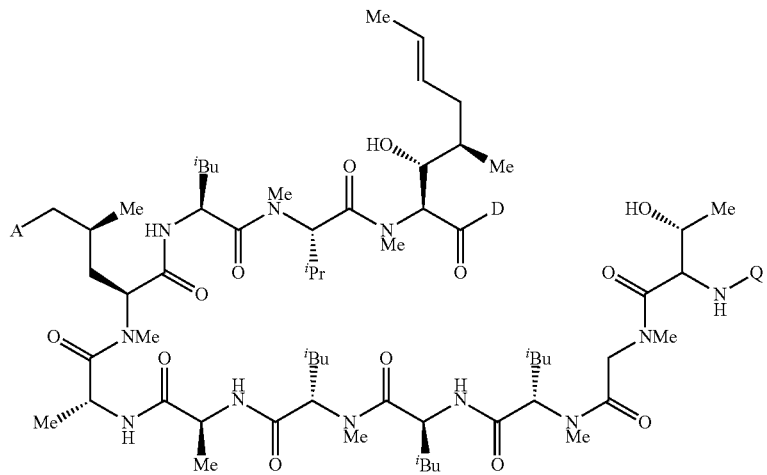
| Prep | A | D | Q |
|------|---|---|---|
| 81 | HO— | —OH | -Boc |
| 82 | HO— | 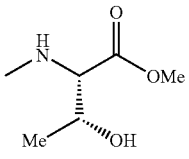 | -Boc |
| 83 | AcO— | 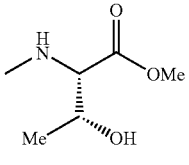 | -Boc |
| 84 | AcO— | 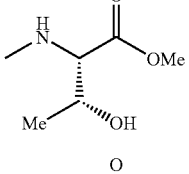 | —H |
| 85 | AcO— | 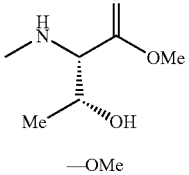 | —C(S)—NH-Ph |
| 126 | HO— | —OMe | -Boc |
| 127 | AcO— | —OMe | -Boc |
| 128 | AcO— | —OMe | —H |
| 137 | (4-Me-1-Pipa)-C(O)—O— | —OH | -Boc |
| 138 | (4-Me-1-Pipa)-C(O)—O— | 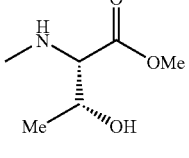 | -Boc |
| 139 | (4-Me-1-Pipa)-C(O)—O— | 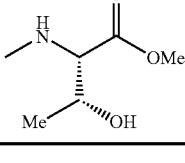 | —C(S)—NH-Ph |

TABLE 16
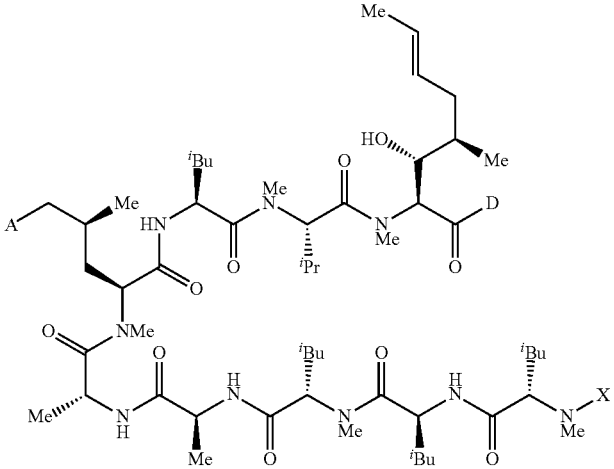
| Prep | A | D | X |
|---|---|---|---|
| 86 | AcO— | 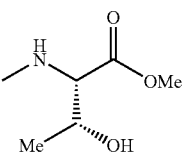 | —C(O)—CH₂—NH-Me |
| 87 | AcO— | 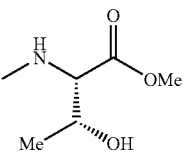 | 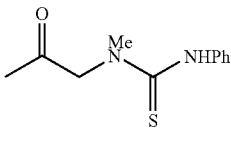 |
| 88 | AcO— | 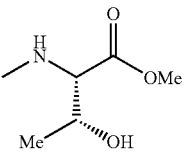 | —H |
| 89 | AcO— | 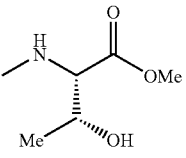 | 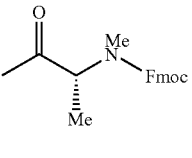 |
| 90 | HO— | 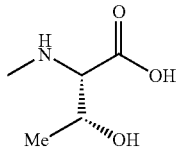 | 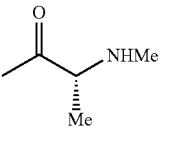 |
| 100 | AcO— | 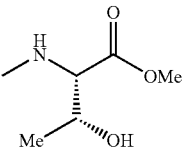 | 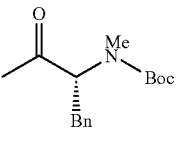 |

TABLE 16-continued
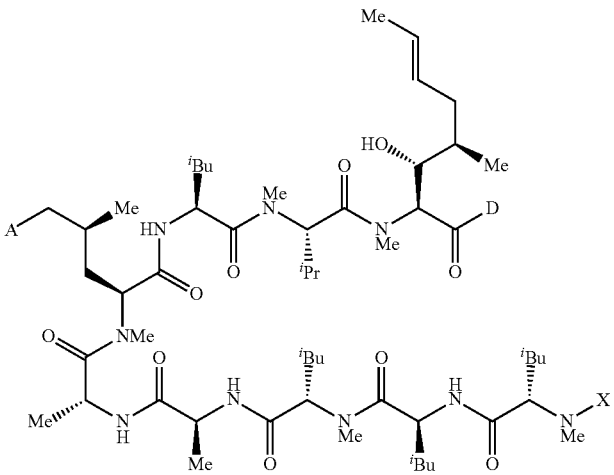
| Prep | A | D | X |
|---|---|---|---|
| 101 | HO— | 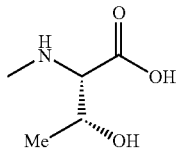 | 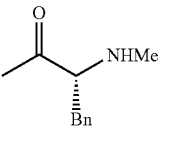 |
| 104 | AcO— | 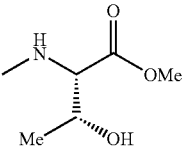 | 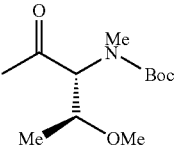 |
| 105 | HO— | 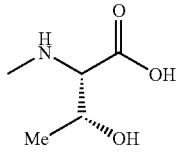 | 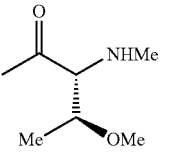 |
| 129 | AcO— | —OMe | —C(O)—CH$_2$—NH-Me |
| 130 | AcO— | —OMe | —H |
| 131 | AcO— | —OMe | 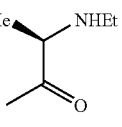 |
| 132 | AcO— | —OMe | 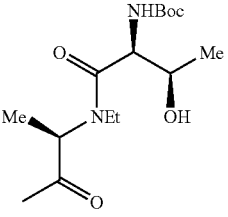 |
| 133 | HO— | —OH | 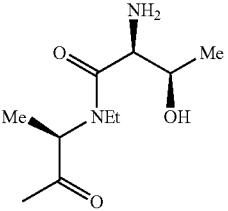 |

TABLE 16-continued

| Prep | A | D | X |
|---|---|---|---|
| 140 | (4-Me-1-Pipa)-C(O)—O— | MeNH-CH(CH(OH)Me)-C(O)OMe | CH3-C(O)-CH2-N(Me)-C(S)-NHPh |
| 141 | (4-Me-1-Pipa)-C(O)—O— | MeNH-CH(CH(OH)Me)-C(O)OMe | —H |
| 142 | (4-Me-1-Pipa)-C(O)—O— | MeNH-CH(CH(OH)Me)-C(O)OMe | CH3-C(O)-CH(Me)-N(Me)-Fmoc |
| 143 | (4-Me-1-Pipa)-C(O)—O— | MeNH-CH(CH(OH)Me)-C(O)OH | CH3-C(O)-CH(Me)-NHMe |
| 144 | (4-Me-1-Pipa)-C(O)—O— | MeNH-CH(CH(OH)Me)-C(O)OMe | CH3-C(O)-CH(Me)-N(Et)-Fmoc |
| 145 | (4-Me-1-Pipa)-C(O)—O— | MeNH-CH(CH(OH)Me)-C(O)OH | CH3-C(O)-CH(Me)-NHEt |

TABLE 16-continued

| Prep | A    | D                          | X                              |
|------|------|----------------------------|--------------------------------|
| 151  | AcO— | NHMe, OMe, Me, OH          | N(Me)(Boc), Et                 |
| 152  | AcO— | NHMe, OMe, Me, OH          | NHMe, Et                       |
| 153  | HO—  | NHMe, OH, Me, OH           | NHMe, Et                       |
| 155  | AcO— | NHMe, OMe, Me, OH          | N(Me)(Boc), CH₂OMe             |
| 156  | AcO— | NHMe, OMe, Me, OH          | NHMe, CH₂OMe                   |
| 157  | HO—  | NHMe, OH, Me, OH           | NHMe, CH₂OMe                   |

TABLE 17
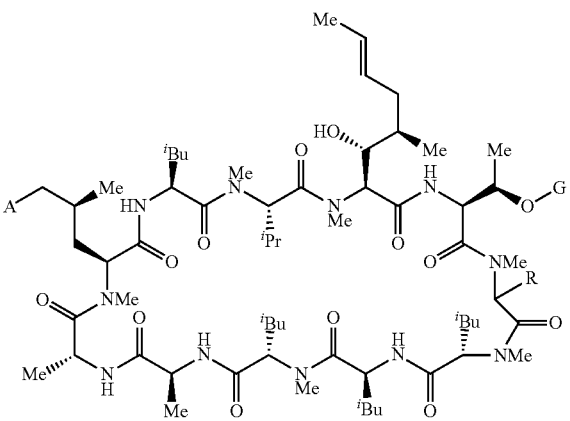
| Prep | A | G | R |
|---|---|---|---|
| 91 | HO— | —H | ⋯Me |
| 92 | (4-NO₂-Ph)-O—C(O)—O— | —H | ⋯Me |
| 95 | ᵗBu-Si(Me)₂-O— | —Si(Me)₂-ᵗBu | ⋯Et |
| 96/154 | HO— | —H | ⋯Et |
| 97 | (4-NO₂-Ph)-O—C(O)—O— | —H | ⋯Et |
| 98 | HO— | —H | ⋯CH₂—CH=CH₂ |
| 99 | (4-NO₂-Ph)-O—C(O)—O— | —H | ⋯CH₂—CH=CH₂ |
| 102 | HO— | —H | ⋯Bn |
| 103 | (4-NO₂-Ph)-O—C(O)—O— | —H | ⋯Bn |
| 106 | HO— | —H | ⋯CH(Me)OMe |
| 107 | (4-NO₂-Ph)-O—C(O)—O— | —H | ⋯CH(Me)OMe |
| 108 | ᵗBu-Si(Me)₂-O— | —Si(Me)₂-ᵗBu | ⋯CH₂OAc |
| 109 | HO— | —H | ⋯CH₂OAc |
| 110 | (4-NO₂-Ph)-O—C(O)—O— | —H | ⋯CH₂OAc |
| 111 | ᵗBu-Si(Me)₂-O— | —Si(Me)₂-ᵗBu | ⋯CH₂OEt |
| 112 | HO— | —H | ⋯CH₂OEt |
| 113 | (4-NO₂-Ph)-O—C(O)—O— | —H | ⋯CH₂OEt |
| 114 | (4-Me-Ph)-SO₂—O— | —H | ⋯Me |
| 115 | N₃— | —H | ⋯Me |
| 116 | H₂N— | —H | ⋯Me |
| 117 | Et-NH— | —H | ⋯Me |

TABLE 17-continued
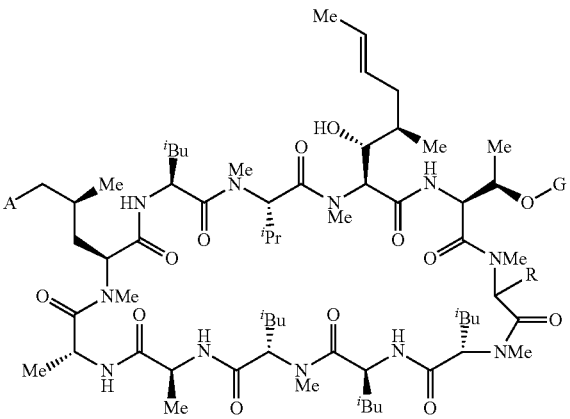
| Prep | A | G | R |
|---|---|---|---|
| 119 | ᵗBu-Si(Me)₂-O— | —Si(Me)₂-ᵗBu | ⋯CH₂OH |
| 120 | ᵗBu-Si(Me)₂-O— | —Si(Me)₂-ᵗBu | ⋯CH₂OMe |
| 121/158 | HO— | —H | ⋯CH₂OMe |
| 122 | ᵗBu-Si(Me)₂-O— | —Si(Me)₂-ᵗBu | 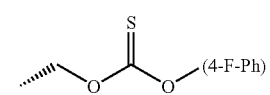 |
| 123 | (4-NO₂-Ph)-O—C(O)—O— | —H | ⋯Me |
| 124 | (4-NO₂-Ph)-O—C(O)—O— | —H | ⋯CH₂OMe |
TABLE 18
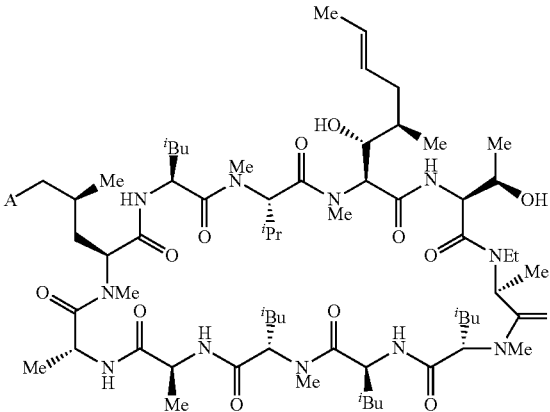
| Prep | A |
|---|---|
| 134 | HO— |
| 135 | (4-NO₂-Ph)-O—C(O)—O— |
TABLE 19
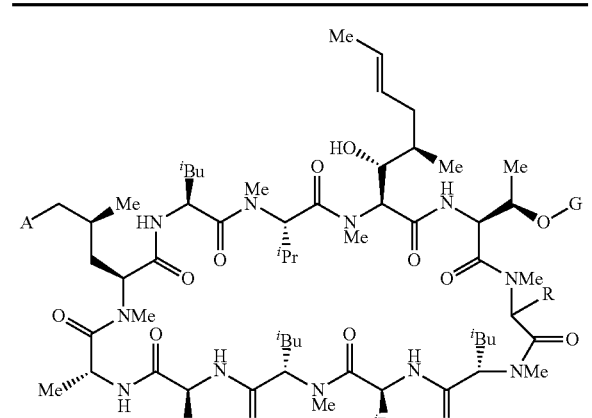
| Prep | A | G | R |
|---|---|---|---|
| 146 | ᵗBu-Si(Me)₂-O— | —Si(Me)₂-ᵗBu | —H |
| 147 | ᵗBu-Si(Me)₂-O— | —Si(Me)₂-ᵗBu | ⋯CH₂OH |

TABLE 19-continued

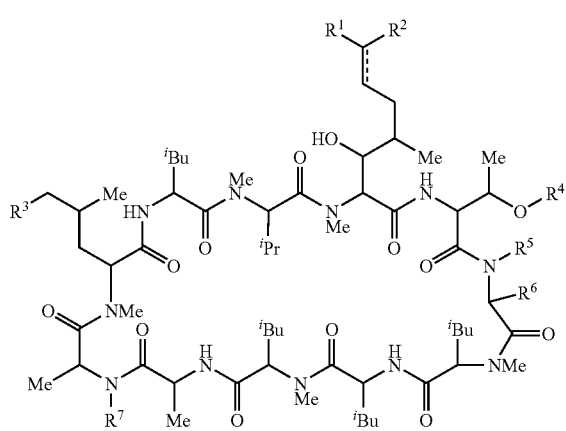

| Prep | A | G | R |
|---|---|---|---|
| 148 | tBu-Si(Me)₂-O— | —Si(Me)₂-tBu | ........CH₂OMe |
| 149 | HO— | —OH | ........CH₂OMe |
| 150 | (4-NO₂-Ph)-O—C(O)—O— | —OH | ........CH₂OMe |

The invention claimed is:

1. A cyclic peptide compound of the following general formula (I):

(I)

wherein
$R^1$ is methyl;
$R^2$ is hydrogen;
$R^3$ is
(1) —$NR^8R^9$, wherein $R^8$ and $R^9$ are independently hydrogen, lower alkyl, heterocyclic group or acyl, each of which may have one or more suitable substituent(s);

or alternatively $R^8$ and $R^9$, together with the nitrogen atom to which they are attached, represent an N-containing heterocyclic group which may have one or more suitable substituent(s); or (2) —OC(O)—$NR^{10}R^{11}$, wherein $R^{10}$ and $R^{11}$ are independently hydrogen, lower alkyl, cyclo (lower) alkyl, aryl or heterocyclic group, each of which may have one or more suitable substituent(s);

or alternatively $R^{10}$ and $R^{11}$, together with the nitrogen atom to which they are attached, represent an N-containing heterocyclic group, which may have one or more suitable substituent(s);

$R^4$ is hydrogen;

$R^5$ is methyl or ethyl;

$R^6$ is hydrogen or lower alkyl which may have one or more suitable substituent(s);

$R^7$ is hydrogen;
and
═══ represents single bond or a double bond;
or a salt thereof.

2. A pharmaceutical composition which comprises, a compound of claim 1 or a pharmaceutically acceptable salt thereof in admixture with pharmaceutically acceptable carriers or excipients.

3. A method for the therapeutic treatment of hepatitis C, which comprises administering a compound of claim 1 or a pharmaceutically acceptable salt thereof to a human being or an animal.

4. A compound of claim 1 which is
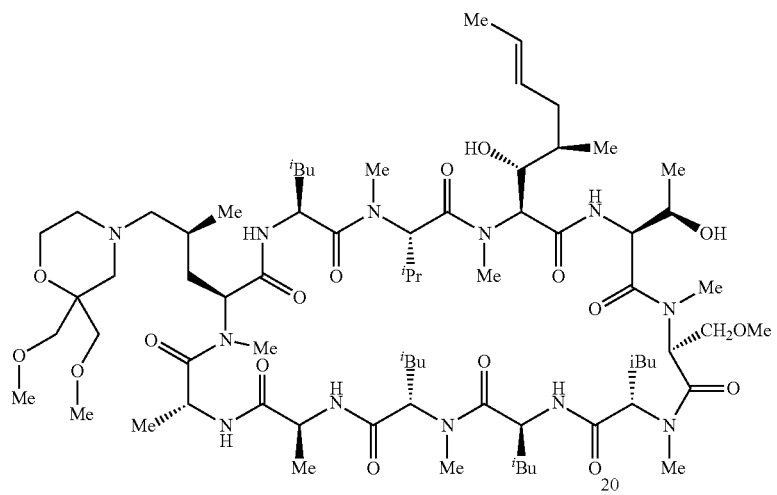
or a salt thereof.
5. A compound of claim 1 which is
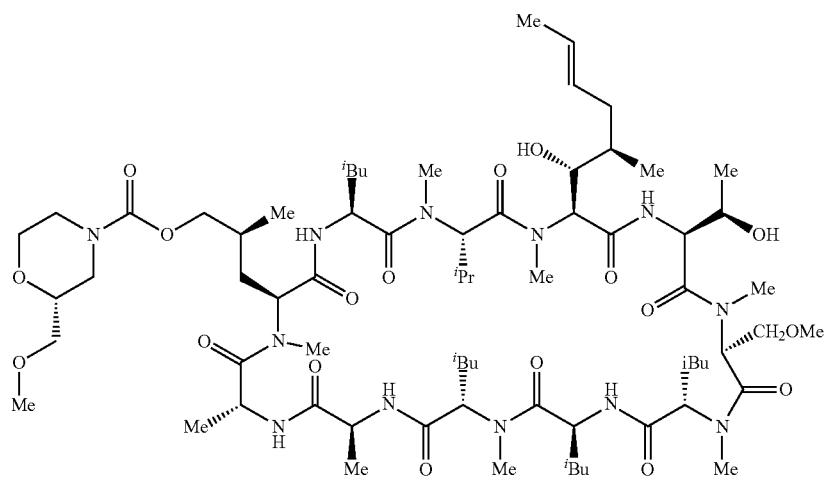
or a salt thereof.
* * * * *